United States Patent
Iglesias et al.

(10) Patent No.: US 9,616,138 B1
(45) Date of Patent: Apr. 11, 2017

(54) CARGO CARRYING NANOPARTICLES

(71) Applicants: Raul Iglesias, Brandon, FL (US); Piyush Koria, Tampa, FL (US)

(72) Inventors: Raul Iglesias, Brandon, FL (US); Piyush Koria, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/498,988

(22) Filed: Sep. 26, 2014

Related U.S. Application Data

(60) Provisional application No. 61/882,892, filed on Sep. 26, 2013, provisional application No. 61/884,417, filed on Sep. 30, 2013.

(51) Int. Cl.
| | |
|---|---|
| *A61K 38/00* | (2006.01) |
| *A61K 47/48* | (2006.01) |
| *C07K 14/475* | (2006.01) |
| *A61K 38/18* | (2006.01) |
| *A61K 38/10* | (2006.01) |
| *C07K 14/485* | (2006.01) |
| *C07K 14/78* | (2006.01) |

(52) U.S. Cl.
CPC ........ *A61K 47/48292* (2013.01); *A61K 38/10* (2013.01); *A61K 38/1825* (2013.01); *C07K 14/475* (2013.01); *C07K 14/485* (2013.01); *C07K 14/78* (2013.01); *C07K 2319/10* (2013.01); *C07K 2319/33* (2013.01); *C07K 2319/735* (2013.01)

(58) Field of Classification Search
CPC .......... A61K 47/48292; A61K 38/1825; A61K 38/10; C07K 14/485; C07K 14/475; C07K 14/78; C07K 2319/735; C07K 2319/33; C07K 2319/10
See application file for complete search history.

(56) References Cited

U.S. PATENT DOCUMENTS

| | | |
|---|---|---|
| 2013/0178411 A1 | 7/2013 | Chilkoti |
| 2013/0210747 A1 | 8/2013 | Hamm-Alvarez |

OTHER PUBLICATIONS

Mercer et al, Virus entry by macropinocytosis, Nature Cell Biology, 2009, 11, pp. 510-520.*
Lim et al, Macropinocytosis: an endocytic pathway for internalising large gulps, Immunology and Cell Biology, 2011, 89, pp. 836-843.*
Kou et al, The endocytosis and intracellular fate of nanomedicines: Implication for rational design, Asian Journal of Pharmaceutical Sciences, 2013, 8, pp. 1-10.*
Megeed et al, Self-Assembling Multifunctional Nanoparticles from Elastin-Like Polypeptides, Proceedings Published 2007 by the American Chemical Society, p. 1.*
Kaplan et al, Cationic TAT peptide transduction domain enters cells by macropinocytosis, Journal of Controlled Release, 2005, 102, pp. 247-253.*
Ignatovich et al, Complexes of Plasmid DNA with Basic Domain 47-57 of the HIV-1 Tat Protein Are Transferred to Mammalian Cells by Endocytosis-mediated Pathways, The Journal of Biological Chemistry, 2003, 278, pp. 42625-42636.*
Peer et al, Nanocarriers as an emerging platform for cancer therapy, Nature nanotechnology, 2007, 2, p. 751-760.*
Bachran et al, Chimeric toxins inhibit growth of primary oral squamous cell carcinoma cells, Cancer Biology & Therapy, 2008, 7, pp. 237-242.*
Pelicano et al, Glycolysis inhibition for anticancer treatment, Oncogene, 2006, 25, pp. 4633-4646.*
Hassouneh et al, Fusions of Elastin-Like Polypeptides to Pharmaceutical Proteins, Methods in Enzymology, 2012, 502, pp. 215-237, available online on Dec. 29, 2011.*
Matsuda et al, Fibroblast Growth Factor Receptor 2: Expression, Roles, and Potential as a Novel Molecular Target for Colorectal Cancer, Pathology Research International, 2012, pp. 1-8, published online on Jun. 4, 2012.*
KGF amino acid sequence, from http://www.ncbi.nlm.nih.gov/protein/P21781.1, pp. 1-3, accessed Aug. 1, 2013.*
Cohen, Optimization of Dose-Time Factors for a Tumor and Multiple Associated Normal Tissues, Int. J. Radiat. Oncol. Biol. Phys., 1987, 13, pp. 251-258.*
Glickson et al, Lipoprotein Nanoplatform for Targeted Delivery of Diagnostic and Therapeutic Agents, Molecular Imaging, 2008, 7, pp. 101-110.*
Karagiannis, et al., Rational Design of a Biomimetic Cell Penetrating Peptide Library; Institute of Integrative Cancer Research; vol. 7, No. 10, 2013.
Koria, et al., Self-assembling elastin-like peptides growth factor chimeric nanoparticles for the treatment of chronic wounds; PNAS, vol. 108, No. 3, Jan. 2011.
Terpe, K., Overview of tag protein fusions: from molecular and biochemical fundamentals to commerical systems; Appl Micro. Bio., 2003.
Falcone, et al., Macropinocytosis: regulated coordination of endocytic and exocytic membrane traffic events; Journal of Cell Science; Aug. 31, 2006.
Kerr, et al., Defining Macropinocytosis; 2009 Blackwell Munksgaard.

(Continued)

*Primary Examiner* — Julie Ha
*Assistant Examiner* — Li Ni Komatsu
(74) *Attorney, Agent, or Firm* — Thomas | Horstemeyer, LLP

(57) ABSTRACT

Disclosed herein are cargo carrying nanoparticles and pharmaceutical formulations thereof. The cargo carrying nanoparticles can self-assemble from cargo molecule subunits and/or targeting subunits. The cargo carrying molecules can be configured to induce macropinocytosis in a cell when a targeting moiety specifically binds a binding partner on the surface of a cell. The pharmaceutical formulations containing the cargo carrying nanoparticles disclosed herein can be administered to a patient for the treatment or prevention of cancer.

18 Claims, 28 Drawing Sheets

(56) References Cited

OTHER PUBLICATIONS

Cai, et al., One-pot synthesis of elastin-like polypeptide hydrogels with frated VEGF-mimetic peptides; Biomater. Sci, 2014.
Machado, et al., 2. Thermoresponsive self-assembled elastin-based nanoparticles for delivery of BMPs; Abstracts of Papers, 239th ACS National Meeting, San Francisco, CA, United States, Mar. 21-25, 2010 (2010), PMSE-490. Publisher: (American Chemical Society, Washington, D. C).

* cited by examiner

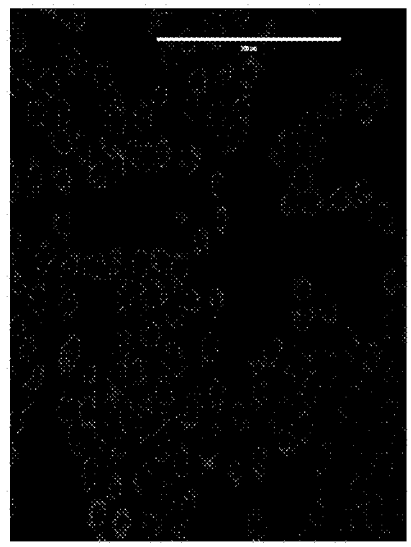 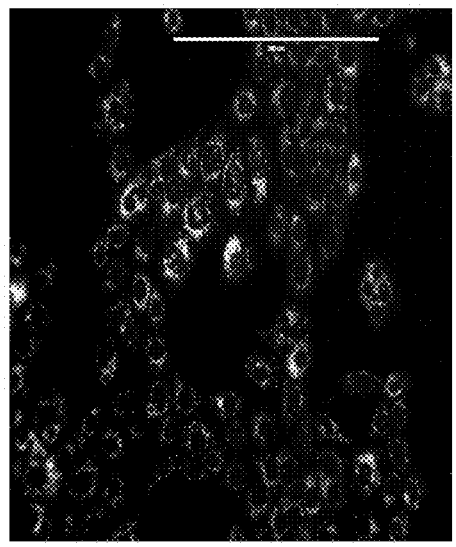
Figure 16A    Figure 16B
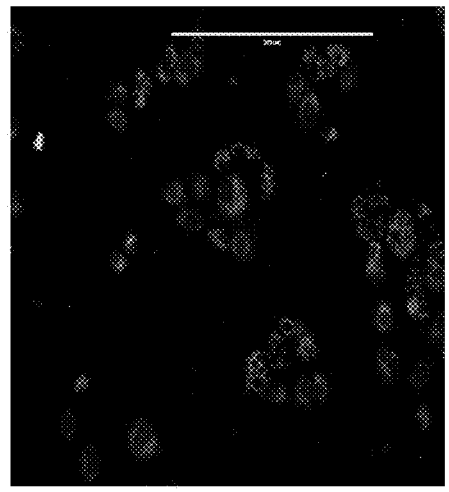
Figure 16C

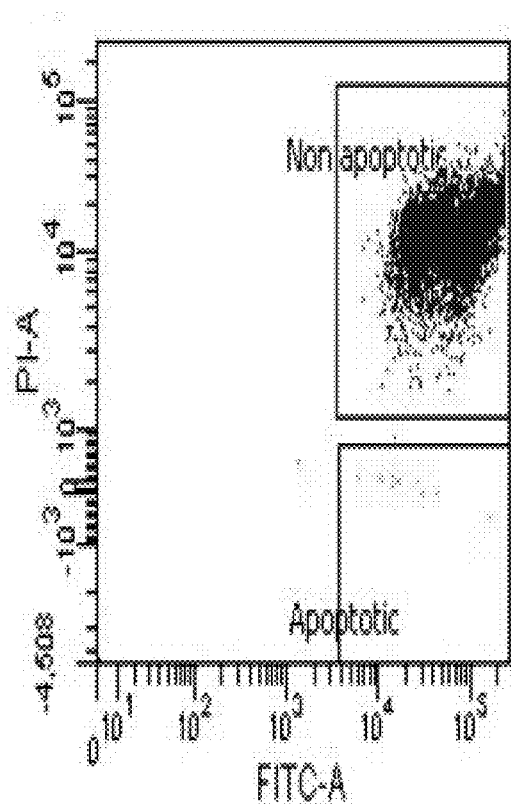 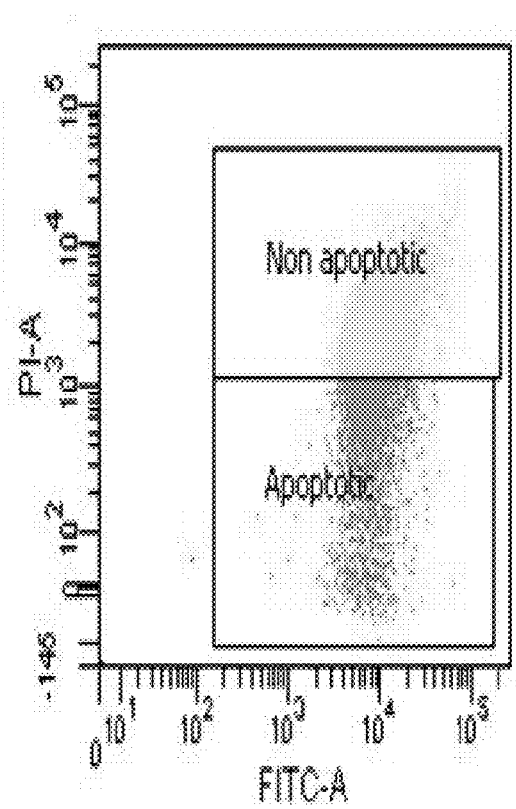
Figure 18A     Figure 18B

Figure 23A Figure 23B
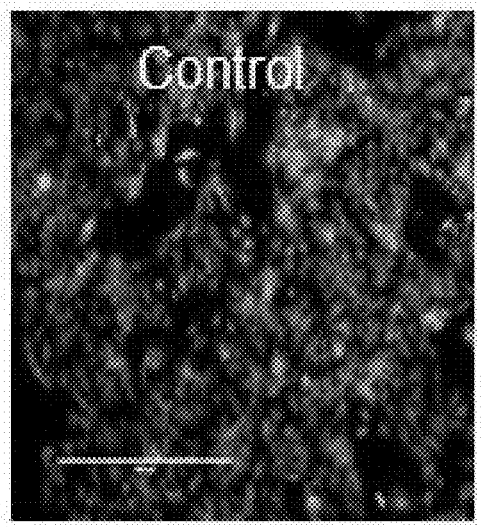 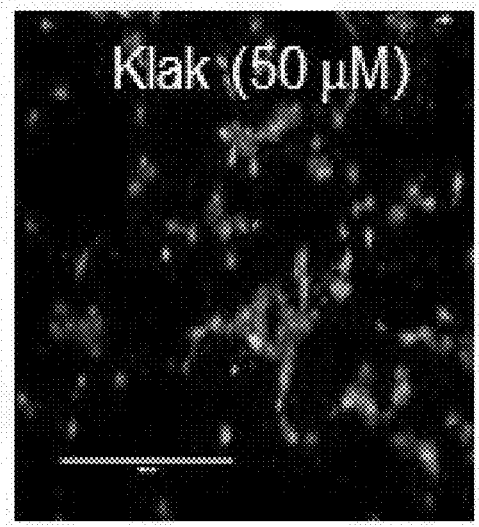
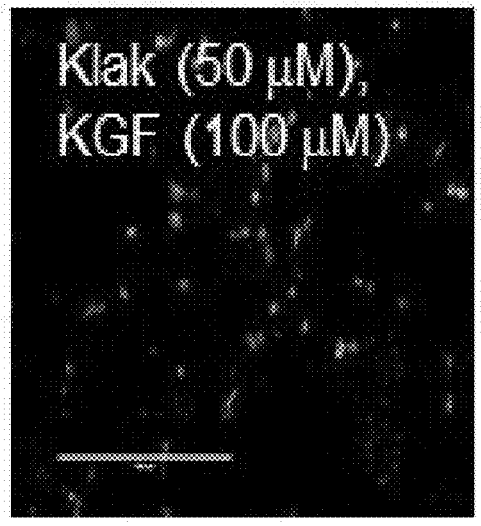 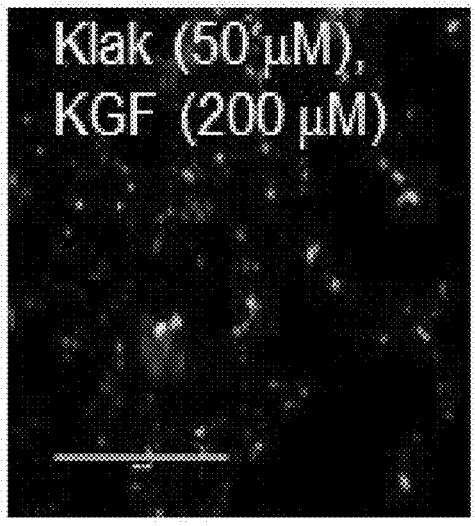
Figure 23C Figure 23D

SEQUENCE LISTING

```
<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: ELP sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Pro Gly Xaa Gly
1               5
```

<210> SEQ ID NO 2
<211> LENGTH: 25
<212> TYPE: PRT
<213> ORGANISM: Artificial Sequence
<220> FEATURE:
<223> OTHER INFORMATION: ELP sequence

<400> SEQUENCE: 2

Val Pro Gly Val Gly Val Pro Gly Val Gly Val Pro Gly Cys Gly Val
1               5                   10                  15

Pro Gly Val Gly Val Pro Gly Val Gly
            20                  25

<210> SEQ ID NO 3
<211> LENGTH: 25
<212> TYPE: PRT
<213> ORGANISM: Artificial Sequence
<220> FEATURE:
<223> OTHER INFORMATION: ELP sequence

<400> SEQUENCE: 3

Val Pro Gly Val Gly Val Pro Gly Val Gly Val Pro Gly Met Gly Val
1               5                   10                  15

Pro Gly Val Gly Val Pro Gly Val Gly
            20                  25

<210> SEQ ID NO 4
<211> LENGTH: 25
<212> TYPE: PRT
<213> ORGANISM: Artificial Sequence
<220> FEATURE:
<223> OTHER INFORMATION: ELP sequence

<400> SEQUENCE: 4

Val Pro Gly Val Gly Val Pro Gly Val Gly Val Pro Gly Ile Gly Val
1               5                   10                  15

Pro Gly Val Gly Val Pro Gly Val Gly
            20                  25

<210> SEQ ID NO 5
<211> LENGTH: 25
<212> TYPE: PRT
<213> ORGANISM: Artificial Sequence
<220> FEATURE:
<223> OTHER INFORMATION: ELP sequence

<400> SEQUENCE: 5

Val Pro Gly Val Gly Val Pro Gly Val Gly Val Pro Gly Leu Gly Val
1               5                   10                  15

Pro Gly Val Gly Val Pro Gly Val Gly
            20                  25

<210> SEQ ID NO 6
<211> LENGTH: 25
<212> TYPE: PRT
<213> ORGANISM: Artificial Sequence
<220> FEATURE:
<223> OTHER INFORMATION: ELP sequence

<400> SEQUENCE: 6

Val Pro Gly Val Gly Val Pro Gly Val Gly Val Pro Gly Phe Gly Val
1               5                   10                  15

Pro Gly Val Gly Val Pro Gly Val Gly 20                  25

<210> SEQ ID NO 7
<211> LENGTH: 25
<212> TYPE: PRT
<213> ORGANISM: Artificial Sequence
<220> FEATURE:
<223> OTHER INFORMATION: ELP sequence

<400> SEQUENCE: 7

Val Pro Gly Val Gly Val Pro Gly Val Gly Val Pro Gly Trp Gly Val
1               5                   10                  15

Pro Gly Val Gly Val Pro Gly Val Gly
            20                  25

<210> SEQ ID NO 8
<211> LENGTH: 750
<212> TYPE: DNA
<213> ORGANISM: Artificial Sequence
<220> FEATURE:
<223> OTHER INFORMATION: cDNA for ELP (V40C2)

<400> SEQUENCE: 8
gttccgggcg taggtgtccc aggtgtgggc gtaccgggcg ttggtgttcc tggtgtcggc        60
gtgccgggcg tgggtgttcc gggcgtaggt gtcccaggtg tgggcgtacc gggcgttggt       120
gttcctggtg tcggcgtgcc gggcgtgggt gttccgggcg taggtgtccc aggtgtgggc       180
gtaccgggcg ttggtgttcc tggtgtcggc gtgccgggcg tgggtgttcc gggcgtaggt       240
gtcccaggtg tgggcgtacc gggcgttggt gttcctggtg tcggcgtgcc gggcgtgggt       300
gttccgggcg taggtgtccc aggtgtgggc gtaccgggcg ttggtgttcc tggtgtcggc       360
gtgccgggcg tgggtgttcc gggcgtaggt gtcccaggtg tgggcgtacc gggcgttggt       420
gttcctggtg tcggcgtgcc gggcgtgggt gttccgggcg taggtgtccc aggtgtgggc       480
gtaccgggcg ttggtgttcc tggtgtcggc gtgccgggcg tgggtgttcc gggcgtaggt       540
gtcccaggtg tgggcgtacc gggcgttggt gttcctggtg tcggcgtgcc gggcgtgggt       600
gttccgggcg taggtgtccc aggtgtgggc gtaccgggct gcggtgttcc tggtgtcggc       660
gtgccgggcg tgggtgttcc gggcgtaggt gtcccaggtg tgggcgtacc gggctgcggt       720
gttcctggtg tcggcgtgcc gggcgtgggt                                         750

<210> SEQ ID NO 9
<211> LENGTH: 250
<212> TYPE: PRT
<213> ORGANISM: Artificial Sequence
<220> FEATURE:
<223> OTHER INFORMATION: polypeptide sequence for ELP (V40C2)

<400> SEQUENCE: 9

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
            85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
            165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Cys Gly Val Pro Gly Val Gly Val Pro Gly Val
    210                 215                 220

Gly Val Pro Gly Val Gly Val Pro Gly Val Gly Val Pro Gly Cys Gly
225                 230                 235                 240

Val Pro Gly Val Gly Val Pro Gly Val Gly
            245                 250

<210> SEQ ID NO 10
<211> LENGTH: 159
<212> TYPE: DNA
<213> ORGANISM: Artificial Sequence
<220> FEATURE:
<223> OTHER INFORMATION: cDNA human EGF

<400> SEQUENCE: 10
aatagtgact ctgaatgtcc cctgtcccac gatgggtact gcctccatga tggtgtgtgc      60
atgtatattg aagcattgga caagtatgca tgcaactgtg ttgttggcta catcggggag     120
cgatgtcagt accgagacct gaagtggtgg gaactgcgc                            159

<210> SEQ ID NO 11
<211> LENGTH: 53
<212> TYPE: PRT
<213> ORGANISM: Artificial Sequence
<220> FEATURE:
<223> OTHER INFORMATION: polypeptide human EGF

<400> SEQUENCE: 11

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 12
<211> LENGTH: 582
<212> TYPE: DNA
<213> ORGANISM: Artificial Sequence
<220> FEATURE:
<223> OTHER INFORMATION: KGF cDNA

<400> SEQUENCE: 12

```
atgcacaaat ggatactgac atggatcctg ccaactttgc tctacagatc atgctttcac      60
attatctgtc tagtgggtac tatatcttta gcttgcaatg acatgactcc agagcaaatg     120
gctacaaatg tgaactgttc cagccctgag cgacacacaa gaagttatga ttacatggaa     180
ggagggata taagagtgag aagactcttc tgtcgaacac agtggtacct gaggatcgat      240
aaaagaggca agtaaaagg gacccaagag atgaagaata attacaatat catgaaaatc      300
aggacagtgg cagttggaat tgtggcaatc aaaggggtgg aaagtgaatt ctatcttgca     360
atgaacaagg aaggaaaact ctatgcaaag aaagaatgca atgaagattg taacttcaaa     420
gaactaattc tggaaaaacca ttacaacaca tatgcatcag ctaaatggac acacaacgga     480
ggggaaatgt ttgttgcctt aaatcaaaag gggattcctg taagaggaaa aaaaacgaag     540
aaagaacaaa aacagcccca ctttcttcct atggcaataa ct                        582
```

<210> SEQ ID NO 13
<211> LENGTH: 194
<212> TYPE: PRT
<213> ORGANISM: Artificial Sequence
<220> FEATURE:
<223> OTHER INFORMATION: KGF polypeptide sequence

<400> SEQUENCE: 13

```
Met His Lys Trp Ile Leu Thr Trp Ile Leu Pro Thr Leu Leu Tyr Arg
 1               5                  10                  15
Ser Cys Phe His Ile Ile Cys Leu Val Gly Thr Ile Ser Leu Ala Cys
                20                  25                  30
Asn Asp Met Thr Pro Glu Gln Met Ala Thr Asn Val Asn Cys Ser Ser
            35                  40                  45
Pro Glu Arg His Thr Arg Ser Tyr Asp Tyr Met Glu Gly Gly Asp Ile
        50                  55                  60
Arg Val Arg Arg Leu Phe Cys Arg Thr Gln Trp Tyr Leu Arg Ile Asp
65                  70                  75                  80
Lys Arg Gly Lys Val Lys Gly Thr Gln Glu Met Lys Asn Asn Tyr Asn
                85                  90                  95
Ile Met Glu Ile Arg Thr Val Ala Val Gly Ile Val Ala Ile Lys Gly
            100                 105                 110
Val Glu Ser Glu Phe Tyr Leu Ala Met Asn Lys Glu Gly Lys Leu Tyr
        115                 120                 125
Ala Lys Lys Glu Cys Asn Glu Asp Cys Asn Phe Lys Glu Leu Ile Leu
    130                 135                 140
Glu Asn His Tyr Asn Thr Tyr Ala Ser Ala Lys Trp Thr His Asn Gly
145                 150                 155                 160
Gly Glu Met Phe Val Ala Leu Asn Gln Lys Gly Ile Pro Val Arg Gly
                165                 170                 175
Lys Lys Thr Lys Lys Glu Gln Lys Thr Ala His Phe Leu Pro Met Ala
            180                 185                 190
Ile Thr
```

<210> SEQ ID NO 14
<211> LENGTH: 353
<212> TYPE: DNA
<213> ORGANISM: Artificial Sequence
<220> FEATURE:
<223> OTHER INFORMATION: platelet derived growth factor cDNA

<400> SEQUENCE: 14

-continued

| | | |
|---|---|---|
| ccacggcgtg ggttcactgg gctccctgac catcgctgaa ccggcaatga tcgctgaatg | 60 | |
| taaaacccgt accgaagtct ttgaaatctc tcgtcgtctg attgatcgta ccaacgcaaa | 120 | |
| tttctggtg tggccgccgt gcgtggaagt tcagcgctgt agcggctgct gtaacaatcg | 180 | |
| taacgtgcaa tgccgtccga cgcaggttca actgcgtccg gtccaggtgc gcaaaattga | 240 | |
| aatcgtccgt aaaaagccga tcttcaaaaa ggctaccgtt acgctggaag accatctggc | 300 | |
| gtgcaagtgt gaaaccgttg cggccgcacg cccggtcacg gtgccgggct ggc | 353 | |

```
<210> SEQ ID NO 15
<211> LENGTH: 3633
<212> TYPE: DNA
<213> ORGANISM: Artificial Sequence
<220> FEATURE:
<223> OTHER INFORMATION: epidermal growth factor receptor cDNA

<400> SEQUENCE: 15
```

| | | |
|---|---|---|
| atgcgaccct ccgggacggc cggggcagcg ctcctggcgc tgctggctgc gctctgcccg | 60 | |
| gcgagtcggg ctctggagga aaagaaagtt tgccaaggca cgagtaacaa gctcacgcag | 120 | |
| ttgggcactt tgaagatca tttctcagc ctccagagga tgttcaataa ctgtgaggtg | 180 | |
| gtccttggga atttggaaat acctatgtg cagaggaatt atgatctttc cttcttaaag | 240 | |
| accatccagg aggtggctgg ttatgtcctc attgccctca acacagtgga gcgaattcct | 300 | |
| ttggaaaacc tgcagatcat cagaggaaat atgtactacg aaaattccta tgccttagca | 360 | |
| gtcttatcta actatgatgc aaataaaacc ggactgaagg agctgcccat gagaaattta | 420 | |
| caggaaatcc tgcatggcgc cgtgcggttc agcaacaacc ctgccctgtg caacgtggag | 480 | |
| agcatccagt ggcgggacat agtcagcagt gactttctca gcaacatgtc gatggacttc | 540 | |
| cagaaccacc tgggcagctg ccaaaagtgt gatccaagct gtcccaatgg agctgctgg | 600 | |
| ggtgcaggag aggagaactg ccagaaactg accaaaatca tctgtgccca gcagtgctcc | 660 | |
| gggcgctgcc gtggcaagtc ccccagtgac tgctgccaca accagtgtgc tgcaggctgc | 720 | |
| acaggccccc gggagagcga ctgcctggtc tgccgcaaat tccgagacga agccacgtgc | 780 | |
| aaggacacct gccccccact catgctctac aaccccacca cgtaccagat ggatgtgaac | 840 | |
| cccgagggca atacagcttt ggtgccacc tgcgtgaaga gtgtccccg taattatgtg | 900 | |
| gtgacagatc acggctcgtg cgtccgagcc tgtgggccg acagctatga gatggaggaa | 960 | |
| gacggcgtcc gcaagtgtaa gaagtgcgaa gggccttgcc gcaaagtgtg taacggaata | 1020 | |
| ggtattggtg aatttaaaga ctcactctcc ataaatgcta cgaatattaa acacttcaaa | 1080 | |
| aactgcacct ccatcagtgg cgatctccac atcctgccgg tggcatttag gggtgactcc | 1140 | |
| ttcacacata ctcctcctct ggatccacag gaactggata ttctgaaaac cgtaaaggaa | 1200 | |
| atcacagggt tttgctgat tcaggcttgg cctgaaaaca ggacggacct ccatgccttt | 1260 | |
| gagaacctag aaatcatacg cggcaggacc aagcaacatg tcagttttc tcttgcagtc | 1320 | |
| gtcagcctga acataacatc cttgggatta cgctccctca aggagataag tgatggagat | 1380 | |
| gtgataattt caggaaacaa aaatttgtgc tatgcaaata caataaactg gaaaaaactg | 1440 | |
| tttgggaccct ccgtcagaa aaccaaaatt ataagcaaca gaggtgaaaa cagctgcaag | 1500 | |
| gccacaggcc aggtctgcca tgccttgtgc tcccccgagg gctgctgggg cccggagccc | 1560 | |
| agggactgcg tctcttgccg gaatgtcagc cgaggcaggg aatgcgtgga caagtgcaac | 1620 | |
| cttctggagg gtgagccaag ggagtttgtg gagaactctc agtgcataca gtgccaccca | 1680 | |

```
gagtgcctgc ctcaggccat gaacatcacc tgcacaggac ggggaccaga caactgtatc    1740
cagtgtgccc actacattga cggcccccac tgcgtcaaga cctgcccggc aggagtcatg    1800
ggagaaaaca acaccctggt ctggaagtac gcagacgccg ccatgtgtg ccacctgtgc     1860 catccaaact gcacctacgg atgcactggg ccaggtcttg aaggctgtcc aacgaatggg    1920
cctaagatcc cgtccatcgc cactgggatg gtgggggccc tcctcttgct gctggtggtg    1980
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta agggactc tggatcccag aaggtgagaa agttaaaatt      2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc     2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatcccacc agagtgatgt ctggagctac     2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg gctgcaaag ctgtcccatc     3180 aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac     3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                3633
```

<210> SEQ ID NO 16  
<211> LENGTH: 1209  
<212> TYPE: PRT  
<213> ORGANISM: Artificial Sequence  
<220> FEATURE:  
<223> OTHER INFORMATION: epidermal growth factor receptor polypeptide

<400> SEQUENCE: 16

```
Met Arg Pro Ser Gly Thr Ala Gly Ala Ala Leu Leu Ala Leu Leu Ala
1               5                  10                 15
```

-continued

```
Ala Leu Cys Pro Ala Ser Arg Ala Leu Glu Lys Lys Val Cys Gln
            20                  25                  30
Gly Thr Ser Asn Lys Leu Thr Gln Leu Gly Thr Phe Glu Asp His Phe
        35                  40                  45
Leu Ser Leu Gln Arg Met Phe Asn Asn Cys Glu Val Val Leu Gly Asn
    50                  55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
            100                 105                 110
Tyr Glu Asn Ser Tyr Ala Leu Ala Val Leu Ser Asn Tyr Asp Ala Asn
        115                 120                 125
Lys Thr Gly Leu Lys Glu Leu Pro Met Arg Asn Leu Gln Glu Ile Leu
    130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Met Asp Phe Gln Asn His Leu Gly Ser Cys Gln Lys Cys Asp Pro Ser
            180                 185                 190
Cys Pro Asn Gly Ser Cys Trp Gly Ala Gly Glu Glu Asn Cys Gln Lys
        195                 200                 205
Leu Thr Lys Ile Ile Cys Ala Gln Gln Cys Ser Gly Arg Cys Arg Gly
    210                 215                 220
Lys Ser Pro Ser Asp Cys Cys His Asn Gln Cys Ala Ala Gly Cys Thr
225                 230                 235                 240
Gly Pro Arg Glu Ser Asp Cys Leu Val Cys Arg Lys Phe Arg Asp Glu
                245                 250                 255
Ala Thr Cys Lys Asp Thr Cys Pro Pro Leu Met Leu Tyr Asn Pro Thr
            260                 265                 270
Thr Tyr Gln Met Asp Val Asn Pro Glu Gly Lys Tyr Ser Phe Gly Ala
        275                 280                 285
Thr Cys Val Lys Lys Cys Pro Arg Asn Tyr Val Val Thr Asp His Gly
    290                 295                 300
Ser Cys Val Arg Ala Cys Gly Ala Asp Ser Tyr Glu Met Glu Glu Asp
305                 310                 315                 320
Gly Val Arg Lys Cys Lys Lys Cys Glu Gly Pro Cys Arg Lys Val Cys
                325                 330                 335
Asn Gly Ile Gly Ile Gly Glu Phe Lys Asp Ser Leu Ser Ile Asn Ala
            340                 345                 350
Thr Asn Ile Lys His Phe Lys Asn Cys Thr Ser Ile Ser Gly Asp Leu
        355                 360                 365
His Ile Leu Pro Val Ala Phe Arg Gly Asp Ser Phe Thr His Thr Pro
    370                 375                 380
Pro Leu Asp Pro Gln Glu Leu Asp Ile Leu Lys Thr Val Lys Glu Ile
385                 390                 395                 400
Thr Gly Phe Leu Leu Ile Gln Ala Trp Pro Glu Asn Arg Thr Asp Leu
                405                 410                 415
His Ala Phe Glu Asn Leu Glu Ile Ile Arg Gly Arg Thr Lys Gln His
            420                 425                 430
Gly Gln Phe Ser Leu Ala Val Val Ser Leu Asn Ile Thr Ser Leu Gly
```

```
              435                 440                 445
Leu Arg Ser Leu Lys Glu Ile Ser Asp Gly Asp Val Ile Ile Ser Gly
450                 455                 460

Asn Lys Asn Leu Cys Tyr Ala Asn Thr Ile Asn Trp Lys Lys Leu Phe
465                 470                 475                 480

Gly Thr Ser Gly Gln Lys Thr Lys Ile Ile Ser Asn Arg Gly Glu Asn
                    485                 490                 495

Ser Cys Lys Ala Thr Gly Gln Val Cys His Ala Leu Cys Ser Pro Glu
                500                 505                 510

Gly Cys Trp Gly Pro Glu Pro Arg Asp Cys Val Ser Cys Arg Asn Val
            515                 520                 525

Ser Arg Gly Arg Glu Cys Val Asp Lys Cys Asn Leu Leu Glu Gly Glu
        530                 535                 540

Pro Arg Glu Phe Val Glu Asn Ser Glu Cys Ile Gln Cys His Pro Glu
545                 550                 555                 560

Cys Leu Pro Gln Ala Met Asn Ile Thr Cys Thr Gly Arg Gly Pro Asp
                    565                 570                 575

Asn Cys Ile Gln Cys Ala His Tyr Ile Asp Gly Pro His Cys Val Lys
                580                 585                 590

Thr Cys Pro Ala Gly Val Met Gly Glu Asn Asn Thr Leu Val Trp Lys
            595                 600                 605

Tyr Ala Asp Ala Gly His Val Cys His Leu Cys His Pro Asn Cys Thr
610                 615                 620

Tyr Gly Cys Thr Gly Pro Gly Leu Glu Gly Cys Pro Thr Asn Gly Pro
625                 630                 635                 640

Lys Ile Pro Ser Ile Ala Thr Gly Met Val Gly Ala Leu Leu Leu Leu
                    645                 650                 655

Leu Val Val Ala Leu Gly Ile Gly Leu Phe Met Arg Arg His Ile
                660                 665                 670

Val Arg Lys Arg Thr Leu Arg Arg Leu Leu Gln Glu Arg Glu Leu Val
            675                 680                 685

Glu Pro Leu Thr Pro Ser Gly Glu Ala Pro Asn Gln Ala Leu Leu Arg
        690                 695                 700

Ile Leu Lys Glu Thr Glu Phe Lys Lys Ile Lys Val Leu Gly Ser Gly
705                 710                 715                 720

Ala Phe Gly Thr Val Tyr Lys Gly Leu Trp Ile Pro Glu Gly Glu Lys
                    725                 730                 735

Val Lys Ile Pro Val Ala Ile Lys Glu Leu Arg Glu Ala Thr Ser Pro
                740                 745                 750

Lys Ala Asn Lys Glu Ile Leu Asp Glu Ala Tyr Val Met Ala Ser Val
            755                 760                 765

Asp Asn Pro His Val Cys Arg Leu Leu Gly Ile Cys Leu Thr Ser Thr
        770                 775                 780

Val Gln Leu Ile Thr Gln Leu Met Pro Phe Gly Cys Leu Leu Asp Tyr
785                 790                 795                 800

Val Arg Glu His Lys Asp Asn Ile Gly Ser Gln Tyr Leu Leu Asn Trp
                    805                 810                 815

Cys Val Gln Ile Ala Lys Gly Met Asn Tyr Leu Glu Asp Arg Arg Leu
                820                 825                 830

Val His Arg Asp Leu Ala Ala Arg Asn Val Leu Val Lys Thr Pro Gln
            835                 840                 845

His Val Lys Ile Thr Asp Phe Gly Leu Ala Lys Leu Leu Gly Ala Glu
        850                 855                 860
```

Glu Lys Glu Tyr His Ala Glu Gly Gly Lys Val Pro Ile Lys Trp Met
865                 870                 875                 880

Ala Leu Glu Ser Ile Leu His Arg Ile Tyr Thr His Gln Ser Asp Val
                885                 890                 895

Trp Ser Tyr Gly Val Thr Val Trp Glu Leu Met Thr Phe Gly Ser Lys
            900                 905                 910

Pro Tyr Asp Gly Ile Pro Ala Ser Glu Ile Ser Ser Ile Leu Glu Lys
        915                 920                 925

Gly Glu Arg Leu Pro Gln Pro Pro Ile Cys Thr Ile Asp Val Tyr Met
930                 935                 940

Ile Met Val Lys Cys Trp Met Ile Asp Ala Asp Ser Arg Pro Lys Phe
945                 950                 955                 960

Arg Glu Leu Ile Ile Glu Phe Ser Lys Met Ala Arg Asp Pro Gln Arg
                965                 970                 975

Tyr Leu Val Ile Gln Gly Asp Glu Arg Met His Leu Pro Ser Pro Thr
            980                 985                 990

Asp Ser Asn Phe Tyr Arg Ala Leu Met Asp Glu Glu Asp Met Asp Asp
        995                 1000                1005

Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser
    1025                1030                1035

Ala Thr Ser Asn Asn Ser Thr Val Ala Cys Ile Asp Arg Asn Gly
    1040                1045                1050

Leu Gln Ser Cys Pro Ile Lys Glu Asp Ser Phe Leu Gln Arg Tyr
    1055                1060                1065

Ser Ser Asp Pro Thr Gly Ala Leu Thr Glu Asp Ser Ile Asp Asp
    1070                1075                1080

Thr Phe Leu Pro Val Pro Glu Tyr Ile Asn Gln Ser Val Pro Lys
    1085                1090                1095

Arg Pro Ala Gly Ser Val Gln Asn Pro Val Tyr His Asn Gln Pro
    1100                1105                1110

Leu Asn Pro Ala Pro Ser Arg Asp Pro His Tyr Gln Asp Pro His
    1115                1120                1125

Ser Thr Ala Val Gly Asn Pro Glu Tyr Leu Asn Thr Val Gln Pro
    1130                1135                1140

Thr Cys Val Asn Ser Thr Phe Asp Ser Pro Ala His Trp Ala Gln
    1145                1150                1155

Lys Gly Ser His Gln Ile Ser Leu Asp Asn Pro Asp Tyr Gln Gln
    1160                1165                1170

Asp Phe Phe Pro Lys Glu Ala Lys Pro Asn Gly Ile Phe Lys Gly
    1175                1180                1185

Ser Thr Ala Glu Asn Ala Glu Tyr Leu Arg Val Ala Pro Gln Ser
    1190                1195                1200

Ser Glu Phe Ile Gly Ala
    1205

<210> SEQ ID NO 17
<211> LENGTH: 2310
<212> TYPE: DNA
<213> ORGANISM: Artificial Sequence
<220> FEATURE:
<223> OTHER INFORMATION: KGF-Receptor cDNA (FGFR2 iiib)

<400> SEQUENCE: 17

```
atggtcagct ggggtcgttt catctgcctg gtcgtggtca ccatggcaac cttgtccctg      60 gcccggcccct ccttcagttt agttgaggat accacattag agccagaaga gccaccaacc    120
aaataccaaa tctctcaacc agaagtgtac gtggctgcgc caggggagtc gctagaggtg    180
cgctgcctgt tgaaagatgc cgccgtgatc agttggacta aggatggggt gcacttgggg    240
cccaacaata ggacagtgct tattgggag tacttgcaga taaagggcgc cacgcctaga     300
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt cgctgccca     540 gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accgcccat cctccaagcc     780 ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagc actcggggat aaatagttcc    960
aatgcagaag tgctggctct gttcaatgtg accgaggcgg atgctgggga atatatatgt   1020
aaggtctcca attatatagg gcaggccaac cagtctgcct ggctcactgt cctgccaaaa   1080
cagcaagcgc ctggaagaga aaggagatt acagcttccc cagactacct ggagatagcc    1140
atttactgca taggggtctt cttaatcgcc tgtatggtgg taacagtcat cctgtgccga    1200
atgaagaaca cgaccaagaa gccagacttc agcagccagc cggctgtgca caagctgacc   1260
aaacgtatcc ccctgcggag acaggtaaca gtttcggctg agtccagctc ctccatgaac   1320
tccaacaccc cgctggtgag gataacaaca cgcctctctt caacggcaga cacccccatg   1380
ctggcagggg tctccgagta tgaacttcca gaggacccaa aatgggagtt tccaagagat   1440
aagctgacac tgggcaagcc cctgggagaa ggttgctttg gcaagtggt catggcggaa    1500 gcagtgggaa ttgacaaaga caagcccaag gaggcggtca ccgtggccgt gaagatgttg   1560
aaagatgatg ccacagagaa agaccttct gatctggtgt cagagatgga gatgatgaag    1620
atgattggga acacaagaa tatcataaat cttcttggag cctgcacaca ggatgggcct    1680
ctctatgtca tagttgagta tgcctctaaa ggcaacctcc gagaatacct ccgagcccgg   1740
aggccacccg ggatggagta ctcctatgac attaaccgtg ttcctgagga gcagatgacc   1800
ttcaaggact tggtgtcatg cacctaccag ctggccagag gcatggagta cttggcttcc   1860
caaaaatgta ttcatcgaga tttagcagcc agaaatgttt tggtaacaga aaacaatgtg   1920
atgaaaatag cagactttgg actcgccaga gatatcaaca atatagacta ttacaaaaag   1980
accaccaatg gcggcttcc agtcaagtgg atggctccag aagccctgtt tgatagagta   2040
tacactcatc agagtgatgt ctggtccttc ggggtgttaa tgtgggagat cttcactta    2100 gggggctcgc cctacccagg gattcccgtg gaggaacttt ttaagctgct gaaggaagga   2160
cacagaatgg ataagccagc caactgcacc aacgaactgt acatgatgat gagggactgt   2220
tggcatgcag tgcccctccca gagaccaacg ttcaagcagt tggtagaaga cttggatcga   2280
attctcactc tcacaaccaa tgagatctga                                     2310
```

<210> SEQ ID NO 18
<211> LENGTH: 769
<212> TYPE: PRT
<213> ORGANISM: Artificial Sequence
<220> FEATURE:
<223> OTHER INFORMATION: KGF-Receptor polypeptide (FGFR2 iiib)

<400> SEQUENCE: 18

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365
```

```
Glu Ile Thr Ala Ser Pro Asp Tyr Leu Glu Ile Ala Ile Tyr Cys Ile
370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
            405                 410                 415

His Lys Leu Thr Lys Arg Ile Pro Leu Arg Arg Gln Val Thr Val Ser
            420                 425                 430

Ala Glu Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
            755                 760                 765

Ile
```

<210> SEQ ID NO 19

<211> LENGTH: 3321
<212> TYPE: DNA
<213> ORGANISM: Artificial Sequence
<220> FEATURE:
<223> OTHER INFORMATION: platelet derived growth factor cDNA

<400> SEQUENCE: 19

| | |
|---|---|
| atgcggcttc cgggtgcgat gccagctctg gccctcaaag gcgagctgct gttgctgtct | 60 |
| ctcctgttac ttctggaacc acagatctct cagggcctgg tcgtcacacc cccggggcca | 120 |
| gagcttgtcc tcaatgtctc cagcaccttc gttctgacct gctcgggttc agctccggtg | 180 |
| gtgtgggaac ggatgtccca ggagccccca caggaaatgg ccaaggccca ggatggcacc | 240 |
| ttctccagcg tgctcacact gaccaacctc actgggctag acacgggaga atacttttgc | 300 |
| acccacaatg actcccgtgg actggagacc gatgagcgga acggctcta catctttgtg | 360 |
| ccagatccca ccgtgggctt cctccctaat gatgccgagg aactattcat ctttctcacg | 420 |
| gaaataactg agatcaccat tccatgccga gtaacagacc cacagctggt ggtgacactg | 480 |
| cacgagaaga aggggacgt tgcactgcct gtcccctatg atcaccaacg tggcttttct | 540 |
| ggtatctttg aggacagaag ctacatctgc aaaaccacca ttggggacag ggaggtggat | 600 |
| tctgatgcct actatgtcta cagactccag gtgtcatcca tcaacgtctc tgtgaacgca | 660 |
| gtgcagactg tggtccgcca gggtgagaac atcccctca tgtgcattgt gatcgggaat | 720 |
| gaggtggtca cttcgagtg acataccccc gcaaagaaa gtgggcggct ggtggagccg | 780 |
| gtgactgact tcctcttgga tatgccttac acatccgct ccatcctgca catccccagt | 840 |
| gccgagttag aagactcggg gacctacacc tgcaatgtga cggagagtgt gaatgaccat | 900 |
| caggatgaaa aggccatcaa catcaccgtg gttgagagcg gctacgtgcg gctcctggga | 960 |
| gaggtgggca cactacaatt tgctgagctg catcggagcc ggacactgca ggtagtgttc | 1020 |
| gaggcctacc caccgcccac tgtcctgtgg ttcaaagaca accgcaccct gggcgactcc | 1080 |
| agcgctggcg aaatcgccct gtccacgcgc aacgtgtcgg agacccggta tgtgtcagag | 1140 |
| ctgacactgg ttcgcgtgaa ggtggcagag gctggccact acaccatgcg ggccttccat | 1200 |
| gaggatgctg aggtccagct ctccttccag ctacagatca atgtccctgt ccgagtgctg | 1260 |
| gagctaagtg agagccaccc tgacagtggg gaacagacag tccgctgtcg tggccggggc | 1320 |
| atgcccagc gaacatcat ctggtctgcc tgcagagacc tcaaaaggtg tccacgtgag | 1380 |
| ctgccgccca cgctgctggg gaacagttcc gaagaggaga gccagctgga gactaacgtg | 1440 |
| acgtactggg aggaggagca ggagtttgag gtggtgagca cactgcgtct gcagcacgtg | 1500 |
| gatcggccac tgtcggtgcg ctgcacgctg cgcaacgctg tgggccagga cacgcaggag | 1560 |
| gtcatcgtgg tgccacactc cttgcccttt aaggtggtgg tgatctcagc catcctggcc | 1620 |
| ctggtggtgc tcaccatcat ctcccttatc atcctcatca tgctttggca agaagagcca | 1680 |
| cgttacgaga tccgatggaa ggtgattgag tctgtgagct ctgacggcca tgagtacatc | 1740 |
| tacgtggacc ccatgcagct gccctatgac tccacgtggg agctgccgcg ggaccagctt | 1800 |
| gtgctgggac gcaccctcgg ctctggggcc tttgggcagg tggtggaggc cacggctcat | 1860 |
| ggcctgagcc attctcaggc cacgatgaaa gtggccgtca agatgcttaa atccacagcc | 1920 |
| cgcagcagtg agaagcaagc ccttatgtcg gagctgaaga tcatgagtca ccttgggccc | 1980 |
| cacctgaacg tggtcaacct gttgggggcc tgcaccaaag aggaccccat ctatatcatc | 2040 |
| actgagtact gccgctacgg agacctggtg gactacctgc accgcaacaa acacaccttc | 2100 |
| ctgcagcacc actccgacaa gcgccgcccg cccagcgcgg agctctacag caatgctctg | 2160 |

-continued

```
cccgttgggc tccccctgcc cagccatgtg tccttgaccg ggagagcga cggtggctac    2220 atggacatga gcaaggacga gtcggtggac tatgtgccca tgctggacat gaaaggagac    2280
gtcaaatatg cagacatcga gtcctccaac tacatggccc cttacgataa ctacgttccc    2340 tctgccctg agaggacctg ccgagcaact ttgatcaacg agtctccagt gctaagctac    2400
atggacctcg tgggcttcag ctaccaggtg gccaatggca tggagtttct ggcctccaag    2460
aactgcgtcc acagagacct ggcggctagg aacgtgctca tctgtgaagg caagctggtc    2520
aagatctgtg actttggcct ggctcgagac atcatgcggg actcgaatta catctccaaa    2580
ggcagcacct ttttgccttt aaagtggatg gctccggaga gcatcttcaa cagcctctac    2640
accaccctga gcgacgtgtg gtccttcggg atcctgctct gggagatctt caccttgggt    2700 ggcaccccctt acccagagct gcccatgaac gagcagttct acaatgccat caaacggggt    2760
taccgcatgg cccagcctgc ccatgcctcc gacgagatct atgagatcat gcagaagtgc    2820
tgggaagaga gtttgagat cggcccccc ttctcccagc tggtgctgct tctcgagaga    2880
ctgttgggcg aaggttacaa aaagaagtac cagcaggtgg atgaggagtt tctgaggagt    2940
gaccacccag ccatccttcg gtcccaggcc cgcttgcctg ggttccatgg cctccgatct    3000 ccctggaca ccagctccgt cctctatact gccgtgcagc caatgagggg tgacaacgac    3060
tatatcatcc ccctgcctga ccccaaaccc gaggttgctg acgagggccc actgagggt    3120 tcccccagcc tagccagctc caccctgaat gaagtcaaca cctcctcaac catctcctgt    3180 gacagcccc tggagcccca ggacgaacca gagccagagc cccagcttga gctccaggtg    3240
gagccggagc cagagctgga acagttgccg gattcggggt gccctgcgcc tcgggcggaa    3300
gcagaggata gcttcctgta g                                              3321
```

<210> SEQ ID NO 20
<211> LENGTH: 117
<212> TYPE: DNA
<213> ORGANISM: Artificial Sequence
<220> FEATURE:
<223> OTHER INFORMATION: LDLR-3 cDNA

<400> SEQUENCE: 20

```
cccccaaga cgtgctccca ggacgagttt cgctgccacg atgggaagtg catctctcgg    60
cagttcgtct gtgactcaga ccgggactgc ttggacggct cagacgaggc ctcctgc      117
```

<210> SEQ ID NO 21
<211> LENGTH: 39
<212> TYPE: PRT
<213> ORGANISM: Artificial Sequence
<220> FEATURE:
<223> OTHER INFORMATION: LDLR-3 polypeptide

<400> SEQUENCE: 21

```
Pro Pro Lys Thr Cys Ser Gln Asp Glu Phe Arg Cys His Asp Gly Lys
1               5                   10                  15

Cys Ile Ser Arg Gln Phe Val Cys Asp Ser Asp Arg Asp Cys Leu Asp
            20                  25                  30

Gly Ser Asp Glu Ala Ser Cys
        35
```

<210> SEQ ID NO 22
<211> LENGTH: 42
<212> TYPE: DNA
<213> ORGANISM: Artificial Sequence

```
<220> FEATURE:
<223> OTHER INFORMATION: (KLAKLAK)2 cDNA

<400> SEQUENCE: 22
aaactggcga aactggcgaa aaaactggcg aaactggcga aa                              42

<210> SEQ ID NO 23
<211> LENGTH: 14
<212> TYPE: PRT
<213> ORGANISM: Artificial Sequence
<220> FEATURE:
<223> OTHER INFORMATION: KLAKLAK)2 - polypeptide sequence

<400> SEQUENCE: 23

Lys Leu Ala Lys Leu Ala Lys Lys Leu Ala Lys Leu Ala Lys
1               5                   10

<210> SEQ ID NO 24
<211> LENGTH: 39
<212> TYPE: DNA
<213> ORGANISM: Artificial Sequence
<220> FEATURE:
<223> OTHER INFORMATION: cDNA Hexokinase inhibitor

<400> SEQUENCE: 24
tcctccgtgc gttggtggtc cgatgatgaa tggcgtatg                                  39

<210> SEQ ID NO 25
<211> LENGTH: 13
<212> TYPE: PRT
<213> ORGANISM: Artificial Sequence
<220> FEATURE:
<223> OTHER INFORMATION: polypeptide hexokinase inhibitor

<400> SEQUENCE: 25

Ser Ser Val Arg Trp Trp Ser Asp Asp Glu Trp Arg Met
1               5                   10

<210> SEQ ID NO 26
<211> LENGTH: 36
<212> TYPE: DNA
<213> ORGANISM: Artificial Sequence
<220> FEATURE:
<223> OTHER INFORMATION: cDNA phosphoglycerate mutase inhibitor

<400> SEQUENCE: 26
aaactggtgc tgatccggca cggcgagagc gcatgg                                     36

<210> SEQ ID NO 27
<211> LENGTH: 12
<212> TYPE: PRT
<213> ORGANISM: Artificial Sequence
<220> FEATURE:
<223> OTHER INFORMATION: polypeptide phosphoglycerate mutase inhibitor

<400> SEQUENCE: 27

Lys Leu Val Leu Ile Arg His Gly Glu Ser Ala Trp
1               5                   10

<210> SEQ ID NO 28
<211> LENGTH: 18
<212> TYPE: DNA
<213> ORGANISM: Artificial Sequence
<220> FEATURE:
<223> OTHER INFORMATION: phosphofructokinase inhibitor cDNA

<400> SEQUENCE: 28
```
tccctgaaag tgtggacc                                                    18

<210> SEQ ID NO 29
<211> LENGTH: 6
<212> TYPE: PRT
<213> ORGANISM: Artificial Sequence
<220> FEATURE:
<223> OTHER INFORMATION: phosphofructokinase inhibitor polypeptide

<400> SEQUENCE: 29

Ser Leu Lys Val Trp Thr
1               5

<210> SEQ ID NO 30
<211> LENGTH: 792
<212> TYPE: DNA
<213> ORGANISM: Artificial Sequence
<220> FEATURE:
<223> OTHER INFORMATION: KLAK-ELP cDNA

<400> SEQUENCE: 30
aaactggcga aactggcgaa aaaactggcg aaactggcga agttccgggg cgtaggtgtc        60
ccaggtgtgg gcgtaccggg cgttggtgtt cctggtgtcg gcgtgccggg cgtgggtgtt      120
ccgggcgtag gtgtcccagg tgtgggcgta ccgggcgttg gtgttcctgg tgtcggcgtg      180
ccgggcgtgg gtgttccggg cgtaggtgtc ccaggtgtgg gcgtaccggg cgttggtgtt      240
cctggtgtcg gcgtgccggg cgtgggtgtt ccgggcgtag gtgtcccagg tgtgggcgta      300
ccgggcgttg gtgttcctgg tgtcggcgtg ccgggcgtgg gtgttccggg cgtaggtgtc      360
ccaggtgtgg gcgtaccggg cgttggtgtt cctggtgtcg gcgtgccggg cgtgggtgtt      420
ccgggcgtag gtgtcccagg tgtgggcgta ccgggcgttg gtgttcctgg tgtcggcgtg      480
ccgggcgtgg gtgttccggg cgtaggtgtc ccaggtgtgg gcgtaccggg cgttggtgtt      540
cctggtgtcg gcgtgccggg cgtgggtgtt ccgggcgtag gtgtcccagg tgtgggcgta      600
ccgggcgttg gtgttcctgg tgtcggcgtg ccgggcgtgg gtgttccggg cgtaggtgtc      660
ccaggtgtgg gcgtaccggg ctgcggtgtt cctggtgtcg gcgtgccggg cgtgggtgtt      720
ccgggcgtag gtgtcccagg tgtgggcgta ccgggctgcg gtgttcctgg tgtcggcgtg      780
ccgggcgtgg gt                                                          792

<210> SEQ ID NO 31
<211> LENGTH: 264
<212> TYPE: PRT
<213> ORGANISM: Artificial Sequence
<220> FEATURE:
<223> OTHER INFORMATION: KLAK-ELP polypeptide

<400> SEQUENCE: 31

Lys Leu Ala Lys Leu Ala Lys Lys Leu Ala Lys Leu Ala Lys Val Pro
1               5                   10                  15

Gly Val Gly Val Pro Gly Val Gly Val Pro Gly Val Gly Val Pro Gly
                20                  25                  30

Val Gly Val Pro Gly Val Gly Val Pro Gly Val Gly Val Pro Gly Val
            35                  40                  45

Gly Val Pro Gly Val Gly Val Pro Gly Val Gly Val Pro Gly Val Gly
        50                  55                  60

Val Pro Gly Val Gly Val Pro Gly Val Gly Val Pro Gly Val Gly Val
65                  70                  75                  80

```
Pro Gly Val Gly Val Pro Gly Val Gly Val Pro Gly Val Gly Val Pro
                 85                  90                  95
Gly Val Gly Val Pro Gly Val Gly Val Pro Gly Val Gly Val Pro Gly
            100                 105                 110
Val Gly Val Pro Gly Val Gly Val Pro Gly Val Gly Val Pro Gly Val
        115                 120                 125
Gly Val Pro Gly Val Gly Val Pro Gly Val Gly Val Pro Gly Val Gly
    130                 135                 140
Val Pro Gly Val Gly Val Pro Gly Val Gly Val Pro Gly Val Gly Val
145                 150                 155                 160
Pro Gly Val Gly Val Pro Gly Val Gly Val Pro Gly Val Gly Val Pro
                165                 170                 175
Gly Val Gly Val Pro Gly Val Gly Val Pro Gly Val Gly Val Pro Gly
            180                 185                 190
Val Gly Val Pro Gly Val Gly Val Pro Gly Val Gly Val Pro Gly Val
        195                 200                 205
Gly Val Pro Gly Val Gly Val Pro Gly Val Gly Val Pro Gly Val Gly
    210                 215                 220
Val Pro Gly Cys Gly Val Pro Gly Val Gly Val Pro Gly Val Gly Val
225                 230                 235                 240
Pro Gly Val Gly Val Pro Gly Val Gly Val Pro Gly Cys Gly Val Pro
                245                 250                 255
Gly Val Gly Val Pro Gly Val Gly
            260
```

<210> SEQ ID NO 32
<211> LENGTH: 1332
<212> TYPE: DNA
<213> ORGANISM: Artificial Sequence
<220> FEATURE:
<223> OTHER INFORMATION: KGF-ELP cDNA

<400> SEQUENCE: 32

```
atgcacaaat ggatactgac atggatcctg ccaactttgc tctacagatc atgctttcac      60
attatctgtc tagtgggtac tatatcttta gcttgcaatg acatgactcc agagcaaatg     120
gctacaaatg tgaactgttc cagccctgag cgacacacaa gaagttatga ttacatggaa     180
ggaggggata taagagtgag aagactcttc tgtcgaacac agtggtacct gaggatcgat     240
aaaagaggca agtaaaagg gacccaagag atgaagaata attacaatat catggaaatc     300
aggacagtgg cagttggaat tgtggcaatc aaaggggtgg aaagtgaatt ctatcttgca     360
atgaacaagg aaggaaaact ctatgcaaag aaagaatgca atgaagattg taacttcaaa     420
gaactaattc tggaaaacca ttacaacaca tatgcatcag ctaaatggac acacaacgga     480
ggggaaatgt ttgttgcctt aaatcaaaag gggattcctg taagaggaaa aaaaacgaag     540
aaagaacaaa aaacagccca ctttcttcct atggcaataa ctgttccggg cgtaggtgtc     600
ccaggtgtgg gcgtaccggg cgttggtgtt cctggtgtcg gcgtgccggg cgtgggtgtt     660
ccgggcgtag gtgtcccagg tgtgggcgta ccggcgttg gtgttcctgg tgtcggcgtg     720
ccgggcgtgg ggtgttccgggc gtaggtgtc caggtgtgg gcgtaccggg cgttggtgtt     780
cctggtgtcg gcgtgccggg cgtgggtgtt ccgggcgtag gtgtcccagg tgtgggcgta     840
ccggcgttg gtgttcctgg tgtcggcgtg ccgggcgtgg gtgttccggg cgtaggtgtc     900
ccaggtgtgg gcgtaccggg cgttggtgtt cctggtgtcg gcgtgccggg cgtgggtgtt     960
ccgggcgtag gtgtcccagg tgtgggcgta ccggcgttg gtgttcctgg tgtcggcgtg    1020
```

-continued

```
ccgggcgtgg gtgttccggg cgtaggtgtc ccaggtgtgg gcgtaccggg cgttggtgtt    1080
cctggtgtcg gcgtgccggg cgtgggtgtt ccgggcgtag gtgtcccagg tgtgggcgta    1140
ccgggcgttg gtgttcctgg tgtcggcgtg ccgggcgtgg gtgttccggg cgtaggtgtc    1200
ccaggtgtgg gcgtaccggg ctgcggtgtt cctggtgtcg gcgtgccggg cgtgggtgtt    1260
ccgggcgtag gtgtcccagg tgtgggcgta ccgggctgcg gtgttcctgg tgtcggcgtg    1320
ccgggcgtgg gt                                                       1332
```

<210> SEQ ID NO 33
<211> LENGTH: 444
<212> TYPE: PRT
<213> ORGANISM: Artificial Sequence
<220> FEATURE:
<223> OTHER INFORMATION: KGF-ELP polypeptide

<400> SEQUENCE: 33

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr Val Pro Gly Val Gly Val Pro Gly Val Gly Val Pro Gly Val
        195                 200                 205

Gly Val Pro Gly Val Gly Val Pro Gly Val Gly Val Pro Gly Val Gly
    210                 215                 220

Val Pro Gly Val Gly Val Pro Gly Val Gly Val Pro Gly Val Gly Val
225                 230                 235                 240

Pro Gly Val Gly Val Pro Gly Val Gly Val Pro Gly Val Gly Val Pro
                245                 250                 255

Gly Val Gly Val Pro Gly Val Gly Val Pro Gly Val Gly Val Pro Gly
            260                 265                 270

Val Gly Val Pro Gly Val Gly Val Pro Gly Val Gly Val Pro Gly Val
        275                 280                 285

Gly Val Pro Gly Val Gly Val Pro Gly Val Gly Val Pro Gly Val Gly
    290                 295                 300
```

Val Pro Gly Val Gly Val Pro Gly Val Gly Val Pro Gly Val Gly Val
305                 310                 315                 320

Pro Gly Val Gly Val Pro Gly Val Gly Val Pro Gly Val Gly Val Pro
            325                 330                 335

Gly Val Gly Val Pro Gly Val Gly Val Pro Gly Val Gly Val Pro Gly
        340                 345                 350

Val Gly Val Pro Gly Val Gly Val Pro Gly Val Gly Val Pro Gly Val
    355                 360                 365

Gly Val Pro Gly Val Gly Val Pro Gly Val Gly Val Pro Gly Val Gly
370                 375                 380

Val Pro Gly Val Gly Val Pro Gly Val Gly Val Pro Gly Val Gly Val
385                 390                 395                 400

Pro Gly Val Gly Val Pro Gly Cys Gly Val Pro Gly Val Gly Val Pro
            405                 410                 415

Gly Val Gly Val Pro Gly Val Gly Val Pro Gly Val Gly Val Pro Gly
        420                 425                 430

Cys Gly Val Pro Gly Val Gly Val Pro Gly Val Gly
        435                 440

<210> SEQ ID NO 34
<211> LENGTH: 909
<212> TYPE: DNA
<213> ORGANISM: Artificial Sequence
<220> FEATURE:
<223> OTHER INFORMATION: EGF-ELP cDNA

<400> SEQUENCE: 34

```
aatagtgact ctgaatgtcc cctgtcccac gatgggtact gcctccatga tggtgtgtgc      60
atgtatattg aagcattgga caagtatgca tgcaactgtg ttgttggcta catcggggag     120
cgatgtcagt accgagacct gaagtggtgg gaactgcgcg ttccgggcgt aggtgtccca     180
ggtgtgggcg taccgggcgt tggtgttcct ggtgtcggcg tgccgggcgt gggtgttccg     240
ggcgtaggtg tcccaggtgt gggcgtaccg ggcgttggtg ttcctggtgt cggcgtgccg     300
ggcgtgggtg ttccgggcgt aggtgtccca ggtgtgggcg taccgggcgt tggtgttcct     360
ggtgtcggcg tgccgggcgt gggtgttccg ggcgtaggtg tcccaggtgt gggcgtaccg     420
ggcgttggtg ttcctggtgt cggcgtgccg ggcgtgggtg ttccgggcgt aggtgtccca     480
ggtgtgggcg taccgggcgt tggtgttcct ggtgtcggcg tgccgggcgt gggtgttccg     540
ggcgtaggtg tcccaggtgt gggcgtaccg ggcgttggtg ttcctggtgt cggcgtgccg     600
ggcgtgggtg ttccgggcgt aggtgtccca ggtgtgggcg taccgggcgt tggtgttcct     660
ggtgtcggcg tgccgggcgt gggtgttccg ggcgtaggtg tcccaggtgt gggcgtaccg     720
ggcgttggtg ttcctggtgt cggcgtgccg ggcgtgggtg ttccgggcgt aggtgtccca     780
ggtgtgggcg taccgggctg cggtgttcct ggtgtcggcg tgccgggcgt gggtgttccg     840
ggcgtaggtg tcccaggtgt gggcgtaccg ggctgcggtg ttcctggtgt cggcgtgccg     900
ggcgtgggt                                                             909
```

<210> SEQ ID NO 35
<211> LENGTH: 303
<212> TYPE: PRT
<213> ORGANISM: Artificial Sequence
<220> FEATURE:
<223> OTHER INFORMATION: EGF-ELP polypeptide

<400> SEQUENCE: 35

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Val Pro Gly Val Gly Val Pro Gly Val Gly Val
50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Cys Gly Val Pro Gly Val
            260                 265                 270

Gly Val Pro Gly Val Gly Val Pro Gly Val Gly Val Pro Gly Val Gly
        275                 280                 285

Val Pro Gly Cys Gly Val Pro Gly Val Gly Val Pro Gly Val Gly
    290                 295                 300

<210> SEQ ID NO 36
<211> LENGTH: 2700
<212> TYPE: DNA
<213> ORGANISM: Artificial Sequence
<220> FEATURE:
<223> OTHER INFORMATION: ELP V180 cDNA

<400> SEQUENCE: 36
gttccgggcg taggtgtccc aggtgtgggc gtaccgggcg ttggtgttcc tggtgtcggc      60
gtgccgggcg tggtgttcc gggcgtaggt gtcccaggtg tgggcgtacc gggcgttggt     120
gttcctggtg tcggcgtgcc gggcgtgggt gttccgggcg taggtgtccc aggtgtgggc     180
gtaccgggcg ttggtgttcc tggtgtcggc gtgccgggcg tggtgttcc gggcgtaggt     240 gtcccaggtg tgggcgtacc gggcgttggt gttcctggtg tcggcgtgcc gggcgtgggt     300
gttccgggcg taggtgtccc aggtgtgggc gtaccgggcg ttggtgttcc tggtgtcggc     360
```

```
gtgccgggcg tgggtgttcc gggcgtaggt gtcccaggtg tgggcgtacc gggcgttggt      420
gttcctggtg tcggcgtgcc gggcgtgggt gttccgggcg taggtgtccc aggtgtgggc      480
gtaccgggcg ttggtgttcc tggtgtcggc gtgccgggcg tgggtgttcc gggcgtaggt      540
gtcccaggtg tgggcgtacc gggcgttggt gttcctggtg tcggcgtgcc gggcgtgggt      600
gttccgggcg taggtgtccc aggtgtgggc gtaccgggcg ttggtgttcc tggtgtcggc      660
gtgccgggcg tgggtgttcc gggcgtaggt gtcccaggtg tgggcgtacc gggcgttggt      720
gttcctggtg tcggcgtgcc gggcgtgggt gttccgggcg taggtgtccc aggtgtgggc      780
gtaccgggcg ttggtgttcc tggtgtcggc gtgccgggcg tgggtgttcc gggcgtaggt      840
gtcccaggtg tgggcgtacc gggcgttggt gttcctggtg tcggcgtgcc gggcgtgggt      900
gttccgggcg taggtgtccc aggtgtgggc gtaccgggcg ttggtgttcc tggtgtcggc      960
gtgccgggcg tgggtgttcc gggcgtaggt gtcccaggtg tgggcgtacc gggcgttggt     1020
gttcctggtg tcggcgtgcc gggcgtgggt gttccgggcg taggtgtccc aggtgtgggc     1080
gtaccgggcg ttggtgttcc tggtgtcggc gtgccgggcg tgggtgttcc gggcgtaggt     1140
gtcccaggtg tgggcgtacc gggcgttggt gttcctggtg tcggcgtgcc gggcgtgggt     1200
gttccgggcg taggtgtccc aggtgtgggc gtaccgggcg ttggtgttcc tggtgtcggc     1260
gtgccgggcg tgggtgttcc gggcgtaggt gtcccaggtg tgggcgtacc gggcgttggt     1320
gttcctggtg tcggcgtgcc gggcgtgggt gttccgggcg taggtgtccc aggtgtgggc     1380
gtaccgggcg ttggtgttcc tggtgtcggc gtgccgggcg tgggtgttcc gggcgtaggt     1440
gtcccaggtg tgggcgtacc gggcgttggt gttcctggtg tcggcgtgcc gggcgtgggt     1500
gttccgggcg taggtgtccc aggtgtgggc gtaccgggcg ttggtgttcc tggtgtcggc     1560
gtgccgggcg tgggtgttcc gggcgtaggt gtcccaggtg tgggcgtacc gggcgttggt     1620
gttcctggtg tcggcgtgcc gggcgtgggt gttccgggcg taggtgtccc aggtgtgggc     1680
gtaccgggcg ttggtgttcc tggtgtcggc gtgccgggcg tgggtgttcc gggcgtaggt     1740
gtcccaggtg tgggcgtacc gggcgttggt gttcctggtg tcggcgtgcc gggcgtgggt     1800
gttccgggcg taggtgtccc aggtgtgggc gtaccgggcg ttggtgttcc tggtgtcggc     1860
gtgccgggcg tgggtgttcc gggcgtaggt gtcccaggtg tgggcgtacc gggcgttggt     1920
gttcctggtg tcggcgtgcc gggcgtgggt gttccgggcg taggtgtccc aggtgtgggc     1980
gtaccgggcg ttggtgttcc tggtgtcggc gtgccgggcg tgggtgttcc gggcgtaggt     2040
gtcccaggtg tgggcgtacc gggcgttggt gttcctggtg tcggcgtgcc gggcgtgggt     2100
gttccgggcg taggtgtccc aggtgtgggc gtaccgggcg ttggtgttcc tggtgtcggc     2160
gtgccgggcg tgggtgttcc gggcgtaggt gtcccaggtg tgggcgtacc gggcgttggt     2220
gttcctggtg tcggcgtgcc gggcgtgggt gttccgggcg taggtgtccc aggtgtgggc     2280
gtaccgggcg ttggtgttcc tggtgtcggc gtgccgggcg tgggtgttcc gggcgtaggt     2340
gtcccaggtg tgggcgtacc gggcgttggt gttcctggtg tcggcgtgcc gggcgtgggt     2400
gttccgggcg taggtgtccc aggtgtgggc gtaccgggcg ttggtgttcc tggtgtcggc     2460
gtgccgggcg tgggtgttcc gggcgtaggt gtcccaggtg tgggcgtacc gggcgttggt     2520
gttcctggtg tcggcgtgcc gggcgtgggt gttccgggcg taggtgtccc aggtgtgggc     2580
gtaccgggcg ttggtgttcc tggtgtcggc gtgccgggcg tgggtgttcc gggcgtaggt     2640
gtcccaggtg tgggcgtacc gggcgttggt gttcctggtg tcggcgtgcc gggcgtgggt     2700
```

<210> SEQ ID NO 37
<211> LENGTH: 900
<212> TYPE: PRT
<213> ORGANISM: Artificial Sequence
<220> FEATURE:
<223> OTHER INFORMATION: ELP V180 polypeptide

<400> SEQUENCE: 37

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Val Gly Val Pro Gly Val Gly Val Pro Gly Val Gly Val Pro
            260                 265                 270

Gly Val Gly Val Pro Gly Val Gly Val Pro Gly Val Gly Val Pro Gly
        275                 280                 285

Val Gly Val Pro Gly Val Gly Val Pro Gly Val Gly Val Pro Gly Val
    290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
        355                 360                 365
```

```
Val Gly Val Pro Gly Val Gly Val Pro Gly Val
    370             375             380

Gly Val Pro Gly Val Gly Val Pro Gly Val Gly Val
385             390             395             400

Val Pro Gly Val Gly Val Pro Gly Val Gly Val
            405             410             415

Pro Gly Val Gly Val Pro Gly Val Gly Val Pro
            420             425             430

Gly Val Gly Val Pro Gly Val Gly Val Pro Gly
        435             440             445

Val Gly Val Pro Gly Val Gly Val Pro Gly Val
    450             455             460

Gly Val Pro Gly Val Gly Val Pro Gly Val Gly
465             470             475             480

Val Pro Gly Val Gly Val Pro Gly Val Gly Val
            485             490             495

Pro Gly Val Gly Val Pro Gly Val Gly Val Pro
            500             505             510

Gly Val Gly Val Pro Gly Val Gly Val Pro Gly
        515             520             525

Val Gly Val Pro Gly Val Gly Val Pro Gly Val
    530             535             540

Gly Val Pro Gly Val Gly Val Pro Gly Val Gly
545             550             555             560

Val Pro Gly Val Gly Val Pro Gly Val Gly Val
            565             570             575

Pro Gly Val Gly Val Pro Gly Val Gly Val Pro
            580             585             590

Gly Val Gly Val Pro Gly Val Gly Val Pro Gly
        595             600             605

Val Gly Val Pro Gly Val Gly Val Pro Gly Val
    610             615             620

Gly Val Pro Gly Val Gly Val Pro Gly Val Gly
625             630             635             640

Val Pro Gly Val Gly Val Pro Gly Val Gly Val
            645             650             655

Pro Gly Val Gly Val Pro Gly Val Gly Val Pro
            660             665             670

Gly Val Gly Val Pro Gly Val Gly Val Pro Gly
        675             680             685

Val Gly Val Pro Gly Val Gly Val Pro Gly Val
    690             695             700

Gly Val Pro Gly Val Gly Val Pro Gly Val Gly
705             710             715             720

Val Pro Gly Val Gly Val Pro Gly Val Gly Val
            725             730             735

Pro Gly Val Gly Val Pro Gly Val Gly Val Pro
            740             745             750

Gly Val Gly Val Pro Gly Val Gly Val Pro Gly
        755             760             765

Val Gly Val Pro Gly Val Gly Val Pro Gly Val
    770             775             780

Gly Val Pro Gly Val Gly Val Pro Gly Val Gly
```

```
                      785                 790                 795                 800
Val Pro Gly Val Gly Val Pro Gly Val Gly Val Pro Gly Val Gly Val
                        805                 810                 815
Pro Gly Val Gly Val Pro Gly Val Gly Val Pro Gly Val Gly Val Pro
                820                 825                 830
Gly Val Gly Val Pro Gly Val Gly Val Pro Gly Val Gly Val Pro Gly
            835                 840                 845
Val Gly Val Pro Gly Val Gly Val Pro Gly Val Gly Val Pro Gly Val
        850                 855                 860
Gly Val Pro Gly Val Gly Val Pro Gly Val Gly Val Pro Gly Val Gly
865                 870                 875                 880
Val Pro Gly Val Gly Val Pro Gly Val Gly Val Pro Gly Val Gly Val
                    885                 890                 895
Pro Gly Val Gly
            900

<210> SEQ ID NO 38
<211> LENGTH: 1800
<212> TYPE: DNA
<213> ORGANISM: Artificial Sequence
<220> FEATURE:
<223> OTHER INFORMATION: ELP V120 cDNA

<400> SEQUENCE: 38
```

| | | | | | |
|---|---|---|---|---|---|
| gttccgggcg | taggtgtccc | aggtgtgggc | gtaccgggcg | ttggtgttcc | tggtgtcggc | 60 |
| gtgccgggcg | tgggtgttcc | gggcgtaggt | gtcccaggtg | tgggcgtacc | gggcgttggt | 120 |
| gttcctggtg | tcggcgtgcc | gggcgtgggt | gttccgggcg | taggtgtccc | aggtgtgggc | 180 |
| gtaccgggcg | ttggtgttcc | tggtgtcggc | gtgccgggcg | tgggtgttcc | gggcgtaggt | 240 |
| gtcccaggtg | tgggcgtacc | gggcgttggt | gttcctggtg | tcggcgtgcc | gggcgtgggt | 300 |
| gttccgggcg | taggtgtccc | aggtgtgggc | gtaccgggcg | ttggtgttcc | tggtgtcggc | 360 |
| gtgccgggcg | tgggtgttcc | gggcgtaggt | gtcccaggtg | tgggcgtacc | gggcgttggt | 420 |
| gttcctggtg | tcggcgtgcc | gggcgtgggt | gttccgggcg | taggtgtccc | aggtgtgggc | 480 |
| gtaccgggcg | ttggtgttcc | tggtgtcggc | gtgccgggcg | tgggtgttcc | gggcgtaggt | 540 |
| gtcccaggtg | tgggcgtacc | gggcgttggt | gttcctggtg | tcggcgtgcc | gggcgtgggt | 600 |
| gttccgggcg | taggtgtccc | aggtgtgggc | gtaccgggcg | ttggtgttcc | tggtgtcggc | 660 |
| gtgccgggcg | tgggtgttcc | gggcgtaggt | gtcccaggtg | tgggcgtacc | gggcgttggt | 720 |
| gttcctggtg | tcggcgtgcc | gggcgtgggt | gttccgggcg | taggtgtccc | aggtgtgggc | 780 |
| gtaccgggcg | ttggtgttcc | tggtgtcggc | gtgccgggcg | tgggtgttcc | gggcgtaggt | 840 |
| gtcccaggtg | tgggcgtacc | gggcgttggt | gttcctggtg | tcggcgtgcc | gggcgtgggt | 900 |
| gttccgggcg | taggtgtccc | aggtgtgggc | gtaccgggcg | ttggtgttcc | tggtgtcggc | 960 |
| gtgccgggcg | tgggtgttcc | gggcgtaggt | gtcccaggtg | tgggcgtacc | gggcgttggt | 1020 |
| gttcctggtg | tcggcgtgcc | gggcgtgggt | gttccgggcg | taggtgtccc | aggtgtgggc | 1080 |
| gtaccgggcg | ttggtgttcc | tggtgtcggc | gtgccgggcg | tgggtgttcc | gggcgtaggt | 1140 |
| gtcccaggtg | tgggcgtacc | gggcgttggt | gttcctggtg | tcggcgtgcc | gggcgtgggt | 1200 |
| gttccgggcg | taggtgtccc | aggtgtgggc | gtaccgggcg | ttggtgttcc | tggtgtcggc | 1260 |
| gtgccgggcg | tgggtgttcc | gggcgtaggt | gtcccaggtg | tgggcgtacc | gggcgttggt | 1320 |
| gttcctggtg | tcggcgtgcc | gggcgtgggt | gttccgggcg | taggtgtccc | aggtgtgggc | 1380 |

```
gtaccgggcg ttggtgttcc tggtgtcggc gtgccgggcg tgggtgttcc gggcgtaggt    1440
gtcccaggtg tgggcgtacc gggcgttggt gttcctggtg tcggcgtgcc gggcgtgggt    1500
gttccgggcg taggtgtccc aggtgtgggc gtaccgggcg ttggtgttcc tggtgtcggc    1560
gtgccgggcg tgggtgttcc gggcgtaggt gtcccaggtg tgggcgtacc gggcgttggt    1620
gttcctggtg tcggcgtgcc gggcgtgggt gttccgggcg taggtgtccc aggtgtgggc    1680
gtaccgggcg ttggtgttcc tggtgtcggc gtgccgggcg tgggtgttcc gggcgtaggt    1740
gtcccaggtg tgggcgtacc gggcgttggt gttcctggtg tcggcgtgcc gggcgtgggt    1800
```

<210> SEQ ID NO 39
<211> LENGTH: 25
<212> TYPE: DNA
<213> ORGANISM: Artificial Sequence
<220> FEATURE:
<223> OTHER INFORMATION: KGFRiiib forward primer (for all cell lines
      tested except fibroblasts)

<400> SEQUENCE: 39
caattatata gggcaggcca accag                                            25

<210> SEQ ID NO 40
<211> LENGTH: 25
<212> TYPE: DNA
<213> ORGANISM: Artificial Sequence
<220> FEATURE:
<223> OTHER INFORMATION: KGFRiiic forward primer (for fibroblasts)

<400> SEQUENCE: 40
cttggcgggt aattctattg ggata                                            25

<210> SEQ ID NO 41
<211> LENGTH: 25
<212> TYPE: DNA
<213> ORGANISM: Artificial Sequence
<220> FEATURE:
<223> OTHER INFORMATION: KGFRiiib and iiic reverse primer

<400> SEQUENCE: 41
aagaagaccc ctatgcagta aatgg                                            25

CARGO CARRYING NANOPARTICLES

CROSS-REFERENCE TO RELATED APPLICATIONS

This application claims the benefit of U.S. provisional application Ser. No. 61/882,892 filed on Sep. 26, 2013, having the title "A Platform for Selective Intracellular Delivery by the Growth Factor Mediated Macropinocytosis Pathway," the disclosure of which is incorporated by reference herein in its entirety. This application also claims the benefit of U.S. provisional application Ser. No. 61/884,417 filed on Sep. 30, 2013, having the title "Targeted Enhancement of Macropinocytosis for the Intracellular Delivery of Lytic Peptides to Lung Tumors," the disclosure of which is incorporated by reference herein in its entirety.

SEQUENCE LISTING

This application contains a sequence listing filed in electronic form as an ASCII.txt file entitled 02086823.txt, created on Sep. 26, 2014 and having a size of 68,500 bytes. The content of the sequence listing is incorporated herein in its entirety.

BACKGROUND

According to the Centers for Disease Control and Prevention (CDC), more than 1 million people are diagnosed with cancer and about a half million people will die from cancer in the United States each year. About half of all men and one-third of all women will develop cancer during their lifetime. According to the American Cancer Society, there are about 14.5 million people living in the United States that have had or currently suffer from cancer. Current traditional treatments include surgery, chemotherapy, and radiation. A person with cancer may have any or all of these treatments. Traditional chemotherapy treatments can have deleterious side effects which often lead to their intolerance by patients. These side effects are mainly due to the toxicity of the chemotherapy treatments and their systemic effects. Further, many current chemotherapy treatments become ineffective after continued use as the cancer adapts and becomes resistant to the chemotherapy treatment. As such, there is an extended need for improved therapeutic treatments for cancer.

SUMMARY

Described herein are nanoparticles (referred to also herein as cargo carrying nanoparticles) containing a first fusion polypeptide containing a first elastin-like peptide (ELP) and a targeting moiety configured to specifically bind a binding partner, where the targeting moiety induces macropinocytosis when the targeting moiety specifically binds to the binding partner, and where the first ELP is operatively linked to the targeting moiety and a second fusion polypeptide containing a second ELP and a first cargo molecule, where the second ELP is operatively linked to the first cargo molecule, where the nanoparticle self assembles at a temperature that is greater than a phase transition temperature.

In some aspects, the targeting moiety is selected from keratinocyte growth factor, epidermal growth factor, and platelet derived growth factor. In further aspects, the first cargo molecule is a lytic peptide or a glycolysis inhibitor. In other aspects, the nanoparticle further comprises a cargo binding peptide sequence, the cargo binding peptide sequence configured to deliver small molecules. In further aspects, the second cargo molecule is a lytic peptide or a glycolysis inhibitor. In some aspects, the binding partner is located on the surface of a cell. In some aspects the cell is a cancer cell. In further aspects, the binding partner is selected from keratinocyte growth receptor, epidermal growth factor receptor, and platelet derived growth factor. In some aspects, the phase transition temperature ranges from about 5° C. to about 40° C.

Also described herein are vectors containing a first nucleotide sequence encoding a first fusion polypeptide, where the first fusion polypeptide contains a first elastin-like peptide (ELP) operatively linked to a targeting moiety configured to specifically bind a binding partner, where the targeting moiety induces macropinocytosis when the targeting moiety specifically binds to the binding partner and a second nucleotide sequence encoding a second fusion polypeptide, where the second fusion polypeptide contains a second ELP operatively linked to a first cargo molecule, where the second nucleotide sequence is operatively linked to the first nucleotide sequence. In some aspects, the vector further contains a third nucleotide sequence encoding a third fusion polypeptide, where the third fusion polypeptide contains a third ELP fused to a second cargo molecule, wherein the third nucleotide sequence is operatively linked to the first nucleotide sequence or the second nucleotide sequence. In some aspects, the first cargo molecule is selected from keratinocyte growth factor, epidermal growth factor, and platelet derived growth factor. In further aspects, the he first cargo molecule is a mitochondrial lytic peptide or a glycolysis inhibitor.

Also described are pharmaceutical formulations containing an effective amount of a nanoparticle, the nanoparticle containing a first fusion polypeptide comprising a first elastin-like peptide (ELP) and a targeting moiety configured to specifically bind a binding partner, where the targeting moiety induces macropinocytosis when the targeting moiety specifically binds to the binding partner, and where the first ELP is operatively linked to the targeting moiety, and a second fusion polypeptide comprising a second ELP and a first cargo molecule, where the second ELP is operatively linked to the first cargo molecule, where the nanoparticle self assembles above a phase transition temperature; and a pharmaceutically acceptable carrier, where the nanoparticle self assembles at a temperature greater than a phase transition temperature. In other aspects, the pharmaceutical formulation contains a nanoparticle having third fusion polypeptide comprising a third ELP and a second cargo molecule, wherein the third ELP is operatively linked to the second cargo molecule. In additional aspects, the first cargo molecule is a mitochondrial lytic peptide and wherein the second cargo molecule is a glycolysis inhibitor. In further aspects the targeting moiety is a growth factor selected from keratinocyte growth factor, epidermal growth factor, and platelet derived growth factor. In other aspects, the first cargo molecule is a mitochondrial lytic peptide or a glycolysis inhibitor.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 16A-16C demonstrate the effect of $(KLAKLAK)_2$-ELP on mitochondrial depolarization. Cells were untreated (FIG. 16A), or treated with positive control (FIG. 16B), or with 25 µM $(KLAKLAK)_2$-ELP nanoparticles (FIG. 16C).

FIGS. 18A and 18B demonstrate the results from a JC-1 mitochondrial depolarization assay in untreated cells (FIG. 18A) or cells treated with $(KLAKLAK)_2$-ELP nanoparticles. All cells were treated with a JC-1 dye prior to analysis. Non-apoptotic and apoptotic regions are marked.

FIGS. 23A-23D demonstrate the killing efficiency of cargo carrying nanoparticles containing a targeting subunit and a cargo subunit as compared to a control (FIG. 23A). Nanoparticles were formed from 50 µM of a cargo subunit: $(KLAKLAK)_2$-ELP and varying concentrations of a target subunit (keratinocyte growth factor-ELP ("KGF"): at 0 µM (FIG. 23B), 100 µM (FIG. 23C), or 200 µM (FIG. 23D). Cell death was measured by a live (green) dead (red) assay. Bar=400 µM.

DETAILED DESCRIPTION

Figure 1:
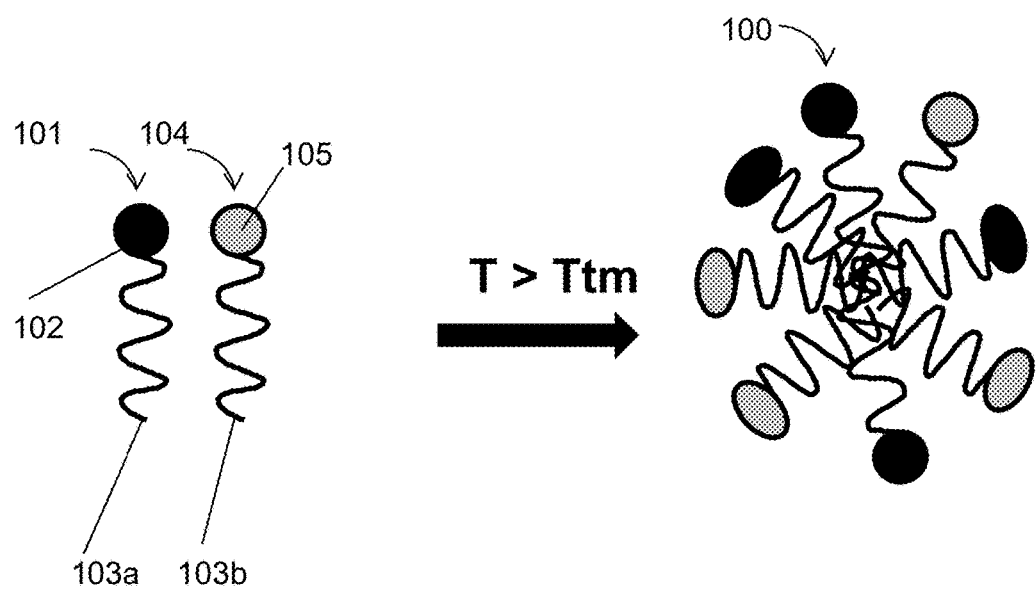
FIG. 1 shows one embodiment of a cargo carrying nanoparticle having two subunits: a targeting subunit and a cargo subunit.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

DEFINITIONS

As used herein, "about," "approximately," and the like, when used in connection with a numerical variable, generally refers to the value of the variable and to all values of the variable that are within the experimental error (e.g., within the 95% confidence interval for the mean) or within .+-.10% of the indicated value, whichever is greater.

As used herein, "control" is an alternative subject or sample used in an experiment for comparison purposes and included to minimize or distinguish the effect of variables other than an independent variable. A "control" can be positive or negative.

As used herein, "effective amount" is an amount sufficient to effect beneficial or desired results. An effective amount can be administered in one or more administrations, applications, or dosages.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "purified" is used in reference to a nucleic acid sequence, peptide, or polypeptide or other compound that has increased purity relative to the natural environment or the environment in which it was produced in.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "therapeutic" refers to treating or curing a disease or condition.

As used herein, "preventative" refers to hindering or stopping a disease or condition before it occurs or while the disease or condition is still in the sub-clinical phase.

As used herein, "separated" refers to the state of being physically divided from the original source or population such that the separated compound, agent, particle, chemical compound, or molecule can no longer be considered part of the original source or population.

As used herein, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data in stored on a suitable device such as a flash memory or CD-ROM.

As used herein, "chemotherapeutic agent" or "chemotherapeutic" refer to a therapeutic agent utilized to prevent or treat cancer.

As used herein, "nanoparticle" refers to any molecule, particle, or entity having a greatest dimension (diameter or length, width, or height) of less than 600 µm. Nanoparticles having a spherical shape are also generally referred to as "nanospheres." Nanoparticles can be heterogeneous or homogeneous.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "plasmid" as used herein refers to a non-chromosomal double-stranded DNA sequence including an intact "replicon" such that the plasmid is replicated in a host cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA or viral DNA, or may contain elements of both.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "specific binding partner" or "binding partner" is a compound or molecule to which a second compound or molecule binds with a higher affinity than all other molecules or compounds.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein "immunomodulator," refers to an agent, such as a therapeutic agent, which is capable of modulating or regulating one or more immune function or response.

As used herein, "targeting moiety" refers to a moiety or molecule that localizes to or away from a specific local, cell, and/or other molecule.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "operatively linked" indicates that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector. The same definition is sometimes applied to the specific arrangement of multiple coding sequences within a vector such that the sequences are expressed from the same vector in such a way that each coding sequence produces its desired product.

As used herein, "promoter" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, "identity," is a relationship between two or more polypeptide sequences, as determined by comparing the sequences. In the art, "identity" also refers to the degree of sequence relatedness between polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, "polypeptides" or "proteins" are as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein." Recombinant also refers to the polypeptide encoded by the recombinant nucleic acid. Non-naturally occurring nucleic acids or polypeptides include nucleic acids and polypeptides modified by man.

As used herein, "expression cassette" refers to the part of a DNA expression vector or plasmid that is capable of directing the cell to make RNA and protein. An expression cassette contains of one or more DNA sequences that code for a polypeptide, the sequences controlling expression of the coding DNA sequence(s) and other regulatory elements that otherwise influence expression of the coding DNA sequence(s) contained within the expression cassette.

As used herein, the term "fusion protein" or "fusion polypeptide" refers to a protein or polypeptide formed from the protein or polypeptide formed from the combination of two or more different proteins, polypeptides, or peptides. "Fusion polypeptide" or "fusion protein" also refers to the combination of a nucleic acid encoding a polypeptide to a promoter sequence, where the coding sequence and promoter sequence are from different sources or otherwise do not typically occur together naturally (e.g, a nucleic acid and a constitutive promoter), As used herein, "gene" refers to a hereditary unit corresponding to a sequence of DNA that occupies a specific location on a chromosome and that contains the genetic instruction for a characteristic(s) or trait(s) in an organism.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

As used herein, "functional variant" refers to a variant of a protein or polypeptide (e.g., a variant of a KGF protein) that can perform the same functions or activities as the original protein or polypeptide, although not necessarily at the same level (e.g., the variant may have enhanced, reduced or changed functionality, so long as it retains the basic function).

As used herein, "inhibit" or "inhibiting" expression of a gene indicates that something (e.g., antisense nucleotide, suppressor, antagonist, etc.) acts to reduce or prevent (completely or partially) the transcription, translation and/or other processing step in the expression of a gene, thereby down-regulating the gene expression so that a reduced amount of the active protein encoded by the gene is produced as compared to wild type.

As used herein, "selectable marker" refers to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

As used herein, "constitutive promoter" is a promoter that allows for continual or ubiquitous transcription of its associated gene or polynucleotide. Constitutive promoters are generally are unregulated by cell or tissue type, time, or environment.

As used herein, "inducible promoter" is a promoter that allows transcription of its associated gene or polynucleotide in response to a substance or compound (e.g. an antibiotic, or metal), an environmental condition (e.g. temperature), developmental stage, or tissue type.

As used herein, "wild-type" is the typical form of an organism, variety, strain, gene, protein, or characteristic as it occurs in nature, as distinguished from mutant forms that may result from selective breeding or transformation with a transgene.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein "induces," "inducing," or "induced" refers to activating or stimulating a process or pathway within a cell, such as macropinocytosis.

As used herein "heterogeneous" refers to a population of molecules, including nanoparticles, proteins, and polypeptides, or a population of subunits of a molecule that contains at least 2 molecules or subunits that are different from one another.

As used herein "homogenous" refers to a population of molecules, including nanoparticles, proteins, and polypeptides, or a population of subunits of a molecule in which all the molecules or subunits are identical to one another.

As used herein "small molecule" refers to a compound or molecule that is so dimensioned such that it can be internalized by a single cell.

DISCUSSION

According to the CDC, cancer is the second leading cause of death in the United States. Lung cancer remains the leading cause of death among all cancers in the United States. In 2008, an estimated 1.61 million new cases of lung cancer, which represents 12.7% of all new cancer diagnosis, were diagnosed worldwide. Further, in 2008 an estimated 1.38 million deaths were attributed to lung cancer.

Lung cancers are typically treated with chemotherapy to improve quality of life, palliate symptoms, and improve survival. Several chemotherapeutic drugs have been developed for treatment of lung cancer. These chemotherapeutic drugs include DNA damaging drugs, such as cisplatin and mitotic inhibitors, such as paclitaxel or doxorubicin. However, all these agents come with significant side effects such as nephrotoxicity, which may result from its nonspecific systemic organ distribution and inadequate intratumor concentrations.

Efforts have been expended to develop chemotherapeutic drugs or agents that that selectively affect tumor cells. Typically, these selective chemotherapeutic drugs or agents are configured to target molecules that are uniquely expressed, overexpressed, or mutated in cancer tumors. One such target is the epidermal growth factor receptor (EGFR), which is overexpressed in about 50 to about 90 percent of lung cancers. Monoclonal antibodies against EGFR (cetuximab) and tyrosine kinase inhibitors (TKI) that inhibit the tyrosine kinase activity of EGFR (erlotinib or gefitinib) have been developed and have only been marginally successful in clinical trials for the treatment of lung cancer.

Further, acquired resistance remains a problem with chemotherapy treatments, particularly with TKI treatment, with chemotherapeutic treatment. For example, although TKIs show promising response rates in lung cancer patients, acquired resistance to the TKI always develops about 10 months (on average) after beginning treatment. The acquired resistance can be attributed to several factors such as secondary mutation of the EGFR gene, amplification of the hepatocyte growth factor receptor (MET) gene, and/or overexpression of hepatocyte growth factor (HGF). As such, patient prognosis for lung cancer remains poor. Indeed, the 5-year survival rate of less than about 5% and a median survival of about 1 year.

With this in mind, described herein are compositions and formulations that include polypeptides that can selectively target cancer cells and induce cell death via mechanisms that are difficult for the cancer cell to adapt to and reduce or eliminate acquired resistance by cancer cells. In one embodiment, a cargo carrying nanoparticle contains a first fusion polypeptide that contains a growth factor targeting moiety operatively linked to an elastin-like peptide (ELP) and a second fusion polypeptide that contains a cargo molecule, such as a mitochondrial lytic peptide or glycolysis inhibitor, operatively linked to an (ELP). The growth factor can specifically bind to a binding partner located on the surface of a cell such that the macropinocytosis pathway is induced. The cargo carrying nanoparticles are internalized by a cell by macropinocytosis, which increases the efficiency of drug uptake and reduces systemic circulation of the cargo carrying nanoparticles.

By operatively linking the targeting moiety or cargo molecule to an ELP, the cargo carrying nanoparticles can self-assemble from their constituent subunit polypeptides and be produced at a low cost. Moreover, as disclosed herein, ELP interacts with cell surface heparan sulfates, which ensures that the cargo carrying nanoparticles are close to the cell surface and increases the efficiency of uptake. Indeed, for every one cargo carrying nanoparticle that has a targeting moiety specifically binds a binding partner on the cell surface that induces macropinocytosis, multiple cargo carrying nanoparticles can be internalized. Thus, the efficiency of uptake of the cargo carrying nanoparticles disclosed herein is greater than what can be achieved by other chemotherapeutics that rely on receptor mediated endocytosis, in which only one molecule (the molecule that is bound to the receptor) is internalized at a time.

Additionally, lytic peptides and glycolysis inhibitors do not target any specific pathway or receptor within a cell. As such, it is difficult for the cell to adapt or mutate to develop resistance to the cargo carrying nanoparticle. Insofar as the cargo carrying nanoparticles described herein can target cancer, particularly lung cancer, cells and do not target any specific cellular pathway or receptor, these cargo carrying nanoparticles can reduce tumor volume and burden with minimal side effects and minimize or eliminate acquired resistance.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Cargo Carrying Nano Particles

Provided herein are embodiments of cargo carrying nanoparticles that contain a targeting moiety fused to a first ELP ($ELP_1$), which forms a targeting subunit, and a cargo molecule that is also fused to a second ELP ($ELP_2$), which forms a cargo subunit. In other embodiments, the cargo carrying nanoparticles contain one or more additional cargo molecules that are each fused to a separate ELP ($ELP_n$), which forms additional cargo subunits. In yet further embodiments, the cargo carrying nanoparticles contain one or more transport moieties that are each fused to a separate ELP, which form additional transport subunits.

In some embodiments, $ELP_{1...n}$ are substantially (95% or greater sequence identity) the same ELP In other embodiments $ELP_{1...n}$ are substantially different (less than 95% sequence identity) from at least one other ELP in the assembled cargo carrying nanoparticle In some embodiments, there are equal numbers of targeting subunits and cargo subunits in the assembled cargo carrying nanoparticles. In other embodiments, the number of targeting subunits in the assembled cargo carrying nanoparticles is unequal to the number of cargo subunits in the assembled cargo carrying nanoparticles. In embodiments where there is more than one type of targeting subunits in the assembled cargo carrying nanoparticle, the number of one type targeting subunit can be equal to the number of the other types of targeting subunits in the assembled nanoparticle. In other of these embodiments, the number of one type of targeting subunits in the assembled cargo carrying nanoparticle is different from the number of at least one other type of targeting subunit present in the assembled nanoparticle.

Figure 2:
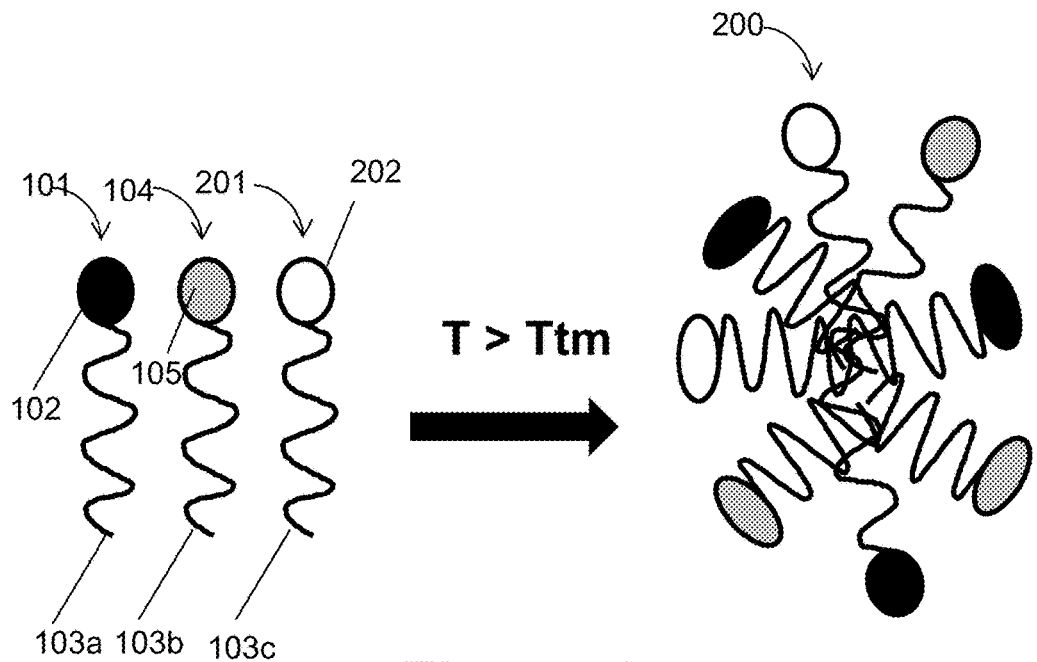
FIG. 2 shows one embodiment of a cargo carrying nanoparticle having three subunits: a targeting subunit and a first cargo subunit and a second cargo subunit.

The cargo carrying nanoparticles are spontaneously formed or self-assembled when the temperature of a solution containing the nanoparticle subunits is above the transition temperature. FIG. 1 shows one embodiment of a cargo carrying nanoparticle 100 that contains two different subunits: 1) a targeting subunit 101 that contains at least a targeting moiety 102 fused to a first ELP 103a and 2) a cargo subunit 104 that contains a cargo molecule 105 fused to a second ELP 103b. FIG. 2 shows one embodiment of a cargo carrying nanoparticle 200 that contains three different subunits: 1) a targeting subunit 101 that contains a targeting moiety 102 fused to a first ELP 103a, 2) a first cargo subunit 104 that contains a first cargo molecule 105 fused to a second ELP 103b, and 3) a second cargo subunit 201 that contains a second cargo molecule 202 fused to a third ELP 103c. As is shown in FIGS. 1 and 2, the cargo transporting nanoparticles (100 and 200) self-assemble from the subunits at a temperature (T) above a phase transition temperature of the nanoparticle ($Tt_m$) to form the cargo carrying nanoparticles (100 and 200). One of ordinary skill in the art will instantly appreciate that the transition temperature is dependent on the chemical composition of the individual units of the nanoparticle discussed above. In some embodiments, the T can range between about 5° C. and about 40° C.

The size of the cargo carrying nanoparticles is less than about 1000 nm. In some embodiments, the size of the cargo carrying nanoparticles ranges from about 1000 nm to about 500 nm. In further embodiments, the size of the nanoparticles range from about 250 nm to about 500 nm. In other embodiments, the size of the nanoparticles range from about 100 nm to about 250 nm. In yet other embodiments, the size of the nanoparticles ranges from about 0.001 nm to about 100 nm. In some embodiments, the size of the cargo carrying nanoparticle is minimized so as to increase the efficacy of the nanoparticles in vivo. In these embodiments, the size of the nanoparticle is about 500 nm or less. Size of the nanoparticles can be manipulated by, inter alia, by increasing the hydrophobicity of the nanoparticle subunits.

Elastin-Like Polypeptides (ELPs)

ELPs are a class of stimulus responsive biopolymers that are soluble macromolecules at temperatures below a phase transition temperature of the ELP ($Tt_{ELP}$) and self-assemble into nanoparticles such as micelles, micron-scale cacervates, or viscous gels, at temperatures above the $Tt_{ELP}$. This phase transition is reversible and the self-assembly can be controlled by manipulating the $Tt_{ELP}$. The $Tt_{ELP}$ can be manipulated by altering the ELP. Manipulation of the ELP can be by altering the polypeptide chain length or by altering the polypeptide sequence.

ELPs are repetitive polypeptides that evolved from the hydrophobic domain of elastin. The repeat polypeptide unit in ELPs is a pentapeptide of VPGXG (SEQ ID NO: 1), where "X" can be any amino acid other than P. The number of repeat units in the ELP can vary. The ELPs described herein can have about 1 to about 180 repeat units per ELP. The exact sequence of the ELP depends on a variety of factors including properties (e.g. hydrophobicity and molecular weight) of the cargo molecules and targeting moieties to be fused to the ELP, the desired $Tt_{ELP}$ and/or $Tt_m$, the desired nanoparticle to be formed, the application in which the nanoparticle will be used. The ELP can be homogenous (having the same repeat units) or can be heterogeneous (having different repeat units). In some embodiments, X is C, V, M, I, L, F, or W. In some embodiments, the ELP is made of five repeat units. In some of these embodiments, the X in the repeat units 1, 2, 4, and 5 is V and the X in repeat unit 3 is C, M, I, L, F, or W. In these embodiments, the sequence of the ELP corresponds to SEQ ID NO: 2, SEQ ID NO: 3, SEQ ID NO: 4, SEQ ID NO: 5, SEQ ID NO: 6, or SEQ ID NO: 7. The ELPs can interact with cell surface heparan sulfates, which attract and keep the cargo carrying nanoparticles near the cell surface to increase uptake of more cargo carrying nanoparticles during macropinocytosis. In some embodiments, the ELP has a cDNA sequence according to SEQ ID NO: 8, which encodes a polypeptide sequence according to SEQ ID NO: 9.

In other embodiments, the ELP contains strings of hydrophobic amino acids, e.g. poly leucine repeat units. In these embodiments, the fusion polypeptide takes to form of Cargo Molecule or Targeting moiety-[poly leucine]n-ELP. The number of leucine residues in the poly leucine repeat unit can range from 2-50. The number of poly leucine repeat units (n) can range from 1 to 50. In some embodiments the number of ELP repeat units ranges from about 50 to about 250 repeat units. In other embodiments, the ELP has a cDNA sequence according to SEQ ID NO: 8, which encodes a polypeptide sequence according to SEQ ID NO: 9.

Targeting Moieties and Binding Partners

The cargo carrying nanoparticles contain at least one targeting subunit that made of a targeting moiety fused to an ELP. The targeting moiety is configured to specifically bind a binding partner, which can be any receptor or protein present on the cell surface that enhances the macropinocytotic pathway. In some embodiments, the specific binding of the targeting moiety to its binding partner results in enhanced uptake of the nanoparticles. In this way, toxicity and other side effects can be decreased. Toxicity and other side effects are reduced because the cargo carrying nanoparticles are targeted to only the desired cells. The binding partner is located on the surface of a cell (i.e. associated with, attached to, or integrated within the cell membrane), such as a cancer cell.

Figure 3:
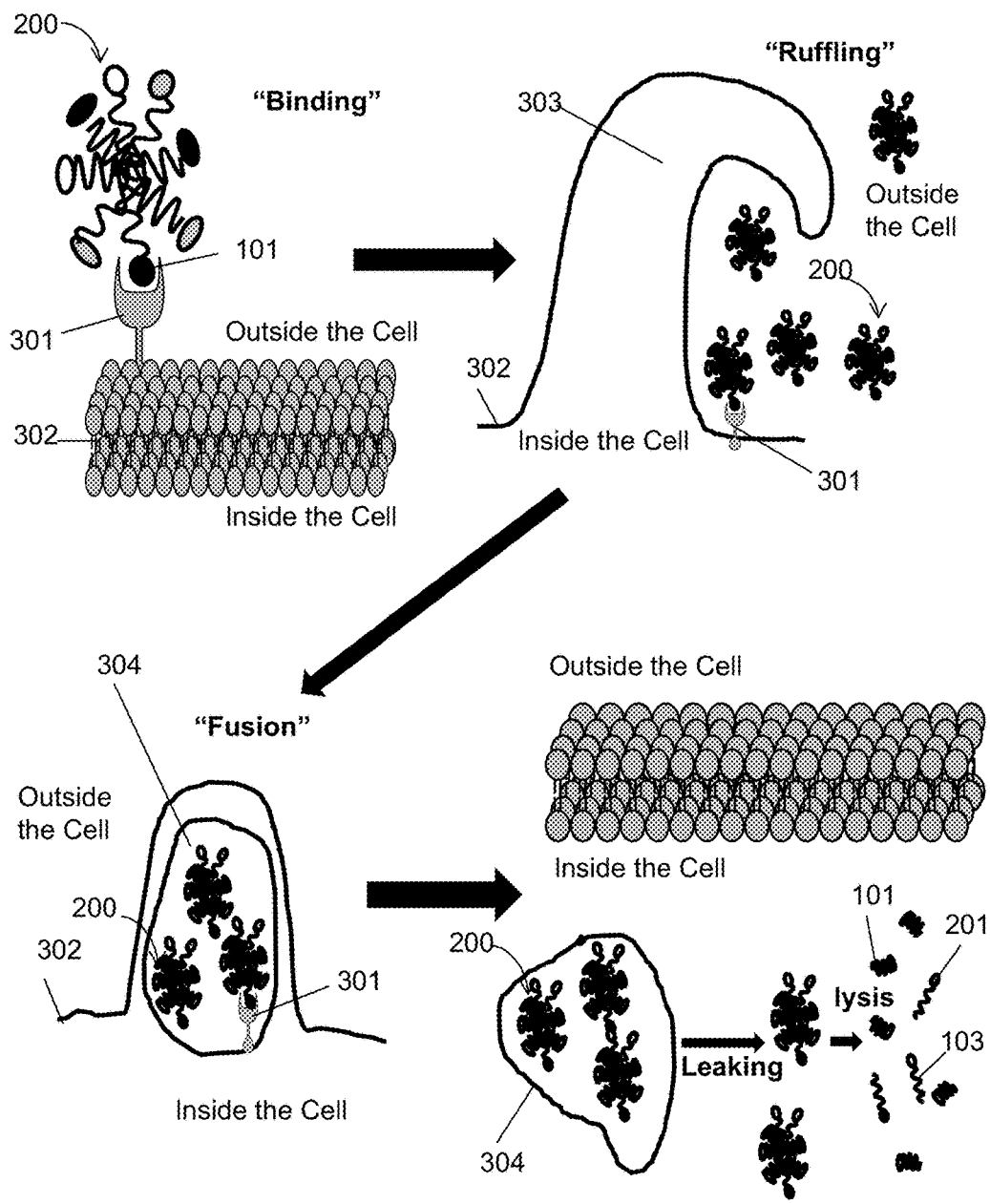
FIG. 3 demonstrates macropiocytosis mediated internalization of the cargo carrying nanoparticles in a cell.

Macropinocytosis is a form of bulk uptake of fluid and solid cargo into cytoplasmic vacuoles, called micropiosomes. As shown in FIG. 3, specific binding of the targeting moiety 101 of the cargo carrying nanoparticle 200 to its binding partner 301 located on the plasma membrane of a cell 302 activates the macropinocytosis pathway and the cargo carrying nanoparticle is internalized. Briefly, after specific binding of the targeting moiety 101 to its binding partner 301, actin-mediated bending of a single surface lamellipodia gives rise to a curved "ruffles" 303 during a process referred to as "ruffling." The ruffle 303 then fuses back with the plasma membrane of the cell during the "fusion" step and encapsulates the extracellular fluid and cargo carrying nanoparticles 200 thus forming the a macropinosome 304. The macropinosomes are inherently leaky. Thus, the cargo carrying nanoparticle 200 can leak out of the macropinosomes and escapes lysosomal degradation and is delivered to the cell. Once delivered, cargo carrying nanoparticles are lysed into their individual subunits (101, 102, and 201). In some instances lysing of the cargo carrying nanoparticles 200 renders the cargo molecule biologically active.

Macropinocytosis is beneficial over the commonly described receptor mediated internalization approaches that typically involve clathrin coated endocytosis. First, macropinosomes are relatively large (>about 1 μm), thereby efficiently internalizing several cargo carrying nanoparticles in one macropinosome. As the macropinosomes are inherently leaky, macropinocytosis results in rapid release of the cargo carrying nanoparticles into the cytoplasm of the cell, thus escaping lysosomal degradation. Further, typical receptor mediated internalization results in the uptake of one nanoparticle per receptor, whereas in internalization by macropinocytosis one cargo carrying nanoparticle specifically binds to the receptor but, as shown in FIG. 3, several cargo carrying nanoparticles that are in the vicinity of the cell surface are internalized. Moreover, not only does the targeting moiety allow targeted delivery of the cargo carrying nanoparticles to specific cells, the specific binding of the targeting moiety to its binding partner on the surface of the cell can increase macropinocytosis in these cells.

As discussed above, the targeting moiety is configured to induce the micropinocytosis pathway when it specifically binds to its binding partner. In some embodiments the targeting moiety is a growth factor. In some of these embodiments, the targeting moiety is epidermal growth factor, platelet derived growth factor, keratinocyte growth factor, or combinations thereof. In other embodiments, the targeting moiety is not a growth factor but otherwise induces the macropinocytotic pathway upon specifically binding to a binding partner.

In some embodiments, the growth factor is a human EGF. The cDNA sequence of the human EGF can correspond to SEQ ID NO: 10. The human EGF polypeptide can have a sequence according to SEQ ID NO: 11. In some embodiments, the human EGF is a variant of SEQ ID NO: 10 or SEQ ID NO: 11. In further embodiments, the EGF cDNA sequence is about 75% to about 99% identical to SEQ ID NO: 10. In other embodiments, the EGF polypeptide sequence is about 75% to about 99% identical to SEQ ID NO: 11.

In other embodiments, the growth factor is a human KGF. The cDNA sequence of the human KGF can correspond to SEQ ID NO: 12. The human KGF polypeptide can have a sequence according to SEQ ID NO: 13. In further embodiments, the KGF cDNA sequence is about 75% to about 99% identical to SEQ ID NO: 12. In other embodiments, the KGF polypeptide sequence is about 75% to about 99% identical to SEQ ID NO: 13.

The cDNA sequence of the human platelet derived growth factor can correspond to SEQ ID NO: 14. In further embodiments, the platelet derived cDNA sequence is about 75% to about 99% identical to SEQ ID NO: 14. In some embodiments, a platelet derived growth factor polypeptide is encoded by a cDNA according to SEQ ID NO: 14. In other embodiments, the platelet derived growth factor polypeptide is encoded by a cDNA that is about 75% to about 99% identical to SEQ ID NO: 14.

As previously discussed, the targeting moiety specifically binds a binding partner that is located on the cell surface. This specific binding triggers macropinocytosis and internalization of the cargo carrying nanoparticles. The binding partner can be associated with, attached to, or integrated with a membrane of a cell. In some embodiments, the binding partner is associated with, attached to, or integrated with the plasma membrane. The binding partner is configured to activate the macropinocytosis pathway upon specific binding of a targeting moiety.

In some embodiments, the binding partner is a growth factor receptor. In some of these embodiments, the growth factor receptor is epidermal growth factor receptor, platelet derived growth factor receptor, keratinocyte growth factor receptor, or combinations thereof. The epidermal growth factor receptor can be a human epidermal growth factor receptor. In some embodiments the epidermal growth factor receptor has a cDNA sequence according to SEQ ID NO: 15.

In other embodiments, the epidermal growth factor receptor has a cDNA sequence that is about 75% to about 99% identical to SEQ ID NO: 15. In some of embodiments, the epidermal growth factor receptor has a polypeptide sequence according to SEQ ID NO: 16. In other embodiments, the sequence of the epidermal growth factor receptor is at least about 75% to about 99% identical to SEQ ID NO: 16.

The keratinocyte growth factor receptor can be a human keratinocyte growth factor receptor. In some embodiments the keratinocyte growth factor receptor has a cDNA sequence according to SEQ ID NO: 17. In other embodiments, the keratinocyte growth factor receptor has a cDNA sequence that is about 75% to about 99% identical to SEQ ID NO: 17. In some embodiments, the human keratinocyte growth factor receptor has a polypeptide sequence according to SEQ ID NO: 18. In other embodiments, the sequence of the keratinocyte growth factor receptor is at least about 75% to about 99% identical to SEQ ID NO: 18.

The platelet derived growth factor receptor can be a human platelet derived growth factor receptor. In some of embodiments, the human platelet derived growth factor receptor has a cDNA sequence according to SEQ ID NO: 19. In other embodiments, the cDNA sequence of the platelet-derived growth factor receptor is at least about 75% to about 99% identical to SEQ ID NO: 19. In some embodiments, a platelet derived growth factor receptor polypeptide is encoded by a cDNA corresponding to SEQ ID NO: 19. In other embodiments, the platelet derived growth factor receptor is encoded by a cDNA sequence that is about 75% to about 99% identical to SEQ ID NO: 19. In other embodiments, the binding partner is not a growth factor receptor.

Cargo Molecules

The cargo carrying nanoparticle contains one or more cargo subunits that each contain a cargo molecule fused to an ELP. A single cargo carrying nanoparticle can contain a single type of cargo molecule, as in FIG. 1. In other embodiments, a single cargo carrying nanoparticle contains more than one type of cargo molecules. An example of this embodiment is shown in FIG. 2. The cargo molecule can be any polypeptide that can be fused to an ELP according to the methods described herein. In some embodiments, the cargo molecule is a polypeptide that can suppress, stimulate, or otherwise modify a cellular process, including but not limited to, glycolysis, ATP production, transcription, translation, growth, metabolism, catabolism, endocytosis, phagocytosis, pinocytosis, macropinocytosis, migration, malignant transformation, signal transduction, DNA modification, histone modification, mitosis, meiosis, DNA repair, senescense, and apoptosis.

The cargo molecule can be a lytic peptide, including but not limited to a mitochondrial lytic peptide. In an embodiment where the cargo molecule is a mitochondrial lytic peptide, the mitochondrial lytic peptide has a cDNA sequence according to SEQ ID NO: 22, which encodes a polypeptide having a sequence according to SEQ ID NO: 23. In some embodiments, the cDNA sequence of the mitochondrial lytic peptide is about 75% to about 99% identical to SEQ ID NO: 22. In other embodiments, the mitochondrial lytic peptide is about 75% to about 99% identical to SEQ ID NO: 23. Once internalized, the mitochondrial lytic peptides lyse the mitochondrial membrane, which results in cell death. Lytic peptides do not target specific pathways with in the cells. Therefore, this will not result in acquired resistance, unlike typical cancer therapies.

In other embodiments, the cargo molecule can be an inhibitor of glycolysis. In some embodiments, the glycolysis inhibitor inhibits hexokinase. In an embodiment, the hexokinase inhibitor has a cDNA sequence according to SEQ ID NO: 24, which encodes a polypeptide according to SEQ ID NO: 25. In some embodiments, the cDNA sequence of the hexokinase inhibitor is about 75% to about 99% identical to SEQ ID NO: 24. In other embodiments, the hexokinase inhibitor polypeptide is about 75% to about 99% identical to SEQ ID NO: 25.

In other embodiments, the glycolysis inhibitor inhibits phosphoglycerate mutase. In an embodiment the cDNA of the phosphoglycerate mutase inhibitor corresponds to SEQ ID NO: 26, which encodes a polypeptide according to SEQ ID NO: 27. In some embodiments, the cDNA sequence of the phosphoglycerate mutase inhibitor is about 75% to about 99% identical to SEQ ID NO: 26. In other embodiments, the phosphoglycerate mutase inhibitor polypeptide is about 75% to about 99% identical to SEQ ID NO: 27.

In other embodiments, the glycolysis inhibitor inhibits phosphofructokinase. In an embodiment the cDNA of the phosphofructokinase inhibitor corresponds to SEQ ID NO: 28, which encodes a polypeptide according to SEQ ID NO: 29. In some embodiments, the cDNA sequence of the phosphofructokinase inhibitor is about 75% to about 99% identical to SEQ ID NO: 28. In other embodiments, the phosphofructokinase inhibitor polypeptide is about 75% to about 99% identical to SEQ ID NO: 29.

In further embodiments, the cargo molecule can be DNA, RNA, virus particles and complete viruses, lipids (e.g. all forms of cholesterol, including but not limited to LDL cholesterol), bacteria, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In other embodiments, the cargo carrying nanoparticles contain one or more cargo binding peptide sequences. The cargo binding peptide sequences can bind to the cargo molecule and assist in its cellular internalization. For example, the cholesterol binding sequence, LDLR-3, can be fused or operatively linked with ELP and thus cholesterol molecules can be loaded in the nanoparticles via binding to the LDLR-3 sequence leading to the uptake of cholesterol. In some embodiments, LDL-R 3 has a cDNA sequence according to SEQ ID NO: 20. In other embodiments, LDL-3 has a cDNA sequence that is about 90 to about 99% identical to SEQ ID NO: 20. In some embodiments, LDL-3 has a polypeptide sequence according to SEQ ID NO: 21. In other embodiments, LDL-3 has a polypeptide sequences that is about 90% to about 99% identical to SEQ ID NO: 21.

Methods of Making Cargo Carrying Nano Particles

The cargo subunits and the targeting subunits can be made using recombinant DNA techniques that result in fusion of the ELP polypeptide to a cargo molecule polypeptide or a targeting moiety. In other embodiments, the cargo subunits and targeting subunits are chemically synthesized de novo, using techniques and methods generally known to those skilled in the art.

Vectors

In some embodiments, a nucleotide sequence encoding a cargo molecule or a targeting moiety is operatively linked (e.g. cloned in frame) with a nucleotide sequence encoding an ELP in a vector. In some embodiments, a linker molecule is inserted between the nucleotide sequence encoding the targeting moiety or cargo molecule and the ELP. In some embodiments, the nucleotide sequence also includes regulatory sequences (e.g. promoters) in addition to those already present in the vector. In some embodiments, the nucleotide sequence is chemically synthesized de novo using techniques generally known to those skilled in the art. In other embodiments, recombinant DNA engineering techniques are used to generate the nucleotide sequence. In some embodiments, the nucleotide sequence encoding a cargo molecule operatively linked to an ELP corresponds to SEQ ID NO: 30, which encodes a polypeptide according to SEQ ID NO: 31. In other embodiments, the nucleotide sequence encoding a cargo molecule operatively linked to an ELP is about 75% to about 99% identical to SEQ ID NO: 30. In other embodiments, the cargo molecule cDNA corresponds to any of SEQ ID NOs: 24, 26, or 28, or cDNA sequences about 75% to about 99% identical to SEQ ID NOs: 24, 26, or 28.

In some embodiments, the nucleotide encoding a targeting moiety operatively linked to an ELP corresponds to SEQ ID NO: 32, which encodes a polypeptide according to SEQ ID NO: 33. In other embodiments, the nucleotide encoding a targeting moiety operatively linked to an ELP corresponds to SEQ ID NO: 34, which encodes a polypeptide according to SEQ ID NO: 35. In other embodiments, the nucleotide sequence encoding a targeting moiety operatively linked to an ELP is about 75% to about 99% identical to SEQ ID NO: 34. In other embodiments, the targeting moiety cDNA corresponds SEQ ID NO: 14, or cDNA sequences about 75% to about 99% identical to SEQ ID NO: 14.

In some embodiments, a single DNA vector contains multiple nucleotide sequences that each encode a different polypeptide subunit of the cargo carrying nanoparticle. For example, a single plasmid can contain a first nucleotide sequence that encodes a targeting subunit and a second nucleotide sequence that is operatively linked to the first nucleotide sequence, wherein the second nucleotide sequence encodes a first cargo subunit. In other embodiments, the vector can contain a third nucleotide sequence encoding a second cargo subunit, wherein the third nucleotide sequence is operatively linked to the first nucleotide sequence and/or the second nucleotide sequence. In further embodiments, a single vector can contain 1 to 50 more additional nucleotide sequences encoding additional targeting and/or cargo subunits In some embodiments the DNA vector is a suitable bacterial expression vector. In other embodiments, the plasmid vector is a suitable eukaryotic expression vector. Suitable bacterial and eukaryotic expression vectors are generally known in the art. In other embodiments, the nucleotides encoding the cargo subunit or targeting subunit can be synthetically generated using de novo nucleotide synthesis techniques generally known in the art. The de novo generated subunits can be inserted into a plasmid vector using techniques generally known in the art. In some embodiments the plasmid vector is a suitable bacterial expression vector. In other embodiments, the plasmid vector is a suitable eukaryotic expression vector. Suitable bacterial and eukaryotic expression vectors are generally known in the art. Suitable bacterial expression cells include, but are not limited to, PET25b+, BLR, and BLR(DE3) cells.

The nucleotides encoding the cargo subunit and/or the targeting subunit, if not already present in an expression vector, can be cloned into a suitable expression plasmid vector. In some embodiments the plasmid vector is a suitable bacterial expression vector. In other embodiments, the plasmid vector is a suitable eukaryotic expression vector. Suitable bacterial and eukaryotic expression vectors are generally known in the art.

The vectors can include any suitable regulatory elements (e.g. promoter sequences) or other nucleotide sequences which allow for, inter alia, replication, increased stability, selection (such as antibiotic resistance genes), and inducible expression.

Vector Expression

In some embodiments, bacterial cells are transformed with the plasmid expression vectors containing the nucleotides encoding the cargo subunit and/or the targeting subunit using techniques generally known in the art, such as but not limited to electroporation. Transformed bacteria can be selected for using generally known techniques and grown for an amount of time in a media at a suitable temperature to allow expression of the cargo subunit and/or targeting subunit in the bacterial cells. The amount of time the transformed bacteria are grown for can range from about 4 to about 24 hours. One of ordinary skill in the art will appreciate that the time for growth will vary, inter alia, according to the bacterial strain used, temperature of growth, the subunit being expressed, the expression vector used, and the media employed. The temperature can vary from about 25° C. to about 37° C. In an embodiment, the bacteria are cultured at 37° C. One of ordinary skill in the art will appreciate that temperature will vary, inter alia, according to the bacterial strain used, the desired growth rate, the subunit being expressed, the expression vector used, and the media employed. Suitable bacterial strains include, but are not limited to, variants of Escherichia coli that have been optimized for protein expression and purification and transformation. These are commercially available. In this way, the transformed bacteria express and nucleotide sequence in the plasmid expression vector and generate the cargo subunit and/or targeting subunit polypeptides. Suitable bacterial strains have previously been described herein.

In other embodiments, the cargo subunit and/or targeting subunit polypeptides are produced in a eukaryotic expression system. In these embodiments, the plasmid expression vector containing the nucleotide sequence encoding the cargo subunit/and or the targeting subunit is introduced using generally know techniques, such as transformation using retroviral particles or transfection using cationic liposomes, into an appropriate eukaryotic cell, such as but not limited to yeast. Other cell types will be appreciated by one of ordinary skill in the art. Suitable expression systems are generally known in the art, are commercially available, and include but are not limited to, Chinese hamster ovary cells. Transformed/transfected eukaryotic cells are grown using techniques generally known in the art to express the peptide sequence in the plasmid expression vector and generate the cargo subunit and/or targeting subunit polypeptides.

Polypeptide Purification and Evaluation

Once the cells have generated the subunit polypeptides, the subunit polypeptides are purified from the cell culture. Suitable polypeptide purification methods are generally known in the art. In some embodiments, the subunit polypeptides include a molecular tag, such as antibody epitope or metal binding site, which allows for affinity purification of the subunits. Such molecular tags are generally known in the art (Terpe, K. 2003. Appl. Microbiol. Biotechnol. 60:523-533) and include but are not limited to, FLAG tag, poly-His tag, and a poly-Arg tag. In these embodiments, the subunits can be affinity purified. In other embodiments, the cells in the cell culture are lysed using an appropriate method. Lysis can be performed using a physical method, such as sonication or using chemical lysis process, such as by using detergents. One of ordinary skill will appreciate that optimization of cell lysis will depend on, inter alia, the culture system used and the polypeptide to be purified. After cells have been lysed, cells can be fractionated and organelles can be isolated using techniques generally known in the art. Fractionation and/or organelle isolation can be obtained using physical disruption techniques and/or detergent-buffer solutions and density gradient methods. Optimization and utilization of tools generally known in the art can be used to obtain membrane bound proteins, cytosolic proteins, intact cell nuclei, mitochondria and other organelles.

In some embodiments, protease inhibitors, phosphatase inhibitors and protein stabilizers are added during the purification process to prevent and limit subunit degradation during the process. Such inhibitors are generally known in the art and are commercially available. In some embodiments, lysis and purification is conducted at cold temperatures (about 4° C. to about 8° C.) to minimize polypeptide degradation. In some instances, particularly where correct folding of a portion or all of the subunit are important reagents used during the lysis/fractionation or other compounds, such as salt, can be removed via dialysis. In some cases, dialysis of these reagents and/or compounds results in protein re-folding. In other instances, other buffers or reagents can be added to the purified protein to stimulate proper folding of the purified polypeptide.

After the subunit polypeptides are purified, physical properties of the purified polypeptides can be evaluated using suitable methods, such as but not limited to, spectrophotometric analysis or 1-D or 2-D gel electrophoresis followed by protein detection (gel staining (e.g. Coomassie staining, Western blotting, or mass-spectrometry). The function of the purified subunit polypeptides can be evaluated by a suitable method. For example, if the polypeptide contains a cargo molecule that is a mitochondrial lytic peptide, the functional activity of the purified subunit polypeptide can be evaluated by contacting a cell with the purified subunit polypeptide and evaluate cell death. After the subunits are allowed to spontaneously form the cargo-carrying nanoparticles, uptake of the cargo carrying nanoparticles can be analyzed using a suitable technique, including but not limited to flow cytometry and transmission electron microscopy.

Pharmaceutical Formulations Containing Cargo Carrying Nanoparticles

The cargo carrying nanoparticles described herein can be provided to a subject as an ingredient, such as an active ingredient, in a pharmaceutical formulation. As such, also described are pharmaceutical formulations containing one or more of the cargo carrying nanoparticles described herein. In some embodiments, the pharmaceutical formulations contain an effective amount of the cargo carrying nanoparticles described herein. The pharmaceutical formulations can be administered to a subject in need thereof. In some embodiments, the subject has cancer. In some embodiments, the cancer is a lung cancer. In further embodiments, the cargo carrying nanoparticles described herein are used in the manufacture of a medicament for the treatment of cancer.

The pharmaceutical formulations can contain a homogenous population of cargo carrying nanoparticles. In these embodiments, the cargo carrying nanoparticles are made of the same type of subunits as one another. For example, all cargo carrying nanoparticles in the pharmaceutical formulation contains one or more targeting subunits growth factor targeting moiety and one or more cargo subunits containing a glycolysis inhibitor peptide.

In other embodiments, the pharmaceutical formulations can contain a heterogeneous population of cargo carrying nanoparticles. In some of these embodiments, the cargo molecule can vary from nanoparticle to nanoparticle. For example, some cargo carrying nanoparticles in the pharmaceutical formulation contain one or more targeting subunits containing a growth factor targeting moiety and one or more cargo subunits containing a glycolysis inhibitor peptide and other cargo carrying nanoparticles contain one or more targeting subunits containing a growth factor targeting moiety and one or more cargo subunits containing a mitochondrial lytic peptide. In other embodiments, the targeting moiety varies between nanoparticles. For example, some cargo carrying nanoparticles contain one or more targeting subunits containing an epidermal growth factor targeting moiety and one or more cargo subunits containing a glycolysis inhibitor, while other cargo carrying nanoparticles in the population contain one or more targeting subunits having a platelet derived growth factor targeting moiety and one or more cargo subunits containing a glycolysis inhibitor. In yet further embodiments, the cargo carrying some of the cargo carrying nanoparticles contain different cargo subunits and targeting subunits than at least one other cargo carrying nanoparticles in the population.

Pharmaceutically Acceptable Carriers and Auxiliary Ingredients and Agents

The pharmaceutical formulations containing an effective amount of the cargo carrying nanoparticles described herein can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of the cargo carrying nanoparticles, the pharmaceutical formulation can also include an effective amount of auxiliary active agents, including but not limited to, antisense or RNA interference molecules, traditional chemotherapeutics, antineoplasic agents, immunomodulating compounds, hormones, antibiotics, antivirals, and/or antibodies or fragments thereof Effective Amounts of the Cargo Carrying Nanoparticles and Auxiliary Agents As the subunits spontaneously form into nanoparticles, the effective amount is based on an amount or concentration of the subunits present. In some embodiments, the effective amount is based on the amount or concentration of a cargo subunit present in the formulation. In some of these embodiments, the effective amount ranges from about 0.001 pg of cargo subunit to about 1,000 µg of cargo subunit. In other embodiments, the concentration of the cargo subunit in the effective amount ranges from about 1 µM to about 1,000 µM.

In other embodiments, the effective amount is based on the amount or concentration of a targeting subunit present. In some of these embodiments, the effective amount ranges from about 0.001 pg of cargo subunit to about 1,000 µg of targeting subunit. In other embodiments, the concentration of the targeting subunit in the effective amount ranges from about 1 µM to about 1,000 µM.

In further embodiments, the effective amount is based on the amount or concentration of all subunits present in the formulation. In some of these embodiments, the effective amount ranges from about 0.001 pg of the total subunits to about 1,000 µg of the total subunits. In other embodiments, the concentration of the subunits in the effective amount ranges from about 1 µM to about 1,000 µM.

In embodiments where there is an auxiliary active agent contained in the pharmaceutical formulation in addition to the cargo carrying nanoparticles, the effective amount of the auxiliary active agent will vary depending on the auxiliary active agent. In some embodiments, the effective amount of the auxiliary active agent ranges from 0.001 micrograms to about 1000 grams. In other embodiments, the effective amount of the auxiliary active agent ranges from about 0.01 IU to about 1000 IU. In further embodiments, the effective amount of the auxiliary active agent ranges from 0.001 mL to about 1000 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The auxiliary active agent can be included in the pharmaceutical formulation or can exist as a stand-alone compound or pharmaceutical formulation that is administered contemporaneously or sequentially with the conjugate compound, derivative thereof or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent ranges from 0.001 micrograms to about 1000 grams. In other embodiments, the effective amount of the auxiliary active agent ranges from about 0.01 IU to about 1000 IU. In further embodiments, the effective amount of the auxiliary active agent ranges from 0.001 mL to about 1000 mL. In yet other embodiments, the effective amount of the auxiliary active agent ranges from about 1% w/w to about 50% w/w of the total auxiliary active agent pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total auxiliary agent pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, and intradermal. Such formulations may be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, this is a subject having cancer. In some embodiments, the cancer is a lung cancer.

Where appropriate, the dosage forms described herein can be microencapsulated. The dosage form can also be prepared to prolong or sustain the release of any ingredient. In some embodiments, the conjugate compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the conjugate compound, derivative thereof, auxiliary active ingredient, and/or pharmaceutically acceptable salt thereof can be formulated with a paraffinic or water-misicible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the conjugate compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of a conjugate compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a conjugate compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulations. In addition to the conjugate compound, derivative thereof, auxiliary active ingredient, and/or pharmaceutically acceptable salt thereof, such a dosage form can contain a powder base such as lactose, glucose, trehalose, manitol, and/or starch. In some of these embodiments, the conjugate compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

For some embodiments, the dosage form contains a predetermined amount of a conjugate compound per unit dose. In an embodiment, the predetermined amount of the conjugate compound is an effective amount of the conjugate compound to treat, prevent, or mitigate the symptoms of multiple myeloma. In other embodiments, the predetermined amount of the conjugate compound is an appropriate fraction of the effective amount of the active ingredient. Such unit doses may therefore be administered once or more than once a day. Such pharmaceutical formulations may be prepared by any of the methods well known in the art.

Use of Cargo Carrying Nanoparticles

The cargo carrying nanoparticles described herein can be used for intracellular delivery of a polypeptide or other small molecules, including but not limited to, drugs, plasmids, genes etc. In some embodiments, a cell is contacted with one or more of the cargo carrying gene nanoparticles having a cargo molecule corresponding to a polypeptide desired to be delivered to a cell or containing a polypeptide that binds to specific cargo molecules such as plasmids or small molecules, including but not limited to cholesterol. In this way, targeted intracellular delivery of a polypeptide or other cargo molecules can be achieved.

Any amount of the cargo carrying nanoparticles or pharmaceutical formulations thereof, described herein can be administered to a subject in need thereof one or more times per day, week, month, or year. In some embodiments, the subject has one or more symptoms of a disease, condition, or syndrome. In some of these embodiments, the disease, condition, or syndrome is cancer. In some embodiments, the cancer is lung cancer. In some embodiments, the amount administered is the effective amount of the cargo carrying nanoparticles or pharmaceutical formulations thereof. For example, the cargo carrying nanoparticles or pharmaceutical formulations thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the cargo carrying nanoparticles or pharmaceutical formulations thereof are administered one or more times per month, such as 1 to 5 times per month. In still further embodiments, the cargo carrying nanoparticles or pharmaceutical formulations thereof are administered one or more times per year, such as 1 to 11 times per year.

In embodiments where more than one of the cargo carrying nanoparticles or pharmaceutical formulations thereof, and/or auxiliary agents are administered sequentially; the sequential administration may be close in time or remote in time. For example, administration of the second the cargo carrying nanoparticles or pharmaceutical formulations thereof can occur within seconds or minutes (up to about 1 hour) after administration of the first agent (close in time). In other embodiments, administration of the second the cargo carrying nanoparticles or pharmaceutical formulations thereof occurs at some other time that is more than an hour after administration of the first the cargo carrying nanoparticles or pharmaceutical formulations thereof.

The amount of the cargo carrying nanoparticles or pharmaceutical formulations thereof described herein can be administered in an amount ranging from about 0.01 mg to about 1000 mg per day, as calculated as the free or unsalted pharmaceutical formulations. The amount of the cargo carrying nanoparticles or pharmaceutical formulations thereof described herein can be administered in an amount ranging from about 0.01 uM to about 1000 uM per day, as calculated as free unassembled polypeptide subunits.

The cargo carrying nanoparticles or pharmaceutical formulations thereof described herein can be administered in combination with one or more other auxiliary agents that are independent of the pharmaceutical formulation. Suitable auxiliary agents include, but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Suitable compounds and molecules that can be auxiliary agents are described elsewhere herein in connection with the description of cargo molecules.

Kits

The cargo carrying nanoparticles, expression vector(s) containing nucleotide sequences encoding cargo subunit(s) and/or targeting subunit(s), cells containing one or more expression vector, and pharmaceutical formulations described herein can be presented as a combination kit. As used herein, the terms "combination kit" or "kit of parts" refers to the cargo carrying nanoparticles, expression vectors containing nucleotide sequences encoding cargo subunit(s) and/or targeting subunit(s), cells containing one or more expression vector, and pharmaceutical formulations described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the cargo carrying nanoparticles, pharmaceutical formulations thereof, or other auxiliary agent are not administered simultaneously, the combination kit can contain each agent, compound, nanoparticle, or formulation in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the cargo carrying nanoparticles, expression vectors containing nucleotide sequences encoding cargo subunit(s) and/or targeting subunit(s), cells containing one or more expression vectors, and pharmaceutical formulations contained therein, safety information regarding the content of the cargo carrying nanoparticles, expression vector(s) containing nucleotide sequences encoding cargo subunit(s) and/or targeting subunit(s), cells containing one or more expression vector, and pharmaceutical formulation(s) contained therein, information regarding the dosages, indications for use, and/or recommended treatment regimen(s) for the cargo carrying nanoparticles, expression vectors containing nucleotide sequences encoding cargo subunit(s) and/or targeting subunit(s), cells containing one or more expression vectors, and pharmaceutical formulations contained therein. In some embodiments, the instructions provide directions for administering the compounds, pharmaceutical formulations, or salts thereof to a subject having a cancer. In some embodiments, the cancer is lung cancer.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Induction of Cell Death by a Lytic Peptide-ELP Fusion Polypeptide

The lytic peptide (KLAKLAK)$_2$ (SEQ ID NO: 23) was fused to an ELP to produce a lytic peptide-ELP fusion polypeptide according to methods described herein. $10^5$ cells H292 cells were seeded in a 48 well plate, serum starved, and treated with comparable concentrations of the lytic peptide-ELP fusion polypeptide, which self-assembled into nanoparticles containing lytic peptide-ELP subunits, or the lytic peptide alone (i.e., (KLAKLAK)$_2$ only) for about 24 hours. The lytic peptide alone does not self-assemble into nanoparticles. A MTT cell proliferation assay was then performed to determine cell viability. The results from this experiment are shown in FIGS. 4A and 4B.

Figure 4A:
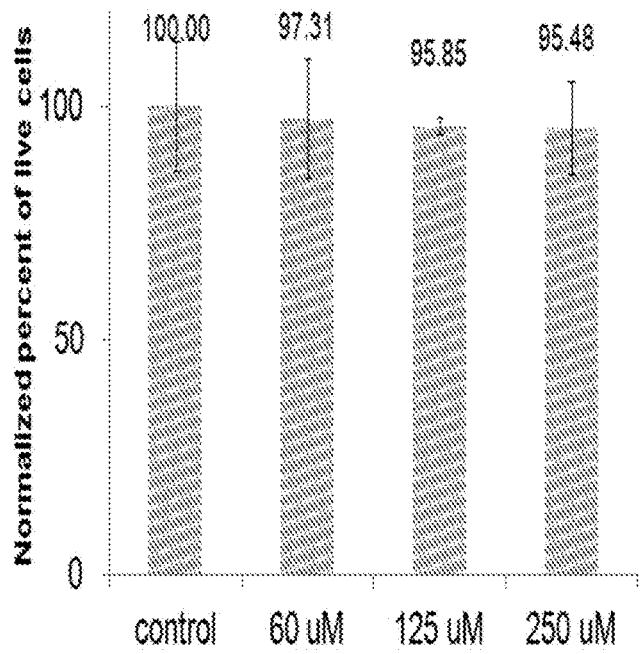
FIGS. 4A and 4B demonstrate cell death resulting from exposure to a lytic peptide fused to an elastin-like peptide (ELP).
Figure 4B:
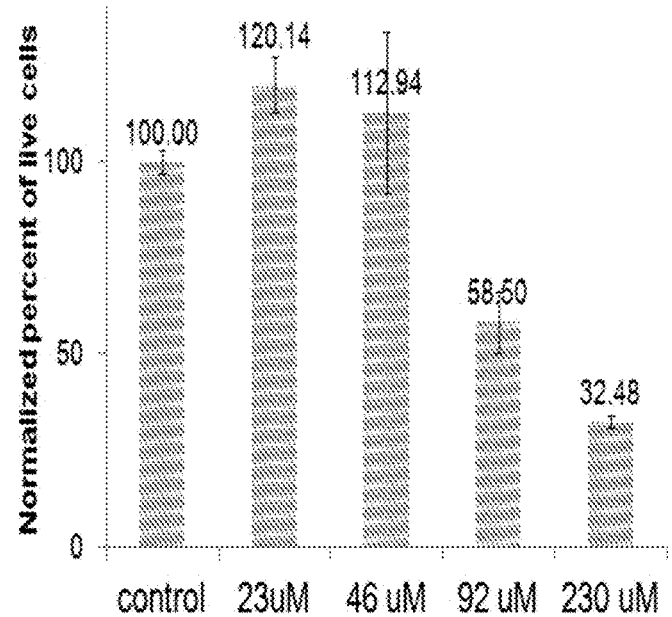

FIG. 4A demonstrates the effect of varying concentrations of the lytic peptide alone on cell viability. FIG. 4B demonstrates the effect of varying concentrations of the lytic peptide-ELP fusion polypeptide on cell viability. The lytic peptide alone did not result in a significant reduction in cell viability. In contrast, treatment of cells with nanoparticles made from lytic peptide-ELP fusion polypeptides resulted in a dose-dependent reduction of cell viability. At the greatest concentration, the nanoparticles containing the lytic peptide-ELP fusion polypeptides killed up to 68% of the cells.

Example 2

Depolarization of Mitochondria by Lytic Fusion $2 \times 10^5$ H292 cells were treated with a positive control (Carbonylcyanide m-chlorophenylhydrazone (CCCP)), negative control (JC-1), assay control (untreated cells) or 50 µM of the lytic peptide-ELP fusion polypeptides (See Example 1), which self-assembled into nanoparticles, for about 24 hours. After treatment, a JC-1 assay was performed to determine the mitochondrial membrane potential and detect mitochondrial membrane depolarization. Samples were then analyzed using flow cytometry and fluorescent microscopy.

Figure 5A:
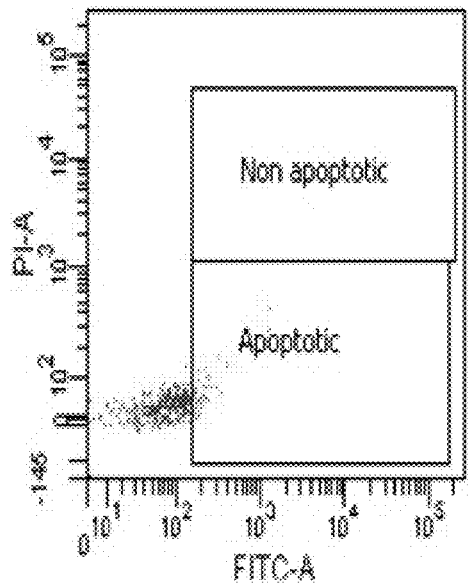
FIGS. 5A through 5D demonstrate the results from flow cytometry of cells after treatment with the lytic peptide fused to an ELP of FIGS. 4A and 4B. Treatment with the lytic peptide fused to an ELP resulted in depolarization of mitochondria.
Figure 5B:
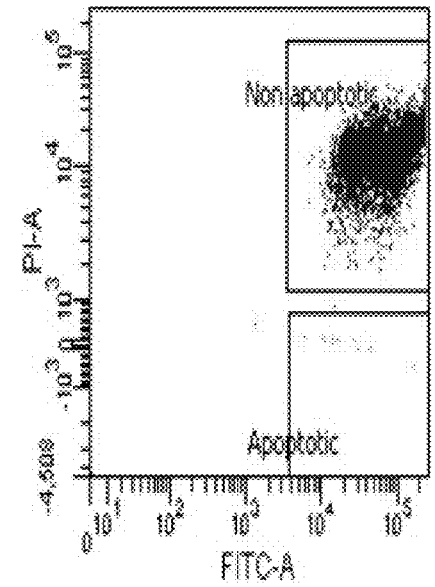
Figure 5C:
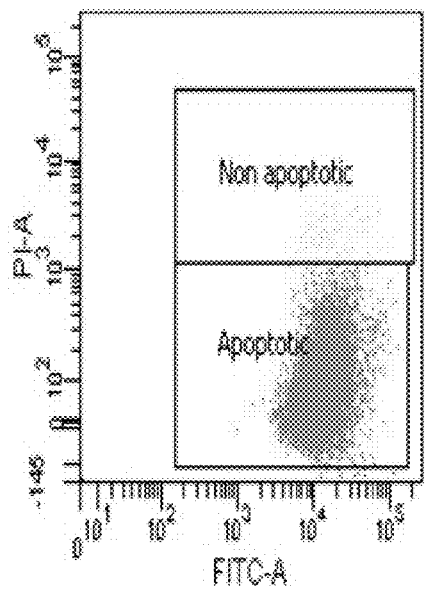
Figure 5D:
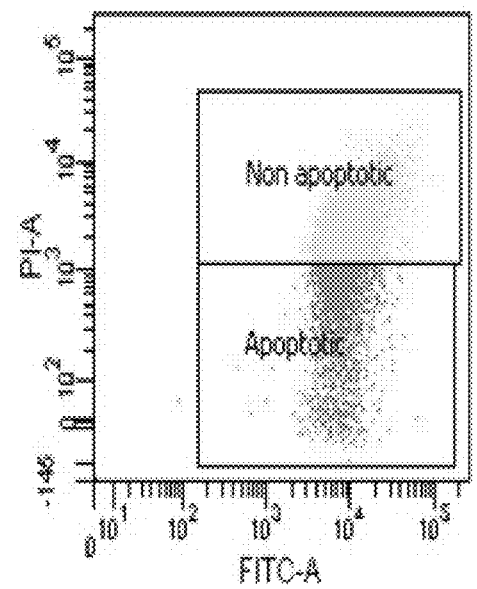

The results are shown in FIGS. 5A to 5D. FIG. 5A shows the results from the assay control. FIG. 5B shows the results from treatment of the cells with the negative control. FIG. 5C shows the results from treatment of the cells with the positive control. FIG. 5D shows the results from treatment with the lytic peptide-ELP fusion polypeptides. As shown in FIGS. 5A-5D, treatment with the lytic peptide-ELP fusion polypeptides resulted in apoptosis of a portion of the cell population.

Figure 6A:
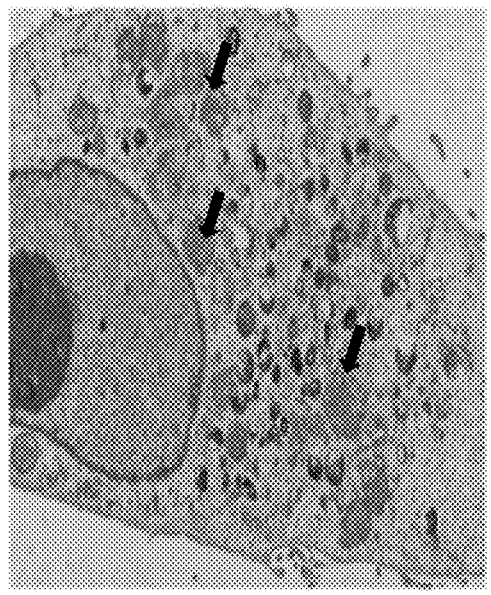
FIGS. 6A and 6B shown transmission electron microscope (TEM) pictures of control cells (FIG. 6A) and cells treated with the lytic peptide fused to an ELP (FIG. 6B) taken at 8600× that demonstrate swelling of mitochondria in response to the lytic peptide fused to an ELP, which is a consequence of mitochondrial depolarization.
Figure 6B:
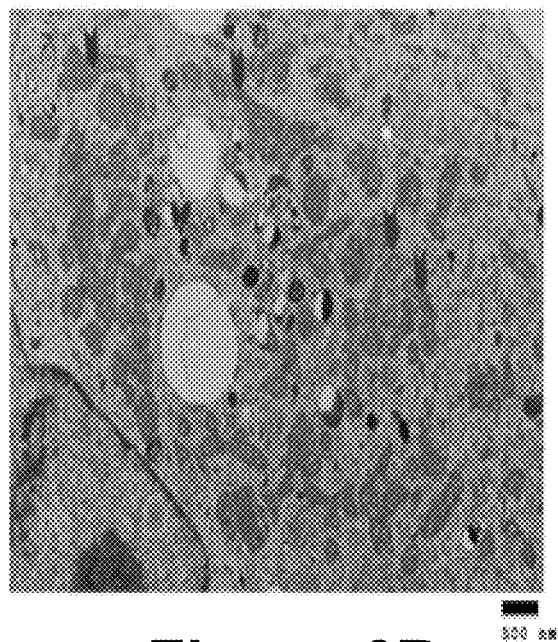

Additionally TEM pictures were taken at 8600× of the cells. FIG. 6A shows a TEM image of an untreated cell Arrows indicate regular shaped mitochondria. FIG. 6B shows a TEM image of a cell treated with lytic peptide-ELP fusion polypeptides. Arrows indicate swelled mitochondria, which is a consequence of mitochondrial depolarization.

FIGS. 16A-16C show representative images of HCC827 cells treated with a negative control (FIG. 16A), positive control (FIG. 16B), or 25 µM of (KLAKLAK)$_2$-ELP fusion polypeptides analyzed using fluorescent microscopy demonstrating mitochondrial depolarization. Red fluorescence indicates intact mitochondria and green fluorescence shows depolarized mitochondria.

Example 3

Figure 7:
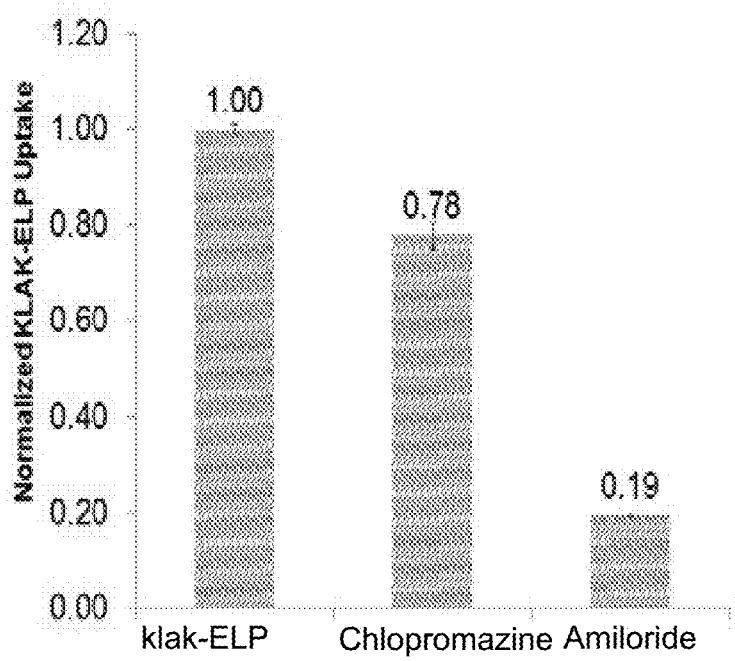
FIG. 7 demonstrates the uptake of the lytic peptide fused to an ELP in cells treated with blockers of receptor mediated endocytosis (chlopromazine) or macropinocytosis (amiloride).

Uptake of Lytic Peptide-ELP is Via Macropinocytosis $2 \times 10^5$ H292 cells per well were seeded in a 24 well plate. Cells were blocked prior to treatment with no blocking agent, chlorpromazine, or amiloride, which block the two major methods of uptake mechanisms. Chlorpromazine blocks receptor mediated endocytosis (RME) and amiloride blocks macropinocytosis (MAC). After blocking, cells were treated with 20 µM of (KLAKLAK)$_2$ peptide-ELP fusion polypeptides (See Example 2). Uptake of the (KLAKLAK)$_2$ peptide was measured using flow cytometry. The results from this experiment are shown in FIG. 7, which shows the normalized KLAK-ELP uptake in cells pretreated with chlorpromazine or amiloride. Uptake was most effected by pretreatment with amiloride, which indicates that macropinocytosis is a major mechanism of uptake of the KLAK-ELP observed.

Figure 8:
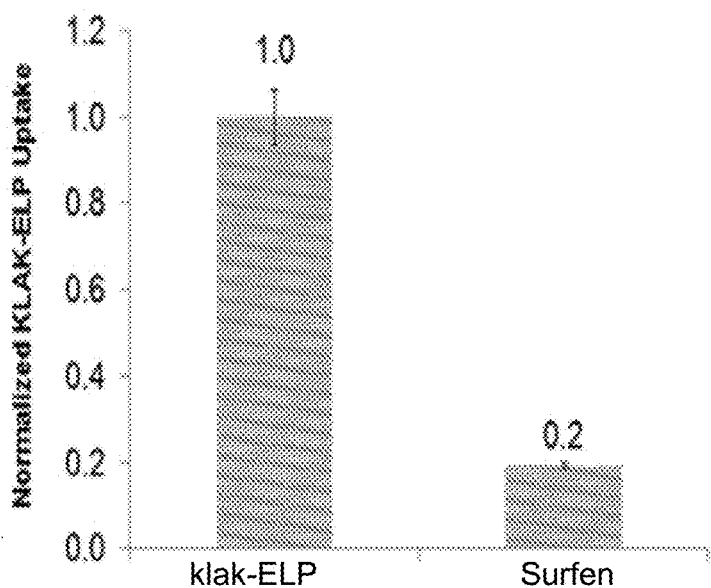
FIG. 8 demonstrates the uptake of the lytic peptide fused to an ELP in cells treated with surfen, which is an antagonist of heparan sulfate.

It was also determined that heparan sulfate (HS), which is a polysaccharide found on the surface of cells, interacts with ELPs. To determine if an interaction between ELP and HS assists in the uptake mechanism of the fusion polypeptides and nanoparticles disclosed herein, cells were pre-blocked with surfen, which is an antagonist of HS, or a negative control (KLAK-ELP only). As shown in FIG. 8, pre-blocking with surfen reduces uptake of the fusion polypeptide by 80%. This indicates that HS plays a role in the uptake of the fusion polypeptides.

Example 4

Figure 9A:
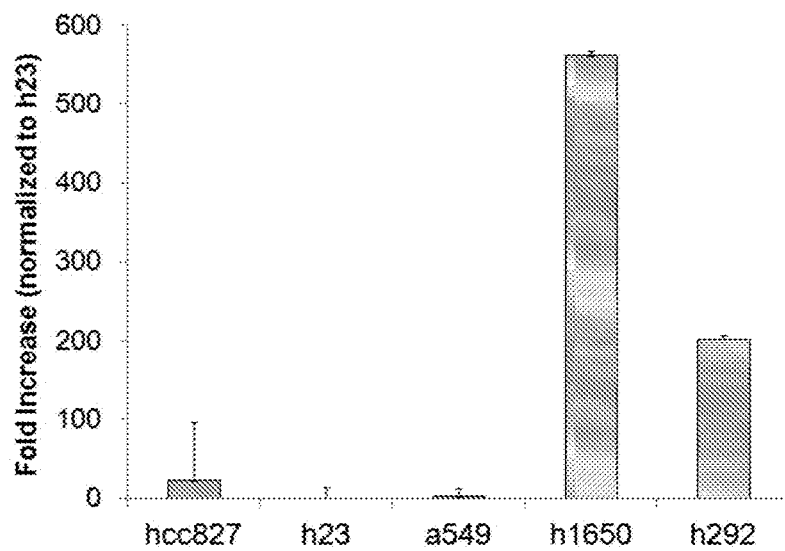
FIGS. 9A and 9B demonstrate the relative gene expression (FIG. 9A) of keratinocyte growth factor receptor (KGFR) in HCC827, H23, A549m, H1650, fibroblasts, and H292 cells. The no template (NT) is the negative control. qPCR products were confirmed by agarose gel electrophoresis. Results demonstrate the expected 135 bp PCR product (FIG. 9B).
Figure 9B:
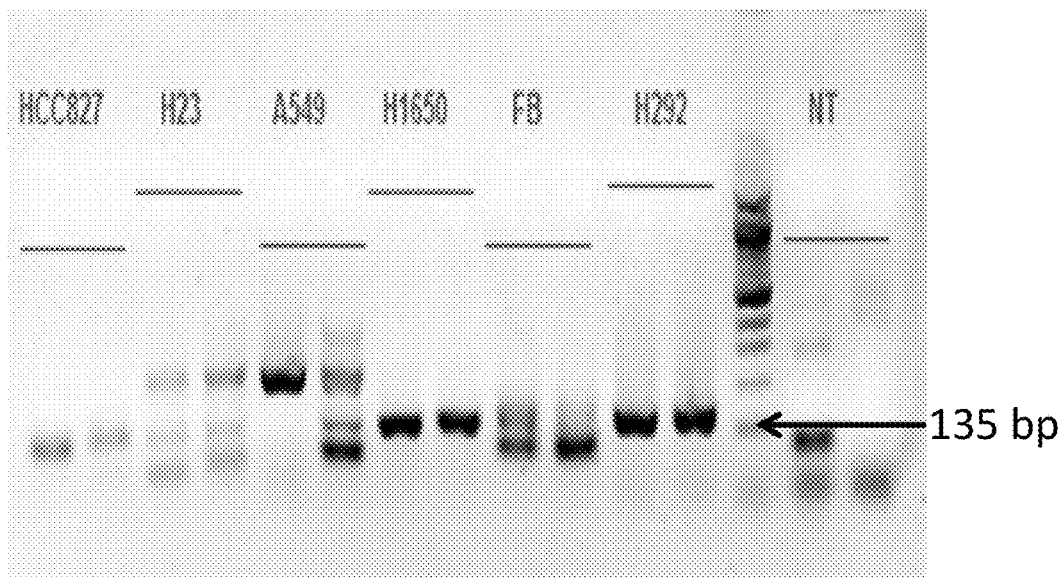

Differential Expression of Keratinocyte Growth Factor Receptor in Cell Lines mRNA expression of the human keratinocyte growth factor receptor was examined in lung cancer cell lines (hcc827, h23, a549, h1650, and h292). Expression of human keratinocyte growth factor receptor was analyzed using qPCR. The forward primer sequence for detecting KGFRiiib in all cells except fibroblasts is according to SEQ ID NO: 39. The forward primer for detecting KGFRiiic in fibroblasts is according to SEQ ID NO: 40. The reverse primer used in all cells to detect KGFRiiib and KGFRiiic is according to SEQ ID NO: 41. FIG. 9A shows the fold increase in RNA expression of the human keratinocyte growth factor receptor in various lung cancer cell lines. Data was normalized to RNA expression observed in the h23 cell line. qPCR products were confirmed using agarose gel electrophoresis. As shown in FIG. 9B, a 135 bp PCR product corresponds to a human keratinocyte growth factor receptor.

Example 5

Keratinocyte Growth Factor Increases Uptake of Cargo Carrying Nanoparticles

To determine if inclusion of keratinocyte growth factor increase uptake of the cargo carrying nanoparticles, cells H292 cells were treated with nanoparticles made from (KLAKLAK)$_2$-ELP fusion polypeptides, nanoparticles assembled from (KLAKLAK)$_2$-ELP fusion polypeptides and keratinocyte growth factor (GF)-ELP fusion polypeptides, or nanoparticles assembled from ELP and (KLAKLAK)$_2$-ELP fusion polypeptides. GF-ELP fusion polypeptides were generated from a nucleic acid encoding an keratinocyte growth factor and a nucleic acid encoding an ELP according to methods described herein.

After the fusion polypeptides were generated, 2×10$^5$ cells H292 cells per well were seeded onto cell culture plates and treated with formulations containing 50 μM of the (KLAKLAK)$_2$-ELP fusion polypeptides, 50 μM of GF-ELP fusion polypeptides, or 50 μM of ELP. Additionally, each formulation was mixed with 1.5 μM of FITC labeled-(KLAKLAK)$_2$-ELP fusion polypeptides. Cells were treated with the formulations for about 24 hours. After treatment, cells were treated with trypan blue prior to analysis by flow cytometry in order to capture only internalized particles.

Figure 10:
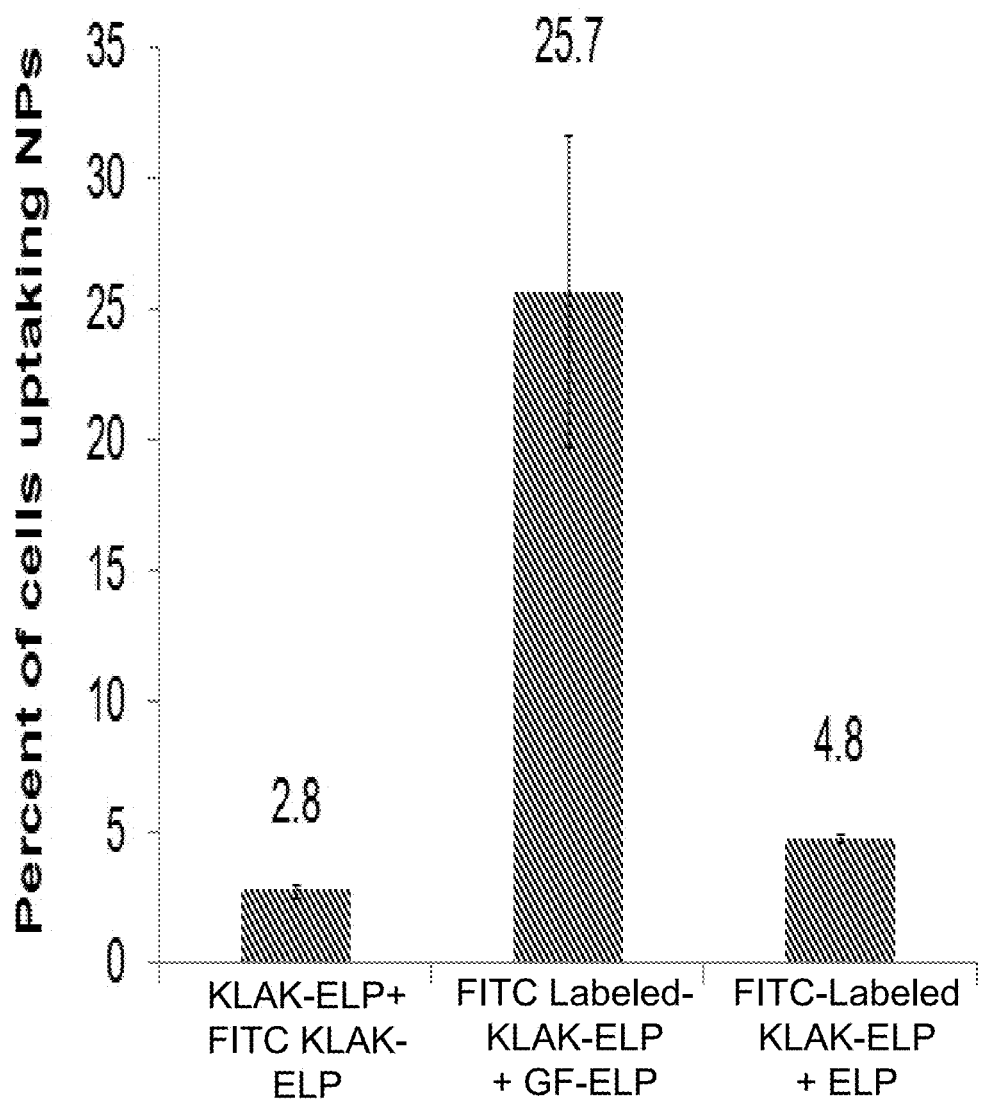
FIG. 10 demonstrates the effect of a targeting subunit on cellular uptake of cargo carrying nanoparticles.

FIG. 10 demonstrates the results from the flow cytometry analysis. The results in FIG. 10 indicate that the presence of the keratinocyte growth factor in the cargo carrying nanoparticles increases the uptake of the cargo carrying nanoparticles.

Example 6

Growth Factor-ELP Fusion Polypeptides Increase Cell Death

To determine if the increase in uptake of the cargo carrying nanoparticles by inclusion of a growth factor observed in Example 5 would translate in an increase in cell death, H292 cells were treated with three formulations containing cargo carrying nanoparticles or a control for about 24 hours. A live/dead cell viability assay where green fluorescence indicates a live cell and red fluorescence indicates a dead cell was performed to assess cell death. Results were analyzed by fluorescent microscopy.

Figure 11A:
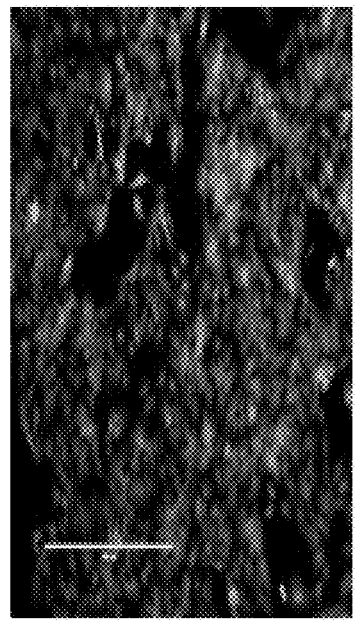
FIGS. 11A-11D demonstrate the effect of a growth factor targeting moiety in improving the cytotoxic effect of a lytic peptide. Cells were treated with a control (FIG. 11A), 50 µM of a lytic-ELP fusion polypeptide (FIG. 11B), 50 µM of a lytic-ELP fusion polypeptide and 100 µM of a growth factor-ELP fusion polypeptide (FIG. 11C), or 50 µM of a lytic-ELP fusion polypeptide and 200 µM of a growth factor-ELP fusion polypeptide (FIG. 11D).
Figure 11B:
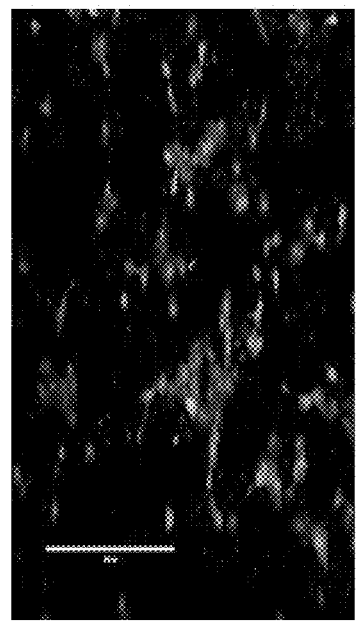
Figure 11C:
Figure 11D:

FIGS. 11A-11D show representative images generated by fluorescent microscopy of the treated cells. FIG. 11A shows a representative image of cells treated with a negative control (Untreated cells) FIG. 11B shows a representative image of cells treated with 50 μM of (KLAKLAK)$_2$-ELP fusion polypeptides. FIG. 11C shows a representative image from cells treated with 50 μM of (KLAKLAK)$_2$-ELP fusion polypeptides and 100 μM of GF-ELP fusion polypeptides (See Example 5). FIG. 11D shows a representative image from cells treated with 50 μM (KLAKLAK)$_2$-ELP and 200 μM of GF-ELP fusion polypeptides. As shown in FIGS. 11A-11D, a greater death rate was observed when the cargo carrying nanoparticles contained GF-ELP fusion polypeptides.

Example 7

Self-Assembly of Fusion ELP Polypeptides into Cargo Carrying Nanoparticles and Induction of Cell Death by Cargo Carrying Nanoparticles Epidermal growth factor receptor (EGFR) is a target for development therapeutics for treatment of lung cancer. EGFR is ubiquitously expressed and thus may not address issues with systemic treatments as treatment may also stimulate EGFRs expressed in normal tissue. EGFR specifically binds epidermal growth factor (EGF). However, EGFR can offer an advantage in instances where systemic delivery of a cargo molecule is desired.

Keratinocyte growth factor receptor (KGFR) is up-regulated in lung cancer tumors. As demonstrated in Example 4, KGFR is differentially expressed across several lung cancer cell lines. Compared to EGFR, KGFR is not ubiquitously expressed. Targeting the KGFR can result in reduced systemic toxicity resulting from ubiquitously delivered therapeutic agents, particularly chemotherapeutics. KGFR can offer an advantage in instances where systemic delivery of a cargo molecule is undesirable.

Figure 12:
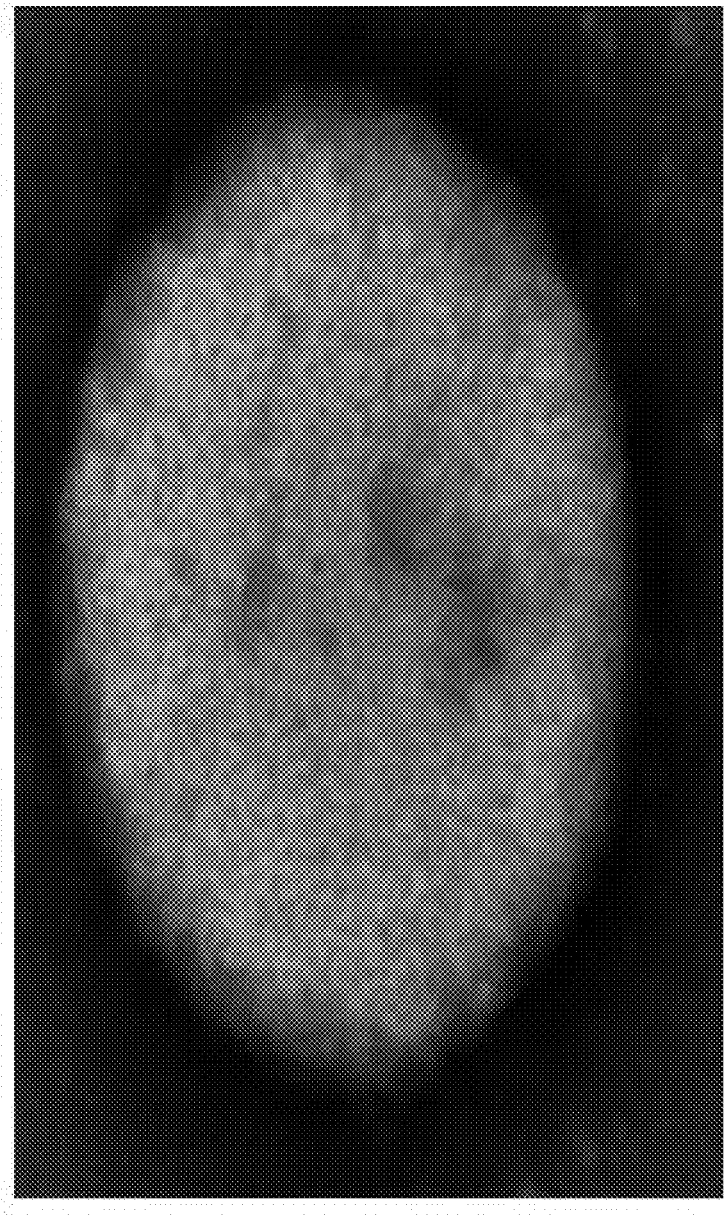
FIG. 12 shows a TEM image of an assembled cargo carrying nanoparticle.

Fusion polypeptides have been generated that contain KGF fused to an ELP. Also, fusion polypeptides have been generated that contain EGF fused to an ELP. In solution, the fusion polypeptides can self-assemble into nanoparticles at the $T_{tm}$. FIG. 12 shows a TEM image of an assembled nanoparticle made from KGF-ELP fusion polypeptides. The nanoparticle shown in FIG. 12 has a diameter of about 500 nm.

Figure 13:
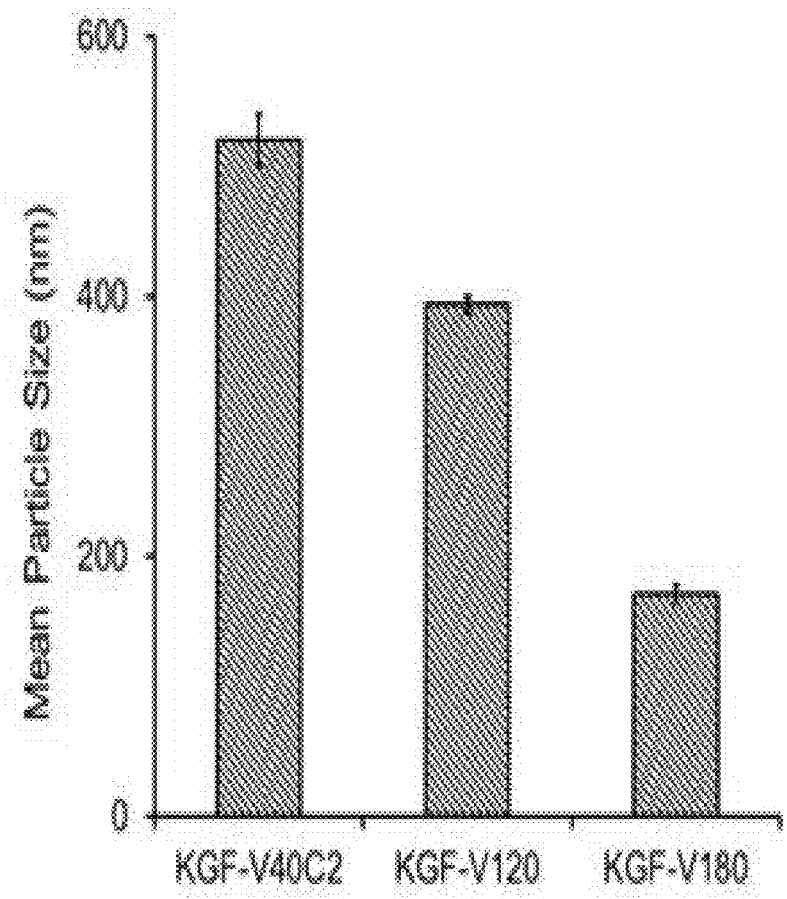
FIG. 13 demonstrates the effect of hydrophobicity of the ELP in the nanoparticle subunits on nanoparticle size.

Smaller nanoparticles, particularly those less than about 100 nm in diameter are more efficacious for in vivo delivery of cargo molecules. The hydrophobicity of the ELP domain of the fusion polypeptides can be manipulated. To determine if the hydrophobicity of the ELP domain effects the size of the resulting nanoparticles, KGF-ELP fusion polypeptides were generated using different ELPs (V40C2, V120, and V180) that vary in their hydrophobicity. Hydrophobicity of V40C2 is less than V120, which is less than the hydrophobicity of V180. The cDNA sequence of V180 is according to SEQ ID NO: 36, which encodes the V180 polypeptide having a sequence according to SEQ ID NO: 37. The cDNA sequence of V120 is according to SEQ ID NO: 38. As shown in FIG. 13, increasing the hydrophobicity of the ELP domain of the fusion polypeptides resulted in smaller nanoparticles. Nanoparticle size was assessed by dynamic light scattering.

Figure 14A:
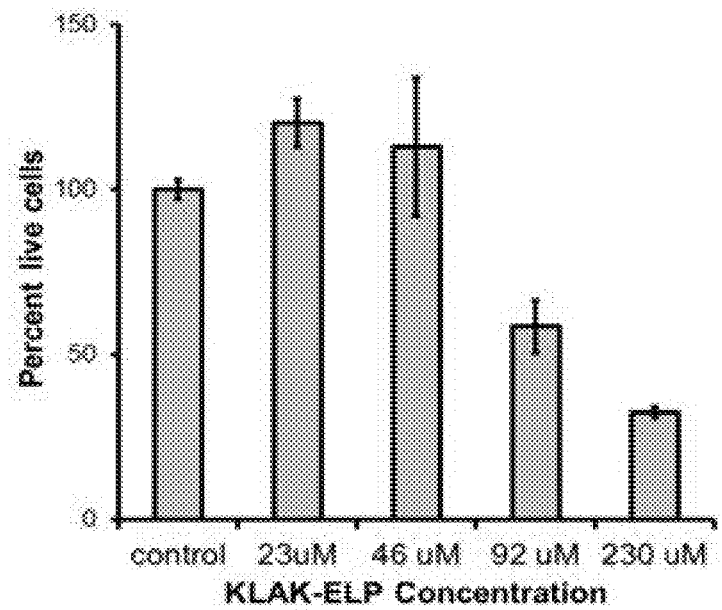
FIGS. 14A and 14B demonstrate the effect of increasing concentrations of either $(KLAKLAK)_2$-ELP nanoparticles (FIG. 14A) or $(KLAKLAK)_2$ peptides (FIG. 14B) on cancer cell viability in vitro. $KLAKLAK_2$ is also referred to herein as KLAK.
Figure 14B:
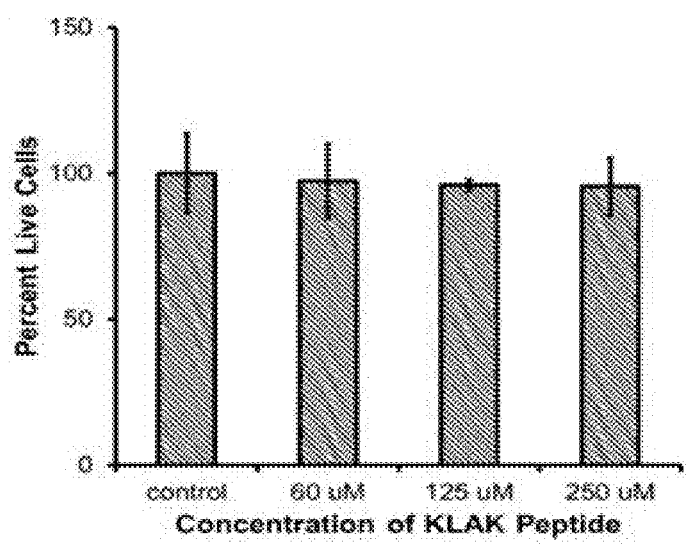

2×10$^5$ cancer cells (H292 cells) were treated for about 24 hours with nanoparticles assembled from (KLAKLAK)$_2$-ELP fusion polypeptides or (KLAKLAK)$_2$ peptides and fraction of live cells were quantified. FIGS. 14A and 14B demonstrates the percent cell viability of cancer cells treated with nanoparticles assembled from (KLAKLAK)$_2$-ELP fusion polypeptides (FIG. 14A) or (KLAKLAK)$_2$ peptides (FIG. 14B). As demonstrated in FIG. 14A, it was observed that nanoparticles assembled from (KLAKLAK)$_2$-ELP fusion polypeptides induced cell death in a dose dependent manner. In contrast, (KLAKLAK)$_2$ peptides by themselves, when used at comparable concentrations, were not observed to induce cell death. Thus, the data suggest that not only the bioactivity of (KLAKLAK)$_2$ is maintained in the fusion polypeptide, but also the assembly of (KLAKLAK)$_2$-ELP nanoparticles increases the internalization of (KLAKLAK)$_2$, which likely led to the observed increase in cell death.

Figure 15:
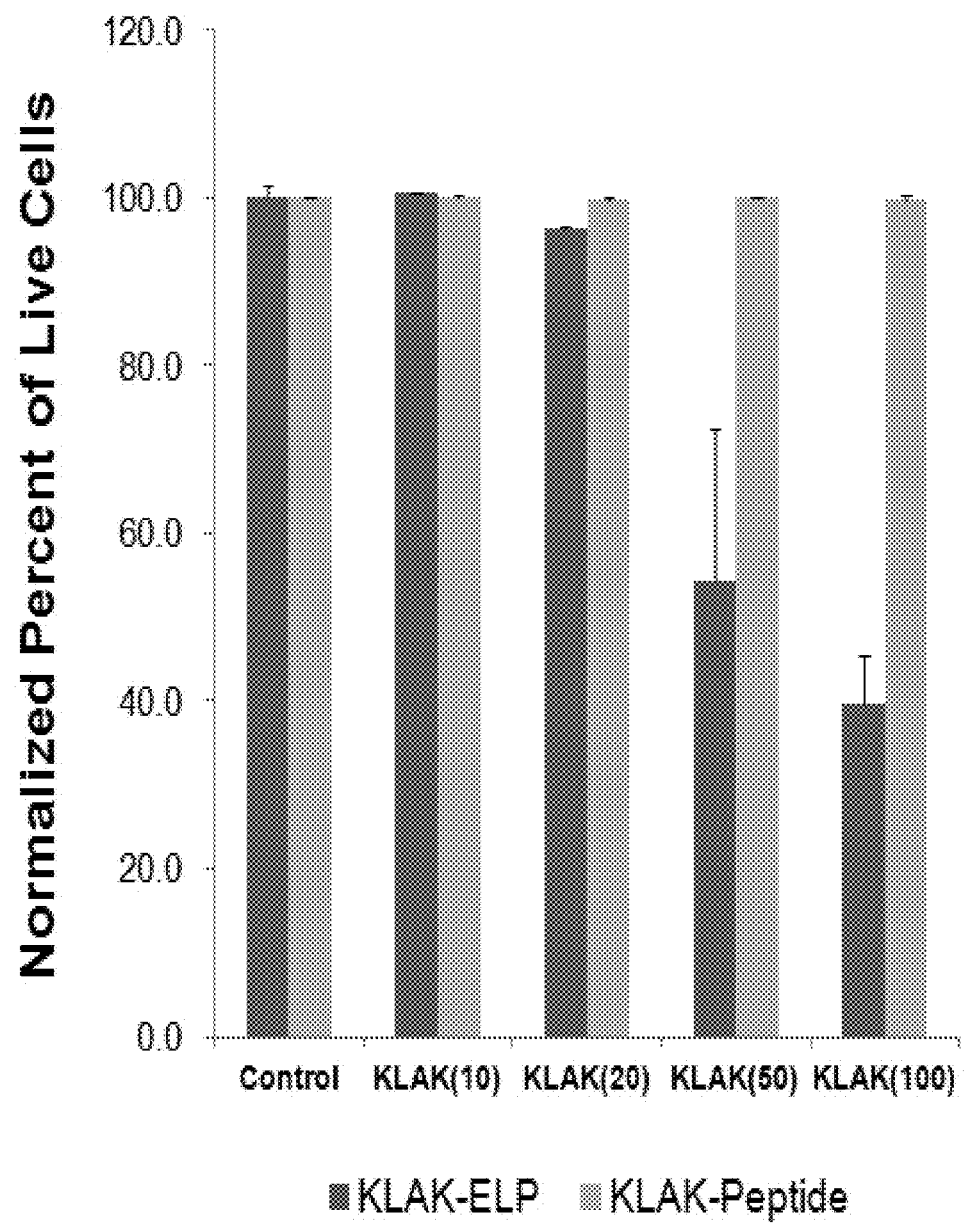
FIG. 15 demonstrates the effect of increasing concentrations of either $(KLAKLAK)_2$-ELP nanoparticles or $(KLAKLAK)_2$ peptides on lung cancer cell (A549) viability in vitro.

Supporting the previously discussed data, FIG. 15 demonstrates a dose dependent increase in cell death in lung cancer cells (A549 cells) treated with increasing concentrations (10 μM "KLAK(10)," 20 μM "KLAK(20)," 50 μM "KLAK(50)," and 100 μM "KLAK(100)") of (KLAKLAK)$_2$-ELP nanoparticles or (KLAKLAK)$_2$ peptides alone.

Additionally, the (KLAKLAK)$_2$-ELP nanoparticles were observed to induce mitochondrial depolarization as shown in FIGS. 16A-16C. Lung cancer cells (A549) were treated with a negative control (cells treated with JC-1 only) a positive control (CCCP), or 25 μM of (KLAKLAK)$_2$-ELP peptides.

Figure 17:
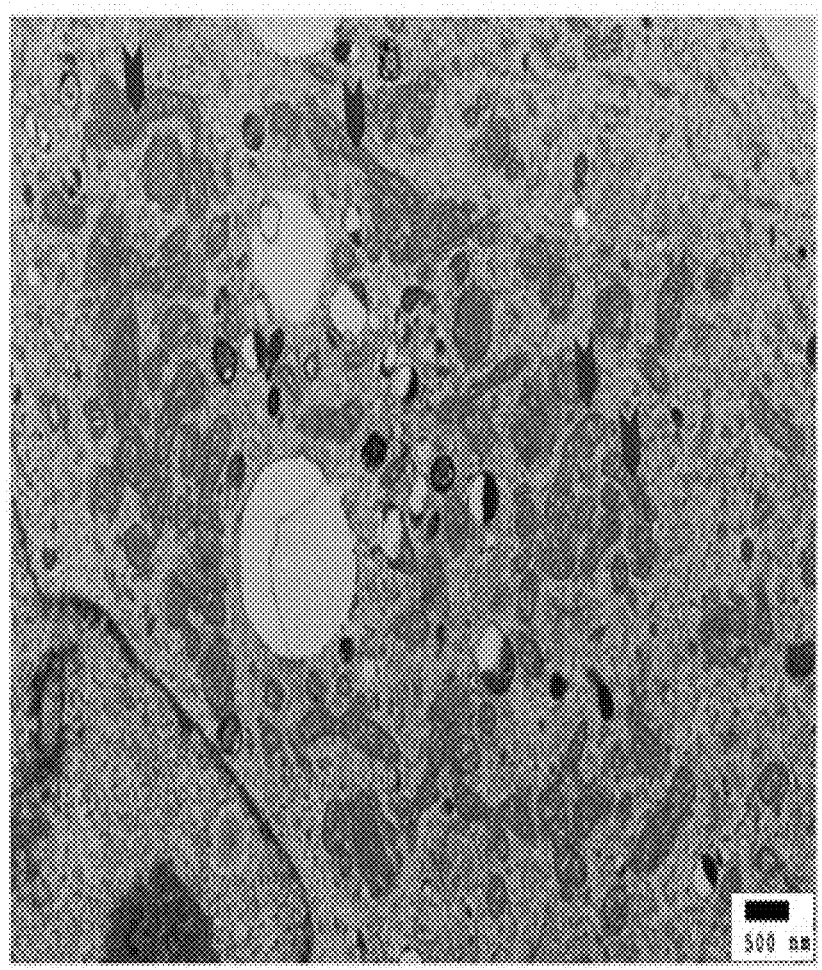
FIG. 17 shows a TEM image of a cell treated with $KLAKLAK_2$-ELP nanoparticles demonstrating mitochondrial swelling (arrows).

Red shows intact mitochondria while green shows depolarized mitochondria. About all of the cells treated with the negative control had intact mitochondria whereas at least about 90% of the cells treated with the positive control had depolarized mitochondria. About 70% of the cells treated with the (KLAKLAK)$_2$-ELP peptides had depolarized mitochondria. FIG. 17 shows a TEM image of a cell treated with 50 μM (KLAKLAK)$_2$-ELP peptides. Arrows indicate swollen mitochondria, which suggest that these mitochondria were depolarized and demonstrate damage to the mitochondrial membranes.

To further quantify the damage to the mitochondrial membranes, a JC-1 assay was used to measure mitochondrial membrane potential. JC-1 dye exhibits membrane-potential dependent accumulation in mitochondria, indicated by a fluorescence emission shift from green (~529 nm) to red (~590 nm). A decrease in the red/green fluorescence intensity ratio, as measured by flow cytometry, indicates mitochondrial depolarization. FIGS. 18A-18B shows the results of the JC-1 assay, which support the visual indications of mitochondrial depolarization. FIG. 18A shows the results of a JC-1 assay performed on cells treated with a negative control. FIG. 18B shows the results of a JAC-1 assay performed on cells treated with (KLAKLAK)$_2$-ELP peptides. Non-apoptotic and apoptotic regions are marked.

Example 8

Figure 19:
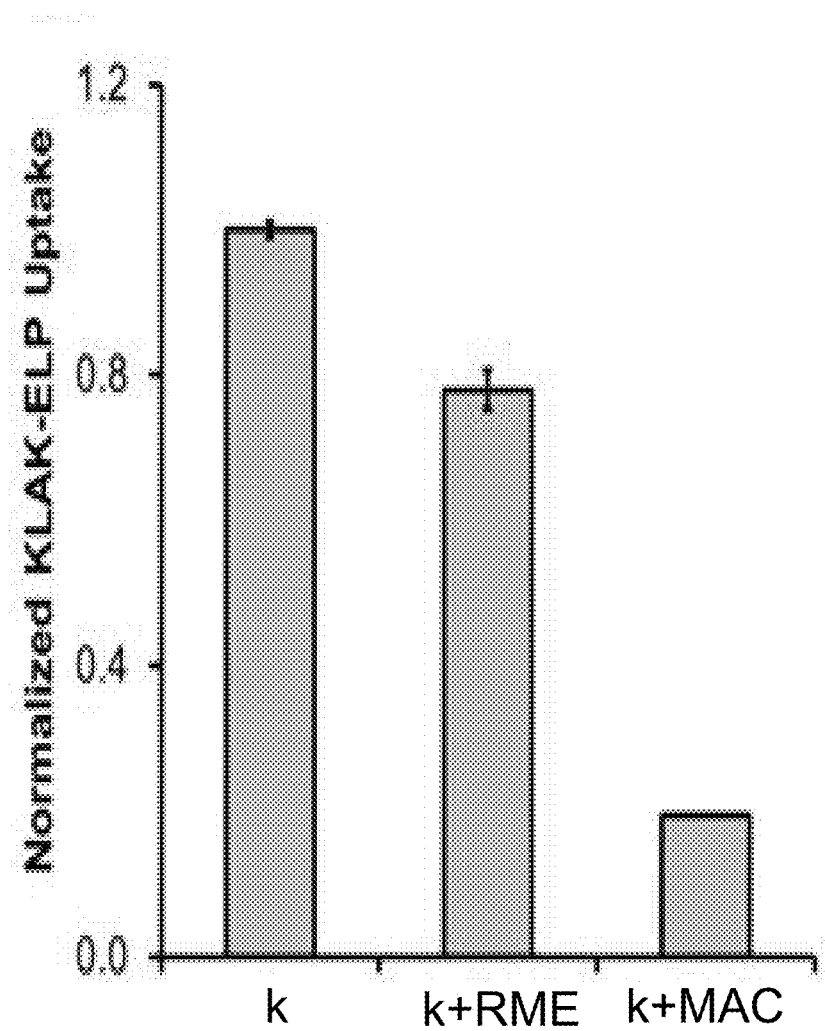
FIG. 19 demonstrates the effect of cargo carrying nanoparticle (k) uptake in cells treated with a blocker of receptor mediated endocytosis (RME) or a blocker or macropinocytosis (MAC).

Uptake of (KLAKLAK)$_2$-ELP Cargo Carrying Nanoparticles is Via Macropinocytosis and Involves Heparan Sulfate Using inhibitors of receptor mediated endocytosis (RME, chloropromazine) and macropinocytosis (MAC, amiloride) it was observed that (KLAKLAK)$_2$-ELP (k) cargo carrying nanoparticles were taken up by cells predominantly by macropinocytosis (FIG. 19). Briefly, c H292 cells were treated with (KLAKLAK)$_2$-ELP peptides, which self-assembled into cargo carrying nanoparticles, cargo carrying nanoparticles and an RME inhibitor (k+RME), or cargo carrying nanoparticles and a MAC inhibitor (k+MAC). Uptake/cell was then measured and normalized. Uptake was measured by flow cytometry and the results were normalized to the k treatment.

Figure 20:
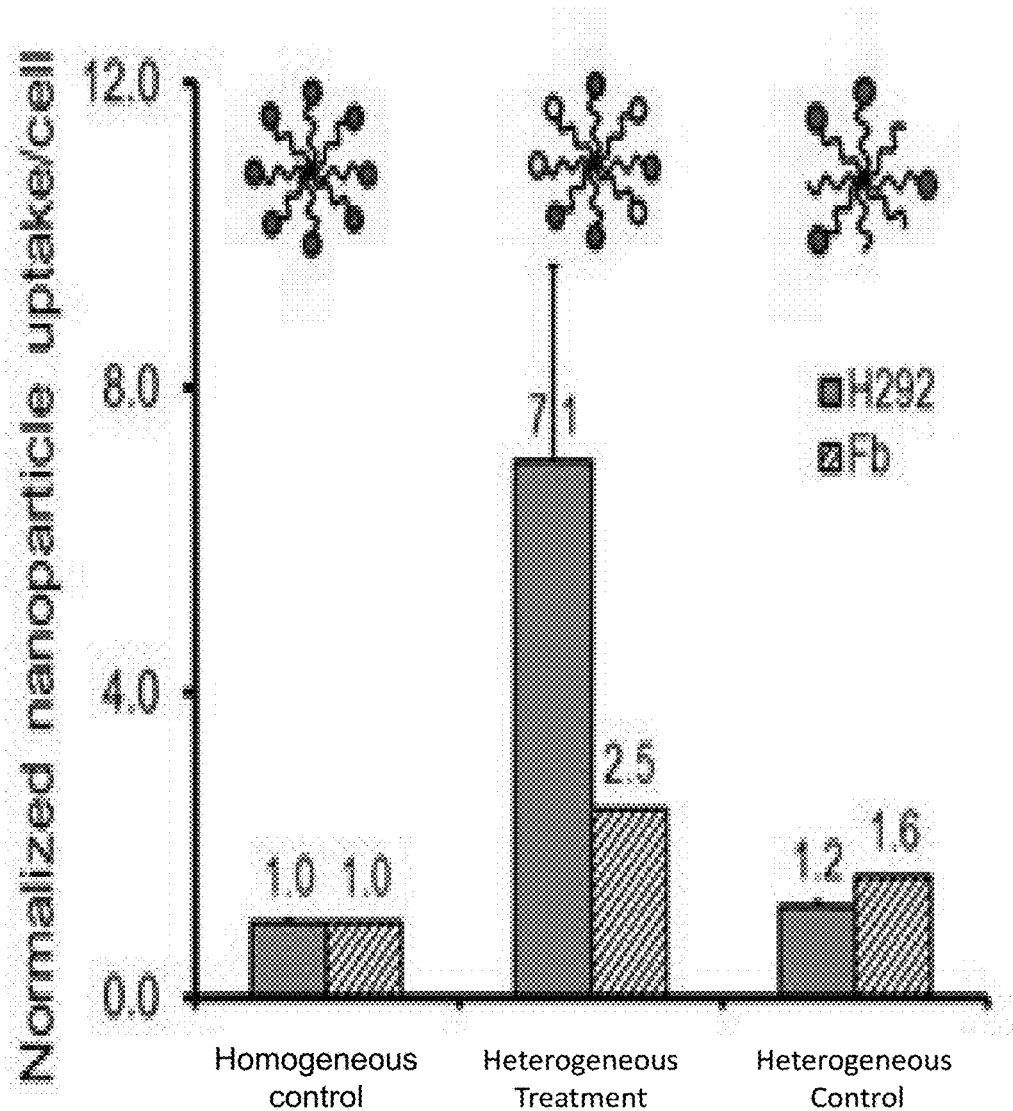
FIG. 20 demonstrates the quantitation of heterogeneous cargo carrying nanoparticle uptake per cell for H292 or fibroblasts (fb). Cells were treated with nanoparticles made of $(KLAKLAK)_2$-ELP nanoparticles (homogeneous control), nanoparticles containing $(KLAKLAK)_2$-ELP subunits and Growth factor (GF)-ELP subunits (heterogeneous treatment), or nanoparticles containing $(KLAKLAK)_2$-ELP subunits and ELP alone (heterogeneous control).

To determine if the addition of a growth factor to the cargo carrying nanoparticles, KGF-ELP fusion peptides as well as (KLAKLAK)$_2$-ELP peptides were used as the building blocks for the cargo carrying nanoparticles and uptake was evaluated. Briefly, lung cancer cells (H292) or fibroblasts (Fb) were treated with cargo carrying nanoparticles made from (KLAKLAK)$_2$-ELP peptides alone (Homogenous control), cargo carrying nanoparticles made from (KLAKLAK)$_2$-ELP peptides and about KGF-ELP peptides (Heterogeneous treatment), or cargo carrying nanoparticles made from (KLAKLAK)$_2$-ELP peptides and about 50 μM ELP peptides alone (Heterogeneous control). The concentrations of peptides used was about 2.5 uM (KLAKLAK)$_2$, about 50 μM of KGF-ELP, and about 50 μM of ELP. Uptake was measured using flow cytometry and the results were normalized to the homogeneous treatment. As shown in FIG. 20, inclusion of the KGF-ELP peptide increased uptake in the H292 cells, which have a greater expression of the KGF receptor than the Fb cells. These data suggest that inclusion of a targeting moiety, such as KGF, can increase uptake of the cargo carrying nanoparticles in a selective and specific manner.

Figure 21:
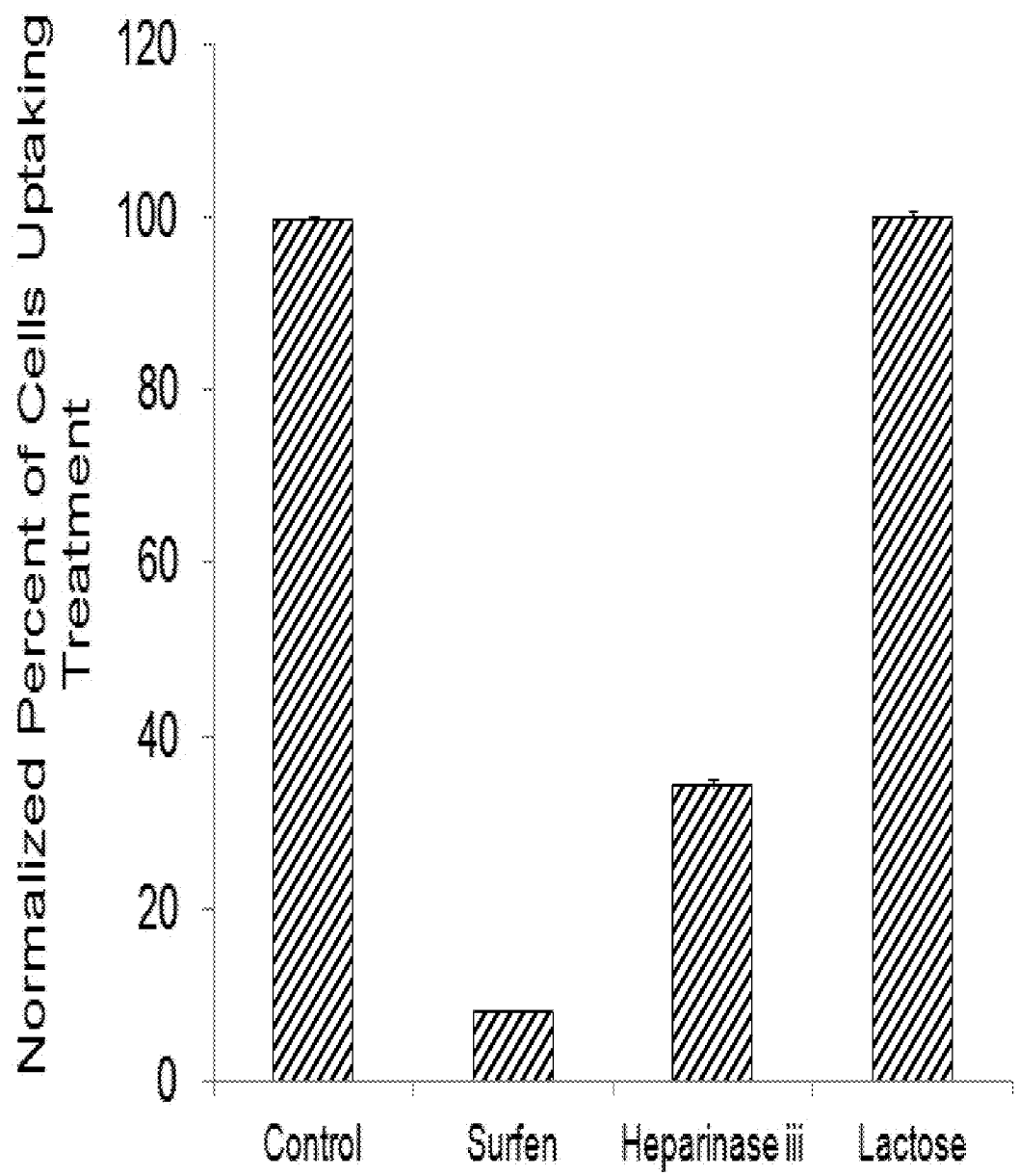
FIG. 21 demonstrates the effect of cell surface protein blockers (Surfen, Heparinase iii, or lactose) on the uptake of the cargo carrying nanoparticles.

To determine which molecule(s) on the cell surface was interacting with the (KLAKLAK)$_2$-ELP peptides, H292 cells were treated with cargo carrying nanoparticles containing (KLAKLAK)$_2$-ELP peptides after pretreating cells with a control (cells that were treated with (KLAKLAK)$_2$-ELP but not pretreated with any of the blockers), surfen, heparinase iii, or lactose. Surfen specifically binds to heparan sulfate on the cell surface, heparinase iii cleaves off heparan sulfate on the cell surface, and lactose blocks the elastin receptor complex (ERC). As shown in FIG. 21, the results suggest that heparan sulfate interacts with the (KLAKLAK)$_2$-ELP peptide at the cell surface.

Figure 22:
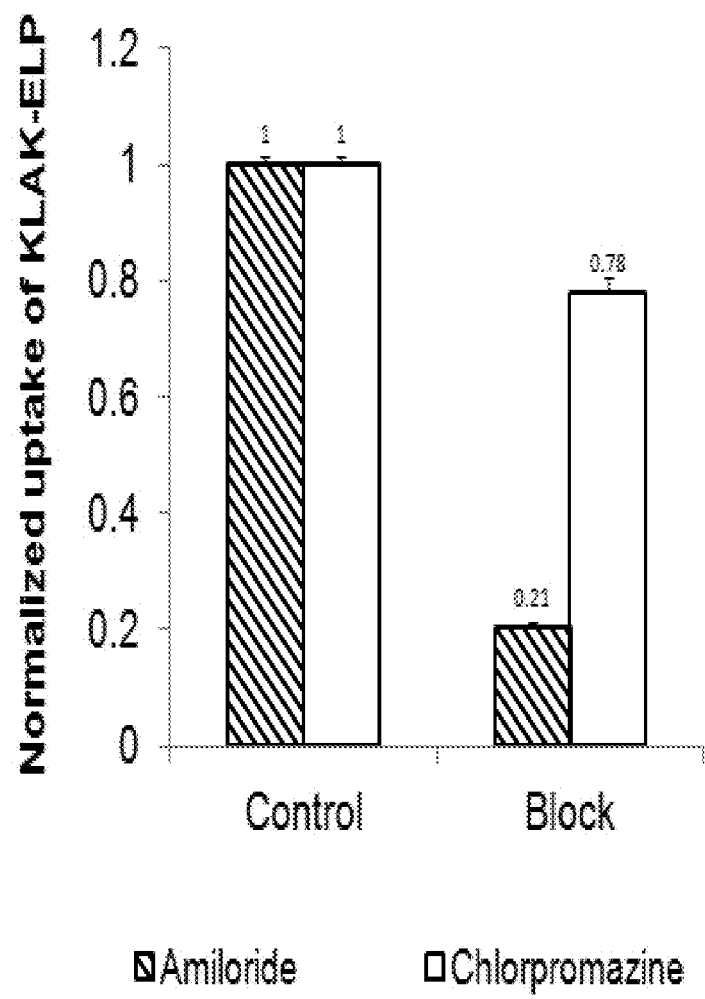
FIG. 22 demonstrates the effect of MAC or RME blockers on the uptake of cargo carrying nanoparticles.

Supporting previously discussed results, FIG. 22 demonstrates that macropinocytosis is the main pathway of internalization of the cargo carrying nanoparticles. Briefly, (H292 cells were pretreated with amiloride (blocks MAC) or chlorpromazine (blocks RME) and uptake of (KLAKLAK)$_2$-ELP cargo carrying nanoparticles was measured, normalized, and compared to uptake of (KLAKLAK)$_2$-ELP cargo carrying nanoparticles in un-treated cells. Uptake was measured using flow cytometry. The control were the cells that were treated with (KLAKLAK)$_2$-ELP but were not pre-blocked with amiloride or chlorpromazine Killing efficiency of the cargo carrying nanoparticles made from (KLAKLAK)$_2$-ELP peptides (klak) and KGF-ELP (KGF) peptides was evaluated. Briefly, H292 were treated with a control (FIG. 23A) Untreated cells served as a control. 50 μM of klak (FIG. 23B), 50 μM of klak and 100 μM of KGF (FIG. 23C), or 50 μM of klak and 200 μM of KGF (FIG. 23D). Cell death was measured by a live (green fluorescence)/dead (red fluorescence) assay. Bar=400 μm in FIGS. 23A-23D. As shown in FIG. 23A, about all of the cells were alive after treatment with the control. As shown in FIGS. 23B through 23C, the number of dead cells increased with the increasing concentration of KGF. As such, the results suggest that cargo carrying nanoparticles containing growth factors induce killing more effectively than cargo carrying nanoparticles containing only lytic fusion peptides.

Figure 24:
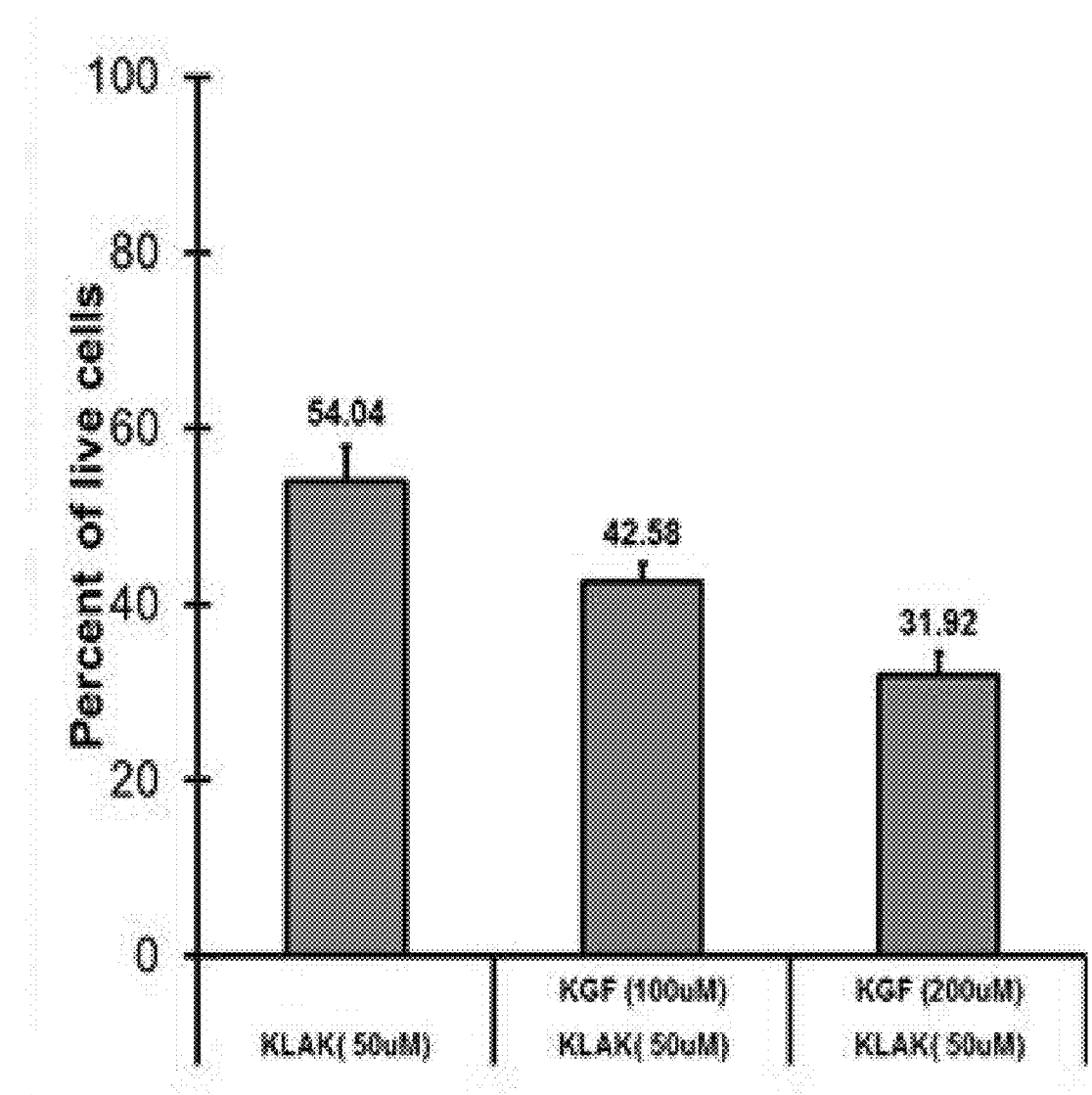
FIG. 24 demonstrates the results from quantifying the live cells after the cells were treated as in FIG. 21.

The results demonstrated in FIGS. 23A-23D are supported by the results shown in FIG. 24, which demonstrate the quantitation of live H292 cells after treatment with or 50 μM of klak, 50 μM of klak and 100 μM of KGF, or 200 μM of KGF. As shown in FIG. 24, cell viability decreased as the concentration of KGF was increased.

Example 9

Expression of KGFR iiib in Various Cells

Figure 25:
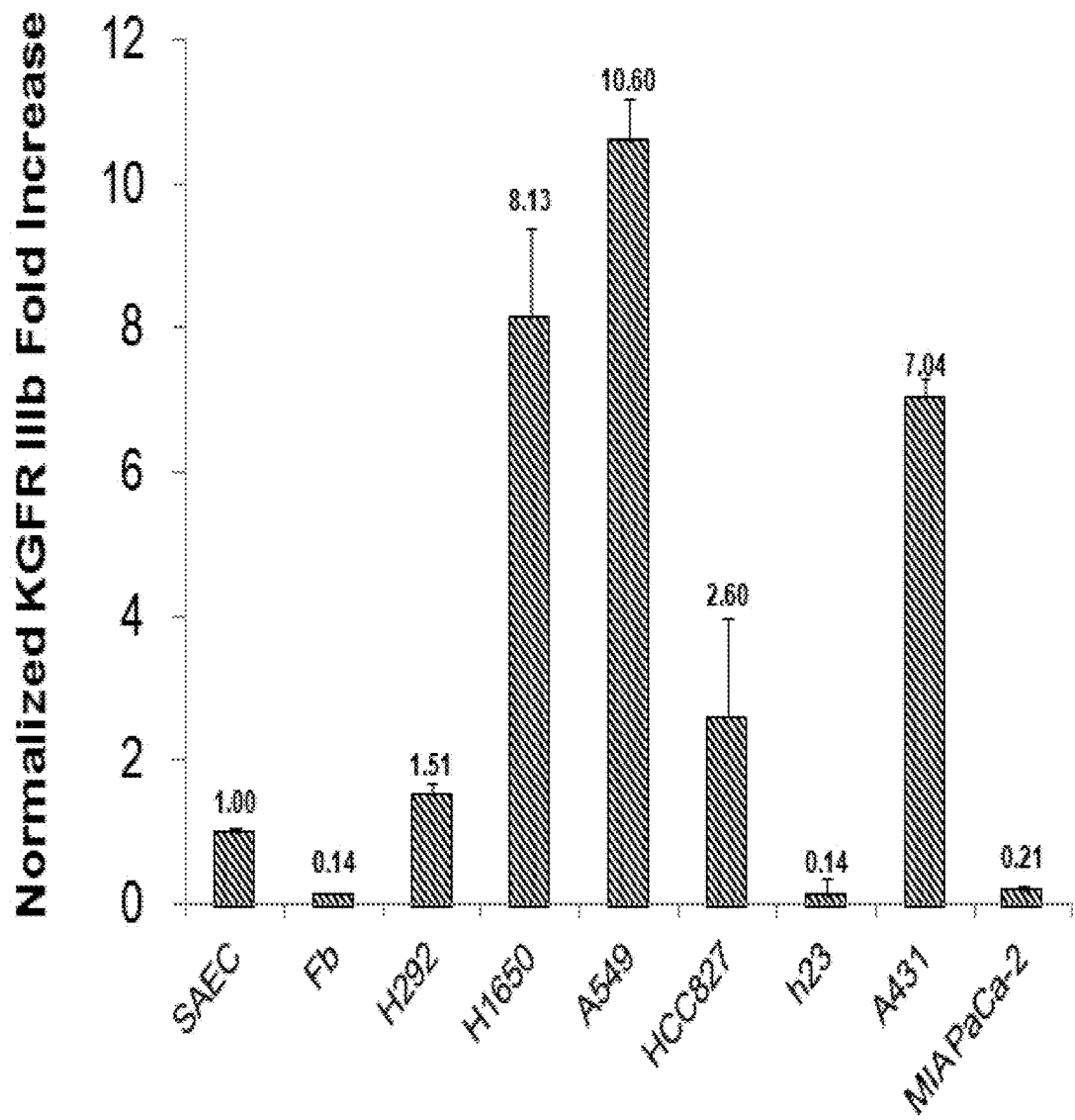
FIG. 25 demonstrates the relative gene expression of keratinocyte growth factor receptor IIIb in various cancer cell lines or fibroblast cells (fb).

Gene expression of KGFR iiib in various cell lines (SAEC, fibroblasts (fb), H292, H1650, A549, HCC827, h23, A431, MIA PaCa-2) was determined. As demonstrated in FIG. 25, KGFR iiib was differentially expressed among the various cell lines. A549 cells, a lung cancer cell line, had the greatest expression.

Example 10

Increased and Selective Internalization of Cargo Carrying Nanoparticles by KGF

Figure 26:
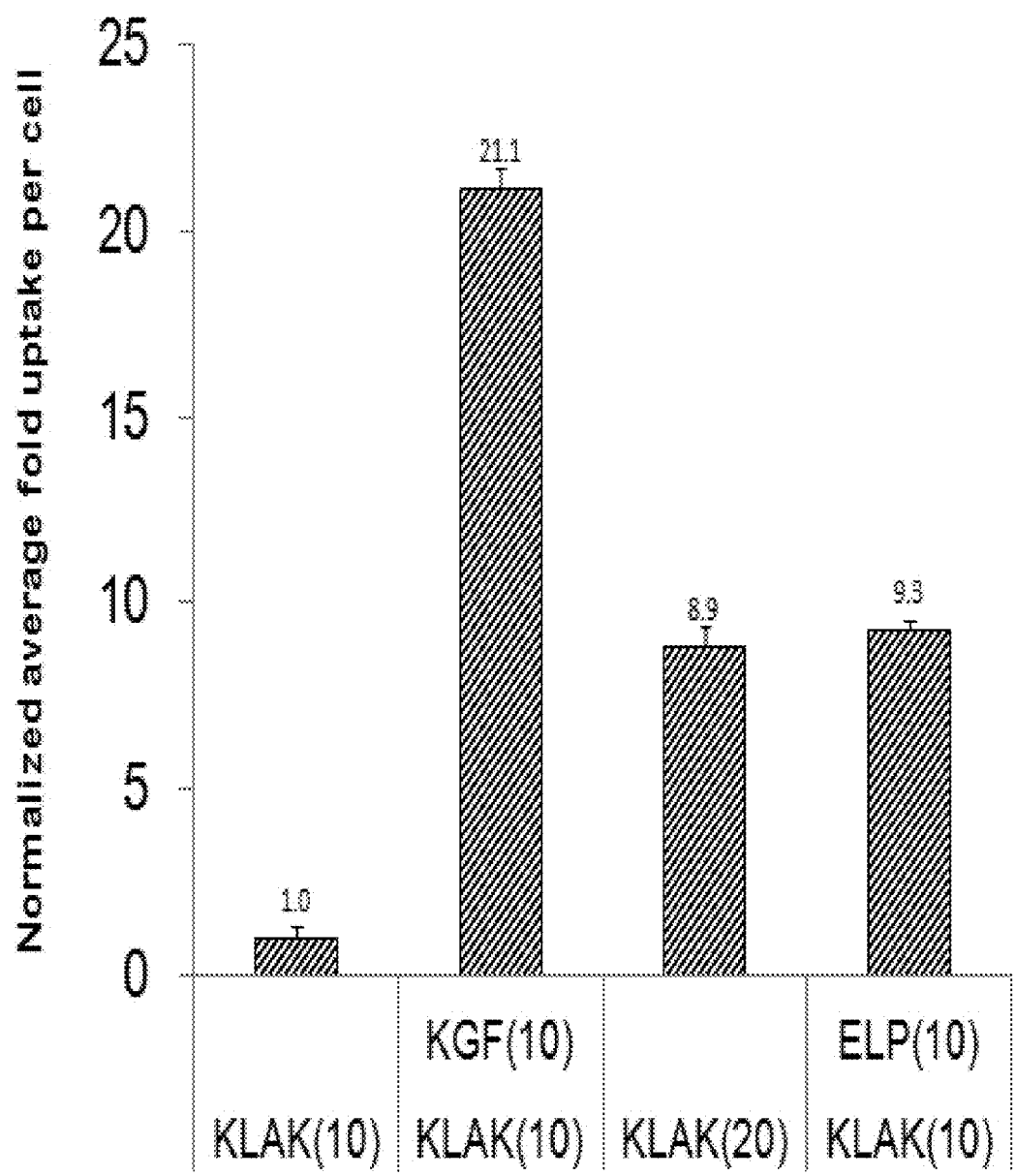
FIG. 26 demonstrates the effect of a targeting subunit containing a keratinocyte growth factor on uptake of cargo carrying nanoparticles in A549 lung cancer cells.

As shown in Example 9, A549 cells have greatest expression of KGFR iiib. A549 cells were treated with 10 μM (KLAKLAK)$_2$-ELP (KLAK), 10 μM KGF-ELP (KGF) and 10 μM KLAK, 20 μM KLAK, or 20 μM ELP and 20 μM KLAK. Uptake was measured and normalized. Uptake was measured using flow cytometry and the results were normalized to (KLAKLAK)$_2$-ELP 10 uM treatment. As shown in FIG. 26, inclusion of KGF in the cargo carrying nanoparticles increases the uptake of the cargo carrying nanoparticles by the cells.

Figure 27:
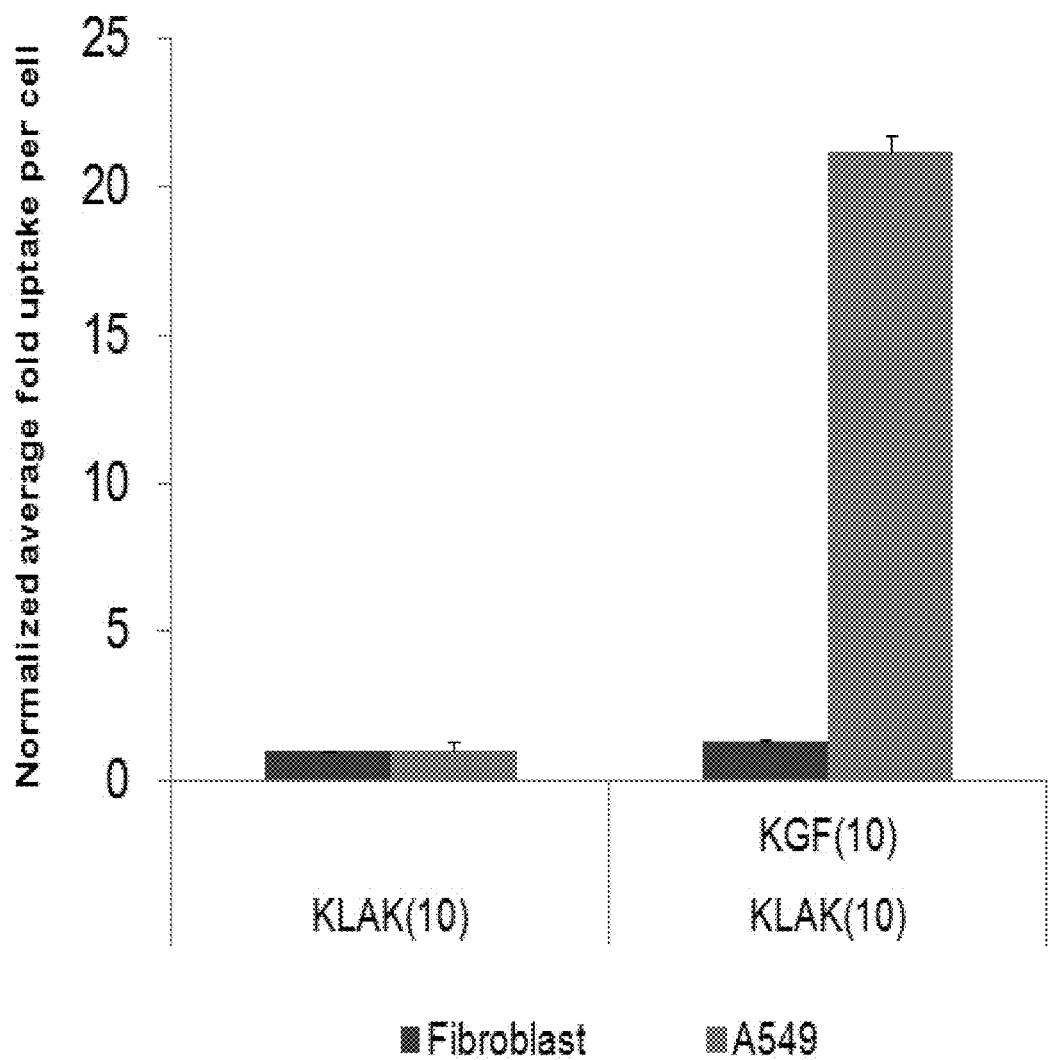
FIG. 27 demonstrates the targeting selectivity of the targeting subunit containing a keratinocyte growth factor between cells that express the keratinocyte growth factor receptor (A549 cells) and fibroblasts (fb).

To determine if the uptake induced by KGF is selective, A549 or fibroblasts, were treated with 10 µM KLAK or 10 µM KGF and 10 µM KLAK. A549 express KGFR IIIb whereas fibroblasts do not express KGFE iiib (See FIG. 25). After treatment, uptake was measured and normalized. Uptake was measured using flow cytometry and the normalization was to the KLAK(10) treatment. As shown in FIG. 27, the KFG increased uptake only in the A549 cells.

This suggests that KGF induced uptake of the cargo carrying nanoparticles is selective.

Example 11

Selective Killing of Cells by Cargo Carrying Nanoparticles Containing KGF

Figure 28:
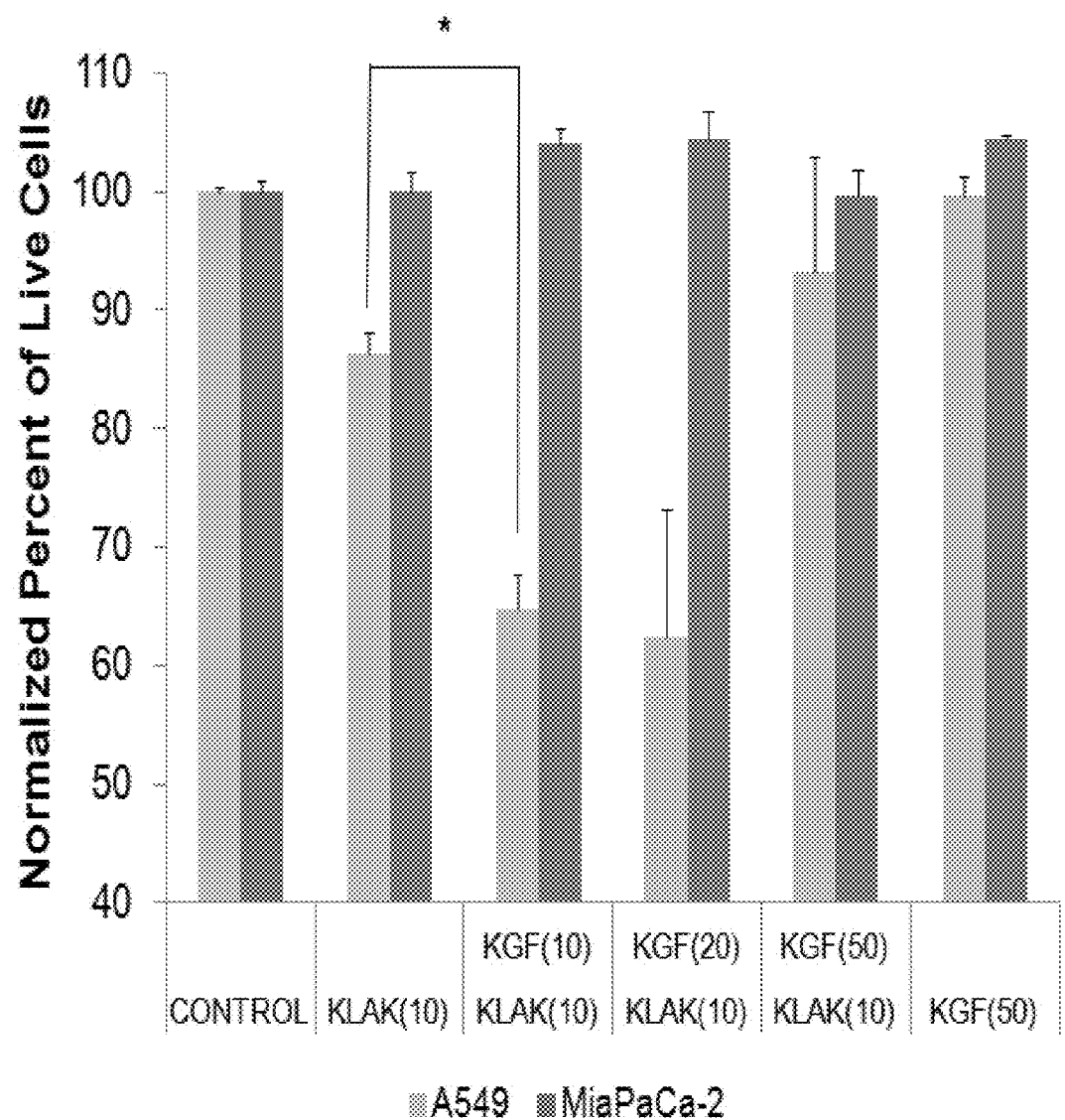
FIG. 28 demonstrates the selective killing of cells that express a keratinocyte growth factor receptor (A549) by cargo carrying nanoparticles having a targeting subunit that contains a keratinocyte growth factor as compared to cells that do not express a keratinocyte growth factor receptor (MiaPaCa-2). * indicates values that are significantly different.

To determine if killing induced by the cargo carrying nanoparticles containing KGF is selective, cells expressing high levels (A549) or low levels (MiaPaCa-2), were treated with a control Untreated cells served as a control. 10 µM KLAK, 10 µM KLAK and 10 µM KGF, 10 µM KLAK and 20 µM KGF, 10 µM KLAK and 50 µM KGF, or 50 µM KGF. The percent of live cells was measured. The percent of live cells was normalized to the percent of live cells remaining in the control. As suggested by the results shown in FIG. 28, cells expressing high levels (as compared to other cell types) KGFR iiib are killed by the combination of (KLAK-LAK)$_2$-ELP and KGF-ELP, while cells having low expression (if any), are not killed by the combination of (KLAK-LAK)$_2$-ELP and KGF-ELP.

Example 12

Figure 29:
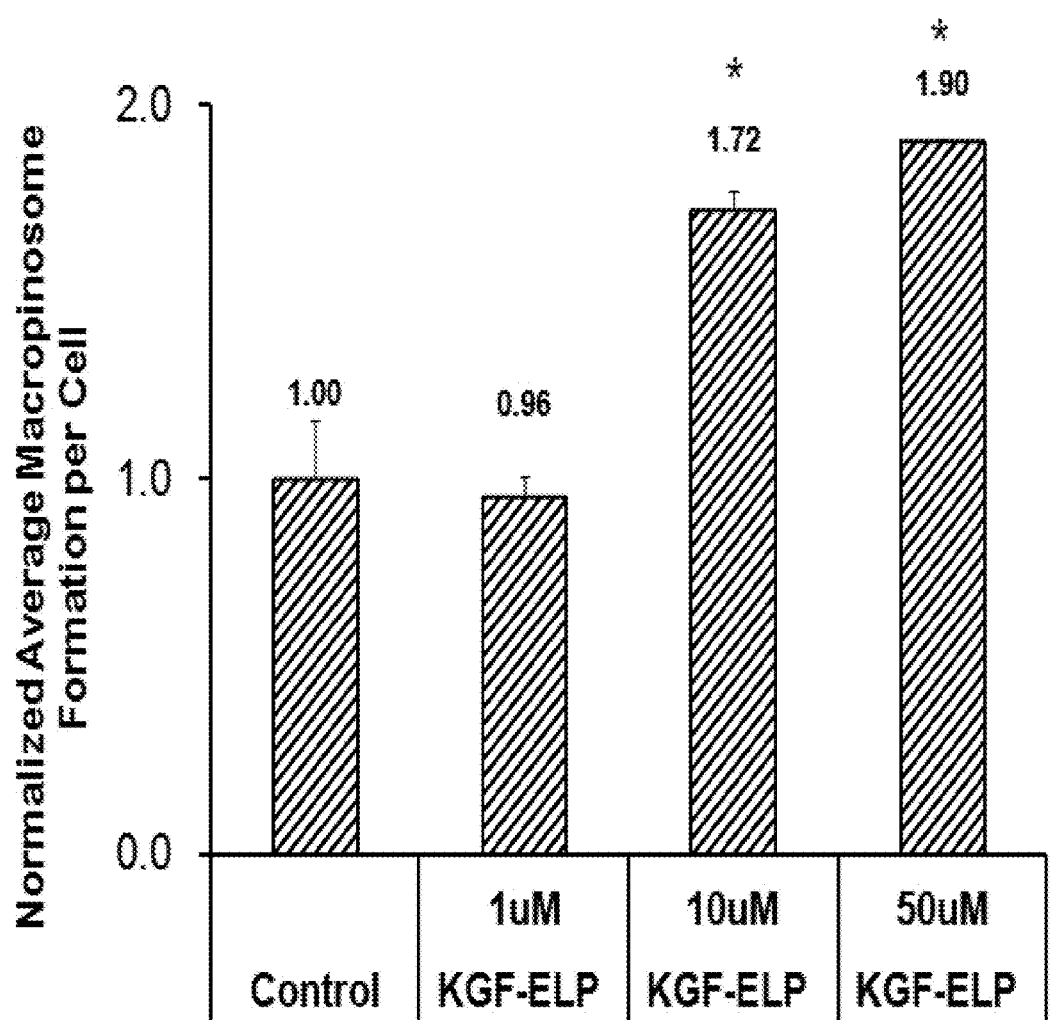
FIG. 29 demonstrates the dose-dependent effect of a targeting subunit that contains a keratinocyte growth factor on macropinosome formation in cells (A549) expressing increased levels of keratinocyte growth factor receptor iiib (KGFR).
Figure 30:
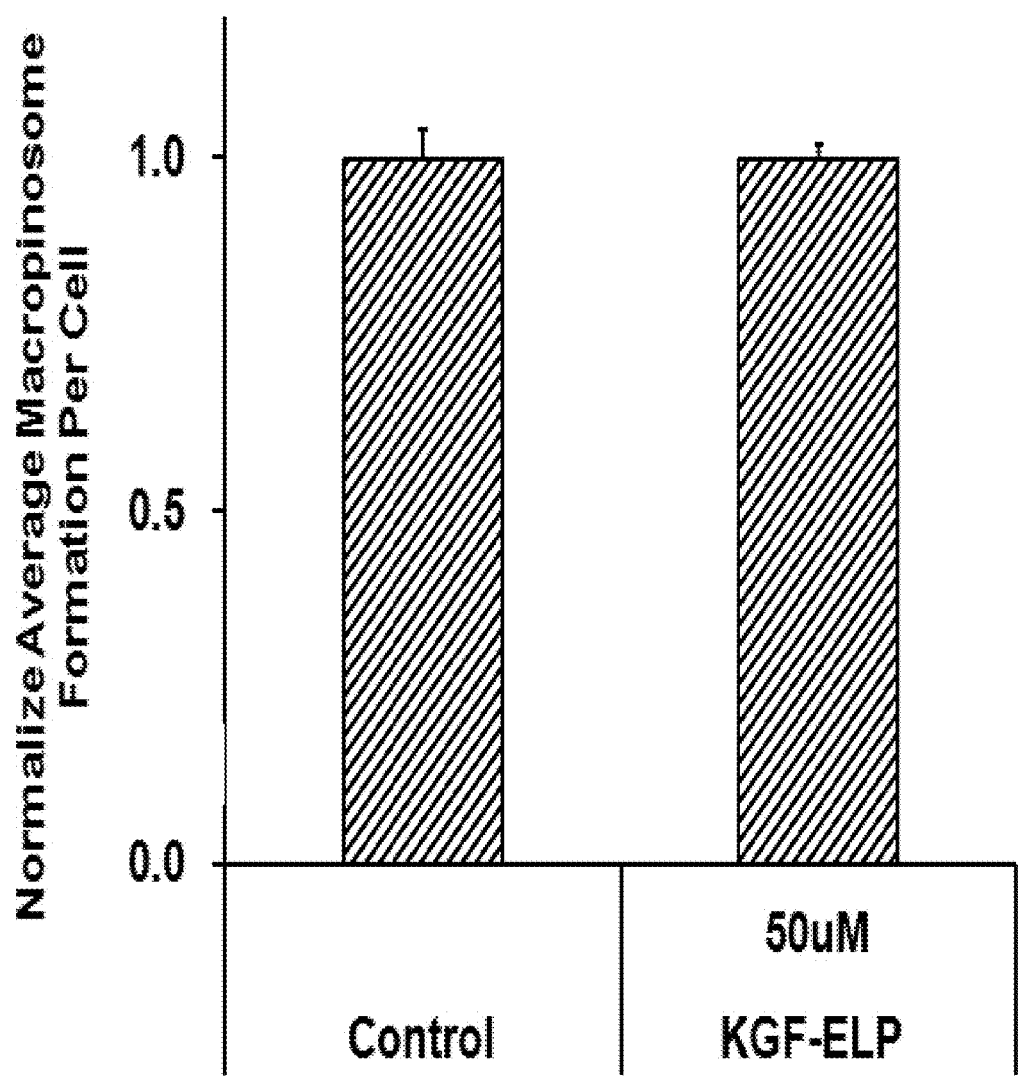
FIG. 30 demonstrates the effect of the a targeting subunit that contains a keratinocyte growth factor on macropinosome formation in cells (fb) that do not express keratinocyte growth factor receptor iiib.

Enhancement of Macropinosome Formation by Cargo Carrying Nanoparticles Containing KGF To determine the effect of KGF on the macropinocytosis pathway, macropinosome formation was evaluated in cells after treatment with a control (untreated cells) 1 µM KGF-ELP peptides, 10 µM KGF-ELP peptides, or 50 µM KGF-ELP peptides. The number of macropinosomes per cell was determined and the average number was normalized to the number of macropinosomes in the control cells, which was set to 1.0. As demonstrated by the results shown in FIG. 29, KGF-ELP peptides enhance macropinosome formation in a dose-dependent manner in A549 cells, which express KGFR iiib. As shown in FIG. 30, the enhancement in macropinosome formation was not observed in fibroblast cells, which doe not express KGFR iiib.

Example 13

Production of Heterogeneous Cargo Carrying Nanoparticles

Genes encoding recombinant growth factors (KGF or EGF) were excised from a PUC57 plasmid and cloned in frame with the gene encoding the ELP cassette $V_{40}C_2$. In the ELP cassette $V_{40}C_2$, V=VPGVG and C= (VPGVGVPGVGVPGCGVPGVGVPGVG). The "V" repeat subunit is repeated 40 times and the C repeat unit is repeated twice in this ELP. This yielded a gene encoding the building blocks (subunits) of the cargo carrying nanoparticles. These nucleic acids formed here encoded the growth factor (GF)-ELP subunits. The gene encoding the GF-ELP was then cloned into an expression plasmid (pET25b+) and was used to transform bacteria (BRL cells). The bacteria were grown at about 37° C. for about 12 h to allow for expression of the genes. The expression of the fusion protein was verified using western blots.

For purification, transformed bacteria were grown overnight and then lysed using two twelve-minute cycles in a sonicator. Each cycle was made of alternating on/off minutes for the sonicator. The GF-ELP was transitioned using salt and incubating the solution at about 40° C. The GF-ELP was then pelleted by a hot spin with the supernatant being discarded. The GF-ELP in the pellet was solubilized at about 4° C. using a buffer containing dithiotheritol (DTT). The solution was then centrifuged at about 4° C. to pellet the impurities with the GF-ELP in the supernatant. This completed one full cycle of the purification. This was repeated twice for a total for three cycles. After the last cycle the purified GF-ELP was dialyzed against water overnight to remove salts. The dialyzed GF-ELP was then lyophilized and stored until further use.

The physical properties of the purified GF-ELPs were characterized using a UV spectrophotometer and dynamic light scattering. The biological activity of the GF-ELPs was evaluated using h292, a431, and hcc287 cell lines. The uptake of the nanoparticles formed from GF-ELPs was evaluated using flow cytometry and transmission electron microscopy. These results are shown in FIGS. 6A-6B, 9A, and 10.

We claim:

1. A nanoparticle comprising:
a first fusion polypeptide comprising a first elastin-like peptide (ELP) and a targeting moiety configured to specifically bind a binding partner, wherein the targeting moiety induces macropinocytosis when the targeting moiety specifically binds to the binding partner, wherein the targeting moiety is keratinocyte growth factor and the binding partner is keratinocyte growth factor receptor, and wherein the first ELP is operatively linked to the targeting moiety;
a second fusion polypeptide comprising a second ELP and a first cargo molecule, wherein the second ELP is operatively linked to the first cargo molecule, and wherein the nanoparticle self assembles at a temperature that is greater than a phase transition temperature, wherein the first fusion polypeptide and the second fusion polypeptide are present in the nanoparticle at a molar concentration ratio ranging from about 1:1 to 2:1, and wherein the nanoparticle further comprises a cargo binding peptide, and wherein the cargo binding peptide comprises the amino acid sequence of SEQ ID NO: 21.

2. The nanoparticle of claim 1, wherein the first cargo molecule is a mitochondrial lytic peptide.

3. The nanoparticle of claim 2, wherein the mitochondrial lytic peptide comprises the amino acid of SEQ ID NO: 23.

4. The nanoparticle of claim 1, wherein the nanoparticle further comprises a third fusion polypeptide comprising a third ELP and a second cargo molecule, wherein the third ELP is operatively linked to the second cargo molecule, and wherein the second cargo molecule is a glycolysis inhibitor.

5. The nanoparticle of claim 1, wherein the binding partner is located on the surface of a cell.

6. The nanoparticle of claim 5, wherein the cell is a cancer cell.

7. The nanoparticle of claim 1, wherein the phase transition temperature ranges from about 5° C. to about 40° C.

8. The nanoparticle of claim 1, wherein the first or the second ELP comprises the amino acid sequence of any one of SEQ ID NOs: 9, 37, or the amino acid sequence encoded by SEQ ID NO: 38.

9. The nanoparticle of claim 1, wherein the first fusion polypeptide comprises the amino acid of SEQ ID NO: 33.

10. A pharmaceutical formulation comprising:
an effective amount of a nanoparticle, wherein the nanoparticle comprises:
a first fusion polypeptide comprising a first elastin-like peptide (ELP) and a targeting moiety configured to specifically bind a binding partner, wherein the targeting moiety induces macropinocytosis when the targeting moiety specifically binds to the binding partner, wherein the targeting moiety is keratinocyte growth factor and the binding partner is keratinocyte growth factor receptor, and wherein the first ELP is operatively linked to the targeting moiety;
a second fusion polypeptide comprising a second ELP and a first cargo molecule, wherein the second ELP is operatively linked to the first cargo molecule, wherein the nanoparticle self assembles above a phase transition temperature,
wherein the first fusion polypeptide and the second fusion polypeptide are present in the nanoparticle at a molar concentration ratio ranging from about 1:1 to 2:1;
wherein the nanoparticle further comprises a cargo binding peptide, and wherein the cargo binding peptide comprises the amino acid sequence of SEQ ID NO: 21; and
a pharmaceutically acceptable carrier.

11. The pharmaceutical formulation of claim 10, wherein the nanoparticle further comprising a third fusion polypeptide comprising a third ELP and a second cargo molecule, wherein the third ELP is operatively linked to the second cargo molecule.

12. The pharmaceutical formulation of claim 11, wherein the first cargo molecule is a mitochondrial lytic peptide and wherein the second cargo molecule is a glycolysis inhibitor.

13. The pharmaceutical formulation of claim 11, wherein the second fusion polypeptide comprises the amino acid sequence of SEQ ID NO: 31.

14. The pharmaceutical formulation of claim 10, wherein the first cargo molecule is a mitochondrial lytic peptide.

15. The pharmaceutical formulation of claim 10, wherein the amount is effective for killing a lung cancer cell or population thereof.

16. The pharmaceutical formulation of claim 10, wherein the first or the second ELP comprises the amino acid sequence of any one of SEQ ID NOs: 9, 37, or the amino acid sequence encoded by SEQ ID NO: 38.

17. The pharmaceutical formulation of claim 10, wherein the first fusion polypeptide comprises the amino acid sequence of SEQ ID NO: 33.

18. A nanoparticle comprising:
a first fusion polypeptide comprising a first elastin-like peptide (ELP) and a targeting moiety configured to specifically bind a binding partner, wherein the targeting moiety induces macropinocytosis when the targeting moiety specifically binds to the binding partner, wherein the targeting moiety is keratinocyte growth factor and the binding partner is keratinocyte growth factor receptor, and wherein the first ELP is operatively linked to the targeting moiety;
a second fusion polypeptide comprising a second ELP and a first cargo molecule, wherein the second ELP is operatively linked to the first cargo molecule, and wherein the nanoparticle self assembles at a temperature that is greater than a phase transition temperature; and
a cargo binding peptide, wherein the cargo binding peptide is low-density lipoprotein receptor 3 (LDLR3).

\* \* \* \* \*